US012091455B2

(12) United States Patent
Wang et al.

(10) Patent No.: US 12,091,455 B2
(45) Date of Patent: Sep. 17, 2024

(54) COMPOSITIONS FOR MODULATION OF A TREM OR TREML PROTEIN AND METHODS OF USE

(71) Applicant: YALE UNIVERSITY, New Haven, CT (US)

(72) Inventors: Andrew Wang, Hamden, CT (US); Wenjun Liu, New Haven, CT (US); Aaron Ring, New Haven, CT (US)

(73) Assignee: Yale University, New Haven, CT (US)

( * ) Notice: Subject to any disclaimer, the term of this patent is extended or adjusted under 35 U.S.C. 154(b) by 1070 days.

(21) Appl. No.: 16/969,707

(22) PCT Filed: Feb. 14, 2019

(86) PCT No.: PCT/US2019/018044
§ 371 (c)(1),
(2) Date: Aug. 13, 2020

(87) PCT Pub. No.: WO2019/161080
PCT Pub. Date: Aug. 22, 2019

(65) Prior Publication Data
US 2021/0002365 A1 Jan. 7, 2021

Related U.S. Application Data

(60) Provisional application No. 62/771,730, filed on Nov. 27, 2018, provisional application No. 62/630,333, filed on Feb. 14, 2018.

(51) Int. Cl.
*C07K 16/28* (2006.01)
*A61K 35/15* (2015.01)
*A61K 38/16* (2006.01)

(52) U.S. Cl.
CPC .......... *C07K 16/2803* (2013.01); *A61K 35/15* (2013.01); *A61K 38/16* (2013.01); *C07K 2317/71* (2013.01)

(58) Field of Classification Search
CPC ............ C07K 16/2803; C07K 2317/71; A61K 35/15; A61K 38/16
See application file for complete search history.

(56) References Cited

U.S. PATENT DOCUMENTS

| 2009/0312190 A1 | 12/2009 | Chinea Santiago |
| 2010/0306863 A1 | 12/2010 | Colonna |
| 2013/0259923 A1 | 10/2013 | Bancel |

FOREIGN PATENT DOCUMENTS

| WO | WO2016020502 | * 2/2016 | ............ C07K 16/28 |
| WO | 2016166360 | 10/2016 | |

OTHER PUBLICATIONS

NCBI search for TREML4 protein accessed Dec. 12, 2023. (Year: 2023).*
Obermaier et al., Principles of protein labeling. Chapter 13 in Proteomic profiling: Methods and Protocols, Methods in Molecular Biology, vol. 1295, Anton Posch (ed.), Springer Science+Business Media New York, 2015. (Year: 2015).*
Alegre et al., 1992, "Effect of a single amino acid mutation on the activating and immunosuppressive properties of a "humanized" OKT3 monoclonal antibody." J Immunol, 148: 3461-3468.
An et al., 2009, "IgG2m4, an engineered antibody isotype with reduced Fc function." MAbs, 1: 572-579.
Bolt et al., 1993, "The generation of a humanized, non-mitogenic CD3 monoclonal antibody which retains in vitro immunosuppressive properties." Eur J Immunol, 23: 403-411.
Dall'Acqua et al., 2006, "Modulation of the Effector Functions of a Human IgG1 through Engineering of Its Hinge Region." J Immunol, 177(2): 1129-1138.
Hemmi et al., "A New Triggering Receptor Expressed on Myeloid Cells (Trem) Family Member, Trem-Like 4, Binds to Dead Cells and Is a DNAX Activation Protein 12-Linked Marker for Subsets of Mouse Macrophages and Dendritic Cells", The Journal of Immunology, (Feb. 1, 2009), vol. 182, No. 3, doi:10.4049/jimmunol.182.3.1278, ISSN 0022-1767, pp. 1278-1286, XP055631578.
Eabman et al., 2013, "Effects of altered FcγR binding on antibody pharmacokinetics in cynomolgus monkeys." MAbs, 5: 896-903.
Lo et al., 2017, "Effector-attenuating Substitutions That Maintain Antibody Stability and Reduce Toxicity in Mice." J Biol Chem, 292(9): 3900-3908.
Ortiz et al., "TREML4 amplifies TLR7-mediated signaling during antiviral responses and autoimmunity", Nat Immunol, (20150500), vol. 16, No. 5, doi:10.1038/ni.3143, ISSN 1529-2908, pp. 495-504, XP055631583.
Rother et al., 2007, "Discovery and development of the complement inhibitor eculizumab for the treatment of paroxysmal nocturnal hemoglobinuria." Nat Biotechnol, 25: 1256-1264.
Tao and Morrison, 1989, "Studies of aglycosylated chimeric mouse-human IgG. Role of carbohydrate in the structure and effector functions mediated by the human IgG constant region." J Immunol, 143: 2595-2601.
Vafa et al., 2014, "An engineered Fc variant of an IgG eliminates all immune effector functions via structural perturbations." Methods, 65: 114-126.
Walker et al., 1989, "Aglycosylation of human IgG1 and IgG3 monoclonal antibodies can eliminate recognition by human cells expressing Fc gamma RI and/or Fc gamma RII receptors." Biochem J, 347-353.
Wang et al., 2018, "IgG Fc engineering to modulate antibody effector functions." Protein Cell, 9(1): 63-73.
Xu et al., 2000, "In vitro characterization of five humanized OKT3 effector function variant antibodies." Cell Immunol, 200: 16-26.

(Continued)

Primary Examiner — Elly-Gerald Stoica
(74) Attorney, Agent, or Firm — Riverside Law LLP

(57) ABSTRACT

The present invention provides compositions and methods for reducing inflammation. In one aspect, the present invention provides a protein inhibitor comprising an ectodomain of at least one TREM or TREML protein. The invention also relates to inhibiting the interaction between a TREM or TREML protein and mitochondria released or derived from necroptotic cells; or between a TREM or TREML protein and cardiolipin.

31 Claims, 34 Drawing Sheets
Specification includes a Sequence Listing.

(56) References Cited

OTHER PUBLICATIONS

Zaida G Ramirez-Ortiz et al., "The receptor TREML4 amplifies TLR7-mediated signaling during antiviral respnses and autoimmunity " Nature Immunology, 16(5): 495-504.

* cited by examiner

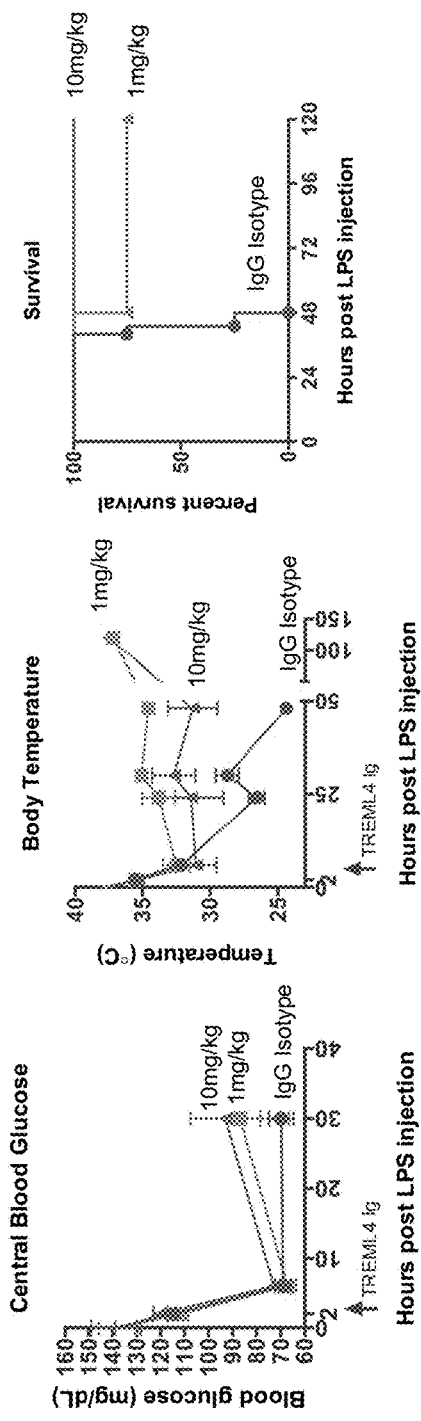
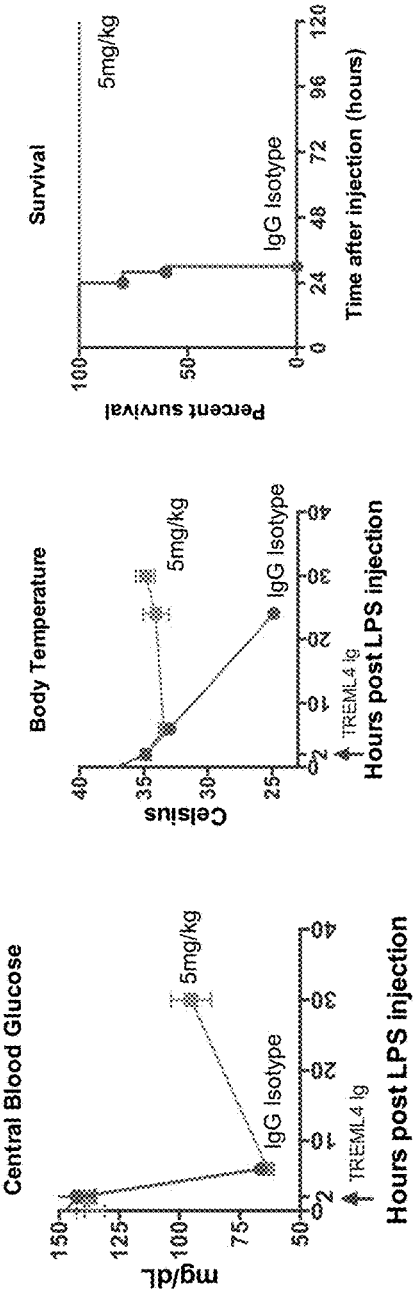
FIG. 2

WT hTREML4 carries mutations that confer AD risk in hTREM2

```
                                                                        L65    K71
(SEQ ID NO: 45)  hTREM2   HNTTVFQGVAGQSLQVSCPYDSMKHWGRRKAWCRQLGEKGPCQRVVSTHNLWLLSFLRRW
(SEQ ID NO: 46)  mTREML4  ----EELHRMVGQSLSVQCQYKPKEESYVLKTWCRQTAP-SKCTLVTTSNPRKAAR-----
(SEQ ID NO: 47)  hTREML4  ----EELHKHPGQTLLLQCQYSPKRGPYQPKSWCQQTSP--SRCTLVTSSKPWTAVQ-----
                              *    **.:* **  *  *   :**::* .  *  *   ::*:*:*

K86    T95
                 hTREM2   NGSTAITDFLGGTLTLRNLQPHDAGLYQCQSLHGSEADT--LRKVLVEVLADPLDHR
                 mTREML4  ELQHTIWDKPEAGFFNIMTQLTEDDSAFYWCGPYYPSLREVTVLRNISLVVSPAPSTLP
                 hTREML4  KSHYTIWDKPNAGFFNIMIQLTQNDSGFYWCGIYNASENIITVLRNISLVVSPAPTTSP
                            *   **  *:** :   ::*. ::   .     :: : ::* hTREM2   DAGDLWFPGESESF---------------EDAHVEHSISR-----------------
                 mTREML4  SQTIAPLPESTATIEMPFPVLTTSPEET-TDSSINGTGHRNQSSSPGWTSPG-------
                 hTREML4  MWTLPWLPTSTVLIT----------------SPECTSGHPSINGSETRKSRA--PA--
                             :               : **.
```

FIG. 6

SEQUENCE LISTING

```
<160> NUMBER OF SEQ ID NOS: 47

<210> SEQ ID NO 1
<211> LENGTH: 150
<212> TYPE: PRT
<213> ORGANISM: Artificial Sequence
<220> FEATURE:
<223> OTHER INFORMATION: ectodomain of human TREML4
```

<400> SEQUENCE: 1

```
Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
            115                 120                 125

Pro Glu Gly Thr Ser Gly His Pro Ser Ile Asn Gly Ser Glu Thr Arg
        130                 135                 140

Lys Ser Arg Ala Pro Ala
145                 150
```

<210> SEQ ID NO 2
<211> LENGTH: 150
<212> TYPE: PRT
<213> ORGANISM: Artificial Sequence
<220> FEATURE:
<223> OTHER INFORMATION: ectodomain of hTREML4-K86D

<400> SEQUENCE: 2

```
Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Lys Ser His Tyr Thr Ile Trp Asp Asp Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
            115                 120                 125

Pro Glu Gly Thr Ser Gly His Pro Ser Ile Asn Gly Ser Glu Thr Arg
        130                 135                 140

Lys Ser Arg Ala Pro Ala
145                 150
```

<210> SEQ ID NO 3
<211> LENGTH: 150
<212> TYPE: PRT
<213> ORGANISM: Artificial Sequence
<220> FEATURE:

<223> OTHER INFORMATION: ectodomain of hTREML4-L65R

<400> SEQUENCE: 3

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Arg Leu Val Thr Ser Ser Lys Pro Trp
        35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Gly Thr Ser Gly His Pro Ser Ile Asn Gly Ser Glu Thr Arg
    130                 135                 140

Lys Ser Arg Ala Pro Ala
145                 150

<210> SEQ ID NO 4
<211> LENGTH: 149
<212> TYPE: PRT
<213> ORGANISM: Artificial Sequence
<220> FEATURE:
<223> OTHER INFORMATION: ectodomain of hTREML4-K71E

<400> SEQUENCE: 4

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Glu Pro Trp
        35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Gly Thr Ser Gly His Pro Ser Ile Asn Gly Ser Glu Thr Arg
    130                 135                 140

Lys Ser Arg Ala Pro
145

<210> SEQ ID NO 5
<211> LENGTH: 150
<212> TYPE: PRT
<213> ORGANISM: Artificial Sequence
<220> FEATURE:
<223> OTHER INFORMATION: ectodomain of hTREML4-T95K

<400> SEQUENCE: 5

Glu Glu Leu His Lys His Pro Gly Gln Thr Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Lys Ser His Tyr Thr Ile Trp Asp Lys Pro Asn Ala
    50                  55                  60

Gly Phe Phe Asn Ile Lys Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
            115                 120                 125

Pro Glu Gly Thr Ser Gly His Pro Ser Ile Asn Gly Ser Glu Thr Arg
        130                 135                 140

Lys Ser Arg Ala Pro Ala
145                 150

<210> SEQ ID NO 6
<211> LENGTH: 150
<212> TYPE: PRT
<213> ORGANISM: Artificial Sequence
<220> FEATURE:
<223> OTHER INFORMATION: ectodomain of hTREML4-T35S

<400> SEQUENCE: 6

Glu Glu Leu His Lys His Pro Gly Gln Ser Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
            115                 120                 125

Pro Glu Gly Thr Ser Gly His Pro Ser Ile Asn Gly Ser Glu Thr Arg
        130                 135                 140

Lys Ser Arg Ala Pro Ala
145                 150

<210> SEQ ID NO 7
<211> LENGTH: 150
<212> TYPE: PRT

<213> ORGANISM: Artificial Sequence
<220> FEATURE:
<223> OTHER INFORMATION: ectodomain of hTREML4-L66V

<400> SEQUENCE: 7

```
Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
                20                  25                  30

Thr Ser Pro Ser Arg Cys Thr Leu Val Val Thr Ser Lys Pro Trp
            35                  40                  45

Thr Ala Val Gln Lys Ser His Tyr Thr Ile Trp Asp Lys Pro Asn Ala
        50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
            115                 120                 125

Pro Glu Gly Thr Ser Gly His Pro Ser Ile Asn Gly Ser Glu Thr Arg
        130                 135                 140

Lys Ser Arg Ala Pro Ala
145                 150
```

<210> SEQ ID NO 8
<211> LENGTH: 150
<212> TYPE: PRT
<213> ORGANISM: Artificial Sequence
<220> FEATURE:
<223> OTHER INFORMATION: ectodomain of hTREML4-S69T

<400> SEQUENCE: 8

```
Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
                20                  25                  30

Thr Ser Pro Ser Arg Cys Thr Leu Leu Val Thr Thr Ser Lys Pro Trp
            35                  40                  45

Thr Ala Val Gln Lys Ser His Tyr Thr Ile Trp Asp Lys Pro Asn Ala
        50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
            115                 120                 125

Pro Glu Gly Thr Ser Gly His Pro Ser Ile Asn Gly Ser Glu Thr Arg
        130                 135                 140

Lys Ser Arg Ala Pro Ala
145                 150
```

<210> SEQ ID NO 9
<211> LENGTH: 150

```
<212> TYPE: PRT
<213> ORGANISM: Artificial Sequence
<220> FEATURE:
<223> OTHER INFORMATION: ectodomain of hTREML4-K78E

<400> SEQUENCE: 9

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Glu Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Gly Thr Ser Gly His Pro Ser Ile Asn Gly Ser Glu Thr Arg
    130                 135                 140

Lys Ser Arg Ala Pro Ala
145                 150

<210> SEQ ID NO 10
<211> LENGTH: 150
<212> TYPE: PRT
<213> ORGANISM: Artificial Sequence
<220> FEATURE:
<223> OTHER INFORMATION: ectodomain of hTREML4-G156E

<400> SEQUENCE: 10

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Glu Thr Ser Gly His Pro Ser Ile Asn Gly Ser Glu Thr Arg
    130                 135                 140

Lys Ser Arg Ala Pro Ala
145                 150

<210> SEQ ID NO 11
```

```
<211> LENGTH: 150
<212> TYPE: PRT
<213> ORGANISM: Artificial Sequence
<220> FEATURE:
<223> OTHER INFORMATION: ectodomain of hTREML4-H160D

<400> SEQUENCE: 11
```

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Leu Leu Val Thr Ser Ser Lys Pro Trp
        35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Gly Thr Ser Gly Asp Pro Ser Ile Asn Gly Ser Glu Thr Arg
    130                 135                 140

Lys Ser Arg Ala Pro Ala
145                 150

```
<210> SEQ ID NO 12
<211> LENGTH: 150
<212> TYPE: PRT
<213> ORGANISM: Artificial Sequence
<220> FEATURE:
<223> OTHER INFORMATION: ectodomain of hTREML4-L65R/K71E/K86D

<400> SEQUENCE: 12
```

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Arg Leu Val Thr Ser Ser Glu Pro Trp
        35                  40                  45

Thr Ala Val Gln Lys Ser His Tyr Thr Ile Trp Asp Asp Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Gly Thr Ser Gly His Pro Ser Ile Asn Gly Ser Glu Thr Arg
    130                 135                 140

Lys Ser Arg Ala Pro Ala
145                 150

<210> SEQ ID NO 13
<211> LENGTH: 150
<212> TYPE: PRT
<213> ORGANISM: Artificial Sequence
<220> FEATURE:
<223> OTHER INFORMATION: ectodomain of hTREML4-L65R/K71E/K86D/T95K

<400> SEQUENCE: 13

```
Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
            20                  25                  30

Thr Ser Pro Ser Arg Cys Thr Arg Leu Val Thr Ser Ser Glu Pro Trp
        35                  40                  45

Thr Ala Val Gln Lys Ser His Tyr Thr Ile Trp Asp Asp Pro Asn Ala
    50                  55                  60

Gly Phe Phe Asn Ile Lys Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
            100                 105                 110

Met Trp Thr Leu Pro Trp Leu Pro Thr Ser Thr Val Leu Ile Thr Ser
        115                 120                 125

Pro Glu Gly Thr Ser Gly His Pro Ser Ile Asn Gly Ser Glu Thr Arg
    130                 135                 140

Lys Ser Arg Ala Pro Ala
145                 150
```

<210> SEQ ID NO 14
<211> LENGTH: 164
<212> TYPE: PRT
<213> ORGANISM: Artificial Sequence
<220> FEATURE:
<223> OTHER INFORMATION: ectodomain of murine TREML4

<400> SEQUENCE: 14

```
Glu Glu Leu His Arg Met Val Gly Gln Ser Leu Ser Val Gln Cys Gln
1               5                   10                  15

Tyr Lys Pro Lys Glu Glu Ser Tyr Val Leu Lys Thr Trp Cys Arg Gln
            20                  25                  30

Thr Ala Pro Ser Lys Cys Thr Arg Val Val Thr Thr Ser Glu Pro Arg
        35                  40                  45

Lys Ala Ala Arg Glu Leu Gln His Thr Ile Trp Asp Asp Pro Glu Ala
    50                  55                  60

Gly Phe Phe Asn Ile Thr Met Thr Gln Leu Thr Glu Asp Asp Ser Ala
65                  70                  75                  80

Phe Tyr Trp Cys Gly Pro Tyr Tyr Pro Ser Leu Arg Glu Val Thr Val
                85                  90                  95

Leu Arg Asn Ile Ser Leu Val Val Ser Pro Ala Pro Ser Thr Leu Pro
            100                 105                 110

Ser Gln Thr Ile Ala Pro Leu Pro Glu Ser Thr Ala Thr Ile Phe Met
        115                 120                 125

Pro Phe Pro Val Leu Thr Thr Ser Pro Glu Glu Thr Thr Asp Ser Ser
    130                 135                 140

Ile Asn Gly Thr Gly His Arg Asn Gln Ser Ser Ser Ser Pro Gly Trp
145                 150                 155                 160
```

```
Thr Ser Pro Gly

<210> SEQ ID NO 15
<211> LENGTH: 143
<212> TYPE: PRT
<213> ORGANISM: Artificial Sequence
<220> FEATURE:
<223> OTHER INFORMATION: ectodomain of TREM2

<400> SEQUENCE: 15

His Asn Thr Thr Val Phe Gln Gly Val Ala Gly Gln Ser Leu Gln Val
1               5                   10                  15

Ser Cys Pro Tyr Asp Ser Met Lys His Trp Gly Arg Arg Lys Ala Trp
            20                  25                  30

Cys Arg Gln Leu Gly Glu Lys Gly Pro Cys Gln Arg Val Val Ser Thr
        35                  40                  45

His Asn Leu Trp Leu Leu Ser Phe Leu Arg Arg Trp Asn Gly Ser Thr
    50                  55                  60

Ala Ile Thr Asp Asp Thr Leu Gly Gly Thr Leu Thr Ile Thr Leu Arg
65                  70                  75                  80

Asn Leu Gln Pro His Asp Ala Gly Leu Tyr Gln Cys Gln Ser Leu His
                85                  90                  95

Gly Ser Glu Ala Asp Thr Leu Arg Lys Val Leu Val Glu Val Leu Ala
            100                 105                 110

Asp Pro Leu Asp His Arg Asp Ala Gly Asp Leu Trp Phe Pro Gly Glu
        115                 120                 125

Ser Glu Ser Phe Glu Asp Ala His Val Glu His Ser Ile Ser Arg
    130                 135                 140

<210> SEQ ID NO 16
<211> LENGTH: 152
<212> TYPE: PRT
<213> ORGANISM: Artificial Sequence
<220> FEATURE:
<223> OTHER INFORMATION: ectodomain of human TREM1

<400> SEQUENCE: 16

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
        35                  40                  45

Cys Thr Glu Arg Pro Ser Lys Asn Ser His Pro Val Gln Val Gly Arg
    50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
            100                 105                 110

Val Thr Lys Gly Phe Ser Gly Thr Pro Gly Ser Asn Glu Asn Ser Thr
        115                 120                 125

Gln Asn Val Tyr Lys Ile Pro Pro Thr Thr Thr Lys Ala Leu Cys Pro
    130                 135                 140

Leu Tyr Thr Ser Pro Arg Thr Val
145                 150
```

```
<210> SEQ ID NO 17
<211> LENGTH: 147
<212> TYPE: PRT
<213> ORGANISM: Artificial Sequence
<220> FEATURE:
<223> OTHER INFORMATION: ectodomain of TREML1

<400> SEQUENCE: 17

Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ser Ala Val Asp Arg Arg Ala Pro Ala Gly Arg Arg Thr Phe Leu
    50                  55                  60

Thr Asp Leu Gly Gly Gly Leu Leu Gln Val Glu Met Val Thr Leu Gln
65                  70                  75                  80

Glu Glu Asp Ala Gly Glu Tyr Gly Cys Met Val Asp Gly Ala Arg Gly
                85                  90                  95

Pro Gln Ile Leu His Arg Val Ser Leu Asn Ile Leu Pro Pro Glu Glu
            100                 105                 110

Glu Glu Glu Thr His Lys Ile Gly Ser Leu Ala Glu Asn Ala Phe Ser
        115                 120                 125

Asp Pro Ala Gly Ser Ala Asn Pro Leu Glu Pro Ser Gln Asp Glu Lys
    130                 135                 140

Ser Ile Pro
145

<210> SEQ ID NO 18
<211> LENGTH: 163
<212> TYPE: PRT
<213> ORGANISM: Artificial Sequence
<220> FEATURE:
<223> OTHER INFORMATION: ectodomain of TREML2

<400> SEQUENCE: 18

Pro Ser Ala Asp Ser Val Tyr Thr Lys Val Arg Leu Leu Glu Gly Glu
1               5                   10                  15

Thr Leu Ser Val Gln Cys Ser Tyr Lys Gly Tyr Lys Asn Arg Val Glu
            20                  25                  30

Gly Lys Val Trp Cys Lys Ile Arg Lys Lys Cys Glu Pro Gly Phe
        35                  40                  45

Ala Arg Val Trp Val Lys Gly Pro Arg Tyr Leu Leu Gln Asp Asp Ala
    50                  55                  60

Gln Ala Lys Val Val Asn Ile Thr Met Val Ala Leu Lys Leu Gln Asp
65                  70                  75                  80

Ser Gly Arg Tyr Trp Cys Met Arg Asn Thr Ser Gly Ile Leu Tyr Pro
                85                  90                  95

Leu Met Gly Phe Gln Leu Asp Val Ser Pro Ala Pro Gln Thr Glu Arg
            100                 105                 110

Asn Ile Pro Phe Thr His Leu Asp Asn Ile Leu Lys Ser Gly Thr Val
        115                 120                 125

Thr Thr Gly Gln Ala Pro Thr Ser Gly Pro Asp Ala Pro Phe Thr Thr
    130                 135                 140

Gly Val Met Val Phe Thr Pro Gly Leu Ile Thr Leu Pro Arg Leu Leu
145                 150                 155                 160
```

<210> SEQ ID NO 19
<211> LENGTH: 227
<212> TYPE: PRT
<213> ORGANISM: Artificial Sequence
<220> FEATURE:
<223> OTHER INFORMATION: Fc domain of wild-type human IgG1

<400> SEQUENCE: 19

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 20
<211> LENGTH: 227
<212> TYPE: PRT
<213> ORGANISM: Artificial Sequence
<220> FEATURE:
<223> OTHER INFORMATION: Fc domain of human IgG1 (N297Q mutation)

<400> SEQUENCE: 20

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Gln Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 227
<212> TYPE: PRT
<213> ORGANISM: Artificial Sequence
<220> FEATURE:
<223> OTHER INFORMATION: Fc domain of human IgG1 (N297A mutation)

<400> SEQUENCE: 21

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 22
<211> LENGTH: 227
<212> TYPE: PRT
<213> ORGANISM: Artificial Sequence
<220> FEATURE:
<223> OTHER INFORMATION: Fc domain of human IgG1 (N297G mutation)

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 23
<211> LENGTH: 13
<212> TYPE: PRT
<213> ORGANISM: Artificial Sequence
<220> FEATURE:
<223> OTHER INFORMATION: linker domain

<400> SEQUENCE: 23

Gly Gly Gly Ser Gly Gly Ser Gly Gly Ser Gly Gly Ser
1               5                   10
```

```
<210> SEQ ID NO 24
<211> LENGTH: 5
<212> TYPE: PRT
<213> ORGANISM: Artificial Sequence
<220> FEATURE:
<223> OTHER INFORMATION: linker domain

<400> SEQUENCE: 24

Gly Gly Gly Gly Ser
1               5

<210> SEQ ID NO 25
<211> LENGTH: 19
<212> TYPE: PRT
<213> ORGANISM: Artificial Sequence
<220> FEATURE:
<223> OTHER INFORMATION: leader sequence

<400> SEQUENCE: 25

Met Glu Phe Gly Leu Ser Trp Val Phe Leu Val Ala Leu Phe Arg Gly
1               5                   10                  15

Val Gln Ser

<210> SEQ ID NO 26
<211> LENGTH: 411
<212> TYPE: PRT
<213> ORGANISM: Artificial Sequence
<220> FEATURE:
<223> OTHER INFORMATION: Leader- ectodomain of hTREML4- linker- Fc
      domain of human IgG1(glycosylation site N297Q mutation)

<400> SEQUENCE: 26

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Ser Ser
    50                  55                  60

Lys Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220
```

```
Cys Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
            245                 250                 255

Glu Glu Gln Tyr Gln Ser Thr Tyr Arg Val Val Ser Val Leu Thr Val
                260                 265                 270

Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
                340                 345                 350

Asn Asn Tyr Lys Thr Thr Pro Pro Val Leu Asp Ser Asp Gly Ser Phe
            355                 360                 365

Phe Leu Tyr Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 27
<211> LENGTH: 411
<212> TYPE: PRT
<213> ORGANISM: Artificial Sequence
<220> FEATURE:
<223> OTHER INFORMATION: Leader- ectodomain of hTREML4-K86D- linker- Fc
      domain of human IgG1(glycosylation site N297Q mutation)

<400> SEQUENCE: 27

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Ser Ser
    50                  55                  60

Lys Pro Trp Thr Ala Val Gln Lys Ser His Tyr Thr Ile Trp Asp Asp
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Gly Ser Gly Gly
```

```
                165                 170                 175
Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
            195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 28
<211> LENGTH: 411
<212> TYPE: PRT
<213> ORGANISM: Artificial Sequence
<220> FEATURE:
<223> OTHER INFORMATION: leader- ectodomain of hTREML4-L65R- Linker- Fc
      domain of human IgG1(glycosylation site N297Q mutation)

<400> SEQUENCE: 28

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Arg Leu Val Thr Ser Ser
    50                  55                  60

Lys Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110
```

```
Ile Thr Val Leu Arg Asn Ile Ser Leu Val Val Ser Pro Ala Pro Thr
            115                 120                 125

Thr Ser Pro Met Trp Thr Leu Pro Trp Leu Pro Thr Ser Thr Val Leu
130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
                195                 200                 205

Pro Lys Pro Lys Asp Thr Leu Met Ile Ser Arg Thr Pro Glu Val Thr
        210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
                260                 265                 270

Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
                290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
                340                 345                 350

Asn Asn Tyr Lys Thr Thr Pro Pro Val Leu Asp Ser Asp Gly Ser Phe
            355                 360                 365

Phe Leu Tyr Ser Lys Leu Thr Val Asp Lys Ser Arg Trp Gln Gln Gly
370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
            405                 410

<210> SEQ ID NO 29
<211> LENGTH: 411
<212> TYPE: PRT
<213> ORGANISM: Artificial Sequence
<220> FEATURE:
<223> OTHER INFORMATION: leader- ectodomain of hTREML4-K71E- Linker- Fc
      domain of human IgG1(glycosylation site N297Q mutation)

<400> SEQUENCE: 29

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
                20                  25                  30

Gln Cys Gln Tyr Ser Pro Lys Arg Gly Pro Tyr Gln Pro Lys Ser Trp
            35                  40                  45

Cys Gln Gln Thr Ser Pro Ser Arg Cys Thr Leu Leu Val Thr Ser Ser
        50                  55                  60
```

Glu Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 30
<211> LENGTH: 411
<212> TYPE: PRT
<213> ORGANISM: Artificial Sequence
<220> FEATURE:
<223> OTHER INFORMATION: Leader- ectodomain of hTREML4-T95K- Linker- Fc
      domain of human IgG1(glycosylation site N297Q mutation)

<400> SEQUENCE: 30

Met Glu Phe Gly Leu Ser Trp Val Phe Leu Val Ala Leu Phe Arg Gly

```
1               5                   10                  15
Val Gln Ser Glu Glu Leu His Lys His Pro Gly Gln Thr Leu Leu Leu
            20                  25                  30
Gln Cys Gln Tyr Ser Pro Lys Arg Gly Pro Tyr Gln Pro Lys Ser Trp
            35                  40                  45
Cys Gln Gln Thr Ser Pro Ser Arg Cys Thr Leu Leu Val Thr Ser Ser
            50                  55                  60
Lys Pro Trp Thr Ala Val Gln Lys Ser His Tyr Thr Ile Trp Asp Lys
65                  70                  75                  80
Pro Asn Ala Gly Phe Phe Asn Ile Lys Met Ile Gln Leu Thr Gln Asn
                85                  90                  95
Asp Ser Gly Phe Tyr Trp Cys Gly Ile Tyr Asn Ala Ser Glu Asn Ile
                100                 105                 110
Ile Thr Val Leu Arg Asn Ile Ser Leu Val Val Ser Pro Ala Pro Thr
                115                 120                 125
Thr Ser Pro Met Trp Thr Leu Pro Trp Leu Pro Thr Ser Thr Val Leu
                130                 135                 140
Ile Thr Ser Pro Glu Gly Thr Ser Gly His Pro Ser Ile Asn Gly Ser
145                 150                 155                 160
Glu Thr Arg Lys Ser Arg Ala Pro Ala Gly Gly Gly Ser Gly Gly
                165                 170                 175
Gly Gly Ser Gly Gly Gly Ser Asp Lys Thr His Thr Cys Pro Pro
                180                 185                 190
Cys Pro Ala Pro Glu Leu Leu Gly Gly Pro Ser Val Phe Leu Phe Pro
                195                 200                 205
Pro Lys Pro Lys Asp Thr Leu Met Ile Ser Arg Thr Pro Glu Val Thr
                210                 215                 220
Cys Val Val Val Asp Val Ser His Glu Asp Pro Glu Val Lys Phe Asn
225                 230                 235                 240
Trp Tyr Val Asp Gly Val Glu Val His Asn Ala Lys Thr Lys Pro Arg
                245                 250                 255
Glu Glu Gln Tyr Gln Ser Thr Tyr Arg Val Val Ser Val Leu Thr Val
                260                 265                 270
Leu His Gln Asp Trp Leu Asn Gly Lys Glu Tyr Lys Cys Lys Val Ser
                275                 280                 285
Asn Lys Ala Leu Pro Ala Pro Ile Glu Lys Thr Ile Ser Lys Ala Lys
                290                 295                 300
Gly Gln Pro Arg Glu Pro Gln Val Tyr Thr Leu Pro Pro Ser Arg Glu
305                 310                 315                 320
Glu Met Thr Lys Asn Gln Val Ser Leu Thr Cys Leu Val Lys Gly Phe
                325                 330                 335
Tyr Pro Ser Asp Ile Ala Val Glu Trp Glu Ser Asn Gly Gln Pro Glu
                340                 345                 350
Asn Asn Tyr Lys Thr Thr Pro Pro Val Leu Asp Ser Asp Gly Ser Phe
                355                 360                 365
Phe Leu Tyr Ser Lys Leu Thr Val Asp Lys Ser Arg Trp Gln Gln Gly
                370                 375                 380
Asn Val Phe Ser Cys Ser Val Met His Glu Ala Leu His Asn His Tyr
385                 390                 395                 400
Thr Gln Lys Ser Leu Ser Leu Ser Pro Gly Lys
                405                 410

<210> SEQ ID NO 31
```

<211> LENGTH: 411
<212> TYPE: PRT
<213> ORGANISM: Artificial Sequence
<220> FEATURE:
<223> OTHER INFORMATION: Leader- ectodomain of hTREML4-T35S- Linker- Fc
domain of human IgG1(glycosylation site N297Q mutation)

<400> SEQUENCE: 31

```
Met Glu Phe Gly Leu Ser Trp Val Phe Leu Val Ala Leu Phe Arg Gly
1               5                   10                  15

Val Gln Ser Glu Glu Leu His Lys His Pro Gly Gln Ser Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Ser Ser
    50                  55                  60

Lys Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
```

```
                    370                 375                 380
Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 32
<211> LENGTH: 411
<212> TYPE: PRT
<213> ORGANISM: Artificial Sequence
<220> FEATURE:
<223> OTHER INFORMATION: Leader- ectodomain of hTREML4-L66V- Linker- Fc
      domain of human IgG1(glycosylation site N297Q mutation)

<400> SEQUENCE: 32

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
                20                  25                  30

Gln Cys Gln Tyr Ser Pro Lys Arg Gly Pro Tyr Gln Pro Lys Ser Trp
            35                  40                  45

Cys Gln Gln Thr Ser Pro Ser Arg Cys Thr Leu Val Val Thr Ser Ser
        50                  55                  60

Lys Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
        290                 295                 300

Gly Gln Pro Arg Glu Pro Gln Val Tyr Thr Leu Pro Pro Ser Arg Glu
305                 310                 315                 320
```

```
Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
                355                 360                 365

Phe Leu Tyr Ser Lys Leu Thr Val Asp Lys Ser Arg Trp Gln Gln Gly
370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410
```

<210> SEQ ID NO 33
<211> LENGTH: 411
<212> TYPE: PRT
<213> ORGANISM: Artificial Sequence
<220> FEATURE:
<223> OTHER INFORMATION: Leader- ectodomain of hTREML4-S69T- Linker- Fc
    domain of human IgG1(glycosylation site N297Q mutation)

<400> SEQUENCE: 33

```
Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Thr Ser
50                  55                  60

Lys Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
        130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
            260                 265                 270
```

-continued

```
Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
        290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
                340                 345                 350

Asn Asn Tyr Lys Thr Thr Pro Pro Val Leu Asp Ser Asp Gly Ser Phe
                355                 360                 365

Phe Leu Tyr Ser Lys Leu Thr Val Asp Lys Ser Arg Trp Gln Gln Gly
        370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410
```

<210> SEQ ID NO 34
<211> LENGTH: 411
<212> TYPE: PRT
<213> ORGANISM: Artificial Sequence
<220> FEATURE:
<223> OTHER INFORMATION: Leader- ectodomain of hTREML4-K78E- Linker- Fc
      domain of human IgG1(glycosylation site N297Q mutation)

<400> SEQUENCE: 34

```
Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Ser Ser
    50                  55                  60

Lys Pro Trp Thr Ala Val Gln Glu Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
```

```
                210                 215                 220
Cys Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
            245                 250                 255

Glu Glu Gln Tyr Gln Ser Thr Tyr Arg Val Val Ser Val Leu Thr Val
                260                 265                 270

Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
            355                 360                 365

Phe Leu Tyr Ser Lys Leu Thr Val Asp Lys Ser Arg Trp Gln Gln Gly
        370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 35
<211> LENGTH: 411
<212> TYPE: PRT
<213> ORGANISM: Artificial Sequence
<220> FEATURE:
<223> OTHER INFORMATION: Leader- ectodomain of hTREML4-G156E- Linker- Fc
      domain of human IgG1(glycosylation site N297Q mutation)

<400> SEQUENCE: 35

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Ser Ser
    50                  55                  60

Lys Pro Trp Thr Ala Val Gln Lys Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Glu Thr Ser Gly His Pro Ser Ile Asn Gly Ser
145                 150                 155                 160
```

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
                260                 265                 270

Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
        290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
                340                 345                 350

Asn Asn Tyr Lys Thr Thr Pro Pro Val Leu Asp Ser Asp Gly Ser Phe
            355                 360                 365

Phe Leu Tyr Ser Lys Leu Thr Val Asp Lys Ser Arg Trp Gln Gln Gly
        370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 36
<211> LENGTH: 411
<212> TYPE: PRT
<213> ORGANISM: Artificial Sequence
<220> FEATURE:
<223> OTHER INFORMATION: Leader- ectodomain of hTREML4-H160D- Linker- Fc
      domain of human IgG1(glycosylation site N297Q mutation)

<400> SEQUENCE: 36

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Leu Leu Val Thr Ser Ser
    50                  55                  60

Lys Pro Trp Thr Ala Val Gln Ser His Tyr Thr Ile Trp Asp Lys
65                  70                  75                  80

Pro Asn Ala Gly Phe Phe Asn Ile Thr Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
        130                 135                 140

Ile Thr Ser Pro Glu Gly Thr Ser Gly Asp Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
                180                 185                 190

Cys Pro Ala Pro Glu Leu Leu Gly Gly Pro Ser Val Phe Leu Phe Pro
                195                 200                 205

Pro Lys Pro Lys Asp Thr Leu Met Ile Ser Arg Thr Pro Glu Val Thr
        210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
                260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
        290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
                340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
        370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 37
<211> LENGTH: 411
<212> TYPE: PRT
<213> ORGANISM: Artificial Sequence
<220> FEATURE:
<223> OTHER INFORMATION: Leader- ectodomain of hTREML4-L65R/K71E/K86D-
      Linker- Fc domain of human IgG1(a glycosylation site N297Q
      mutation)

<400> SEQUENCE: 37

Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
                20                  25                  30

Gln Cys Gln Tyr Ser Pro Lys Arg Gly Pro Tyr Gln Pro Lys Ser Trp
        35                  40                  45

```
Cys Gln Gln Thr Ser Pro Ser Arg Cys Thr Arg Leu Val Thr Ser Ser
 50                  55                  60

Glu Pro Trp Thr Ala Val Gln Lys Ser His Tyr Thr Ile Trp Asp Asp
 65                  70                  75                  80

Pro Asn Ala Gly Phe Phe Asn Ile Thr Met Ile Gln Leu Thr Gln Asn
                 85                  90                  95

Asp Ser Gly Phe Tyr Trp Cys Gly Ile Tyr Asn Ala Ser Glu Asn Ile
                100                 105                 110

Ile Thr Val Leu Arg Asn Ile Ser Leu Val Val Ser Pro Ala Pro Thr
            115                 120                 125

Thr Ser Pro Met Trp Thr Leu Pro Trp Leu Pro Thr Ser Thr Val Leu
130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
            195                 200                 205

Pro Lys Pro Lys Asp Thr Leu Met Ile Ser Arg Thr Pro Glu Val Thr
210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
                260                 265                 270

Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
            290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
                340                 345                 350

Asn Asn Tyr Lys Thr Thr Pro Pro Val Leu Asp Ser Asp Gly Ser Phe
                355                 360                 365

Phe Leu Tyr Ser Lys Leu Thr Val Asp Lys Ser Arg Trp Gln Gln Gly
            370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 38
<211> LENGTH: 411
<212> TYPE: PRT
<213> ORGANISM: Artificial Sequence
<220> FEATURE:
<223> OTHER INFORMATION: Leader- ectodomain of
      hTREML4-L65R/K71E/K86D/T95K- Linker- Fc domain of human IgG1(a
      glycosylation site N297Q mutation)
```

<400> SEQUENCE: 38

```
Met Glu Phe Gly Leu Ser Trp Val Phe Leu Val Ala Leu Phe Arg Gly
1               5                   10                  15

Val Gln Ser Glu Glu Leu His Lys His Pro Gly Gln Thr Leu Leu Leu
            20                  25                  30

Gln Cys Gln Tyr Ser Pro Lys Arg Gly Pro Tyr Gln Pro Lys Ser Trp
        35                  40                  45

Cys Gln Gln Thr Ser Pro Ser Arg Cys Thr Arg Leu Val Thr Ser Ser
    50                  55                  60

Glu Pro Trp Thr Ala Val Gln Lys Ser His Tyr Thr Ile Trp Asp Asp
65                  70                  75                  80

Pro Asn Ala Gly Phe Phe Asn Ile Lys Met Ile Gln Leu Thr Gln Asn
                85                  90                  95

Asp Ser Gly Phe Tyr Trp Cys Gly Ile Tyr Asn Ala Ser Glu Asn Ile
            100                 105                 110

Ile Thr Val Leu Arg Asn Ile Ser Leu Val Val Ser Pro Ala Pro Thr
        115                 120                 125

Thr Ser Pro Met Trp Thr Leu Pro Trp Leu Pro Thr Ser Thr Val Leu
    130                 135                 140

Ile Thr Ser Pro Glu Gly Thr Ser Gly His Pro Ser Ile Asn Gly Ser
145                 150                 155                 160

Glu Thr Arg Lys Ser Arg Ala Pro Ala Gly Gly Gly Ser Gly Gly
                165                 170                 175

Gly Gly Ser Gly Gly Gly Ser Asp Lys Thr His Thr Cys Pro Pro
            180                 185                 190

Cys Pro Ala Pro Glu Leu Leu Gly Gly Pro Ser Val Phe Leu Phe Pro
    195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Gln Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410
```

<210> SEQ ID NO 39
<211> LENGTH: 425
<212> TYPE: PRT
<213> ORGANISM: Artificial Sequence
<220> FEATURE:
<223> OTHER INFORMATION: Leader- ectodomain of murine TREML4 - Linker-
      Fc domain of human IgG1(a glycosylation site N297Q mutation)

<400> SEQUENCE: 39

```
Met Glu Phe Gly Leu Ser Trp Val Phe Leu Val Ala Leu Phe Arg Gly
1               5                   10                  15

Val Gln Ser Glu Glu Leu His Arg Met Val Gly Gln Ser Leu Ser Val
            20                  25                  30

Gln Cys Gln Tyr Lys Pro Lys Glu Glu Ser Tyr Val Leu Lys Thr Trp
        35                  40                  45

Cys Arg Gln Thr Ala Pro Ser Lys Cys Thr Arg Val Val Thr Thr Ser
    50                  55                  60

Glu Pro Arg Lys Ala Ala Arg Glu Leu Gln His Thr Ile Trp Asp Asp
65                  70                  75                  80

Pro Glu Ala Gly Phe Phe Asn Ile Thr Met Thr Gln Leu Thr Glu Asp
                85                  90                  95

Asp Ser Ala Phe Tyr Trp Cys Gly Pro Tyr Tyr Pro Ser Leu Arg Glu
            100                 105                 110

Val Thr Val Leu Arg Asn Ile Ser Leu Val Val Ser Pro Ala Pro Ser
        115                 120                 125

Thr Leu Pro Ser Gln Thr Ile Ala Pro Leu Pro Glu Ser Thr Ala Thr
    130                 135                 140

Ile Phe Met Pro Phe Pro Val Leu Thr Thr Ser Pro Glu Glu Thr Thr
145                 150                 155                 160

Asp Ser Ser Ile Asn Gly Thr Gly His Arg Asn Gln Ser Ser Ser Ser
                165                 170                 175

Pro Gly Trp Thr Ser Pro Gly Gly Gly Gly Ser Gly Gly Gly Gly
            180                 185                 190

Ser Gly Gly Gly Gly Ser Asp Lys Thr His Thr Cys Pro Pro Cys Pro
        195                 200                 205

Ala Pro Glu Leu Leu Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Gln Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
```

```
                355                 360                 365
Tyr Lys Thr Thr Pro Val Leu Asp Ser Asp Gly Ser Phe Phe Leu
        370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
                420                 425

<210> SEQ ID NO 40
<211> LENGTH: 404
<212> TYPE: PRT
<213> ORGANISM: Artificial Sequence
<220> FEATURE:
<223> OTHER INFORMATION: Leader- ectodomain of human TREM2- Linker- Fc
      domain of human IgG1(a glycosylation site N297Q mutation)

<400> SEQUENCE: 40

Met Glu Phe Gly Leu Ser Trp Val Phe Leu Val Ala Leu Phe Arg Gly
1               5                   10                  15

Val Gln Ser His Asn Thr Thr Val Phe Gln Gly Val Ala Gly Gln Ser
                20                  25                  30

Leu Gln Val Ser Cys Pro Tyr Asp Ser Met Lys His Trp Gly Arg Arg
            35                  40                  45

Lys Ala Trp Cys Arg Gln Leu Gly Glu Lys Gly Pro Cys Gln Arg Val
        50                  55                  60

Val Ser Thr His Asn Leu Trp Leu Leu Ser Phe Leu Arg Arg Trp Asn
65                  70                  75                  80

Gly Ser Thr Ala Ile Thr Asp Asp Thr Leu Gly Gly Thr Leu Thr Ile
                85                  90                  95

Thr Leu Arg Asn Leu Gln Pro His Asp Ala Gly Leu Tyr Gln Cys Gln
                100                 105                 110

Ser Leu His Gly Ser Glu Ala Asp Thr Leu Arg Lys Val Leu Val Glu
            115                 120                 125

Val Leu Ala Asp Pro Leu Asp His Arg Asp Ala Gly Asp Leu Trp Phe
        130                 135                 140

Pro Gly Glu Ser Glu Ser Phe Glu Asp Ala His Val Glu His Ser Ile
145                 150                 155                 160

Ser Arg Gly Gly Gly Gly Ser Gly Gly Gly Gly Ser Gly Gly Gly Gly
                165                 170                 175

Ser Asp Lys Thr His Thr Cys Pro Pro Cys Pro Ala Pro Glu Leu Leu
                180                 185                 190

Gly Gly Pro Ser Val Phe Leu Phe Pro Pro Lys Pro Lys Asp Thr Leu
            195                 200                 205

Met Ile Ser Arg Thr Pro Glu Val Thr Cys Val Val Val Asp Val Ser
        210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Gln Ser Thr
                245                 250                 255

Tyr Arg Val Val Ser Val Leu Thr Val Leu His Gln Asp Trp Leu Asn
                260                 265                 270

Gly Lys Glu Tyr Lys Cys Lys Val Ser Asn Lys Ala Leu Pro Ala Pro
            275                 280                 285
```

```
Ile Glu Lys Thr Ile Ser Lys Ala Lys Gly Gln Pro Arg Glu Pro Gln
290                 295                 300

Val Tyr Thr Leu Pro Pro Ser Arg Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
                340                 345                 350

Pro Val Leu Asp Ser Asp Gly Ser Phe Phe Leu Tyr Ser Lys Leu Thr
                355                 360                 365

Val Asp Lys Ser Arg Trp Gln Gln Gly Asn Val Phe Ser Cys Ser Val
370                 375                 380

Met His Glu Ala Leu His Asn His Tyr Thr Gln Lys Ser Leu Ser Leu
385                 390                 395                 400

Ser Pro Gly Lys

<210> SEQ ID NO 41
<211> LENGTH: 413
<212> TYPE: PRT
<213> ORGANISM: Artificial Sequence
<220> FEATURE:
<223> OTHER INFORMATION: Leader- ectodomain of human TREM1- Linker- Fc
      domain of human IgG1(a glycosylation site N297Q mutation)

<400> SEQUENCE: 41

Met Glu Phe Gly Leu Ser Trp Val Phe Leu Val Ala Leu Phe Arg Gly
1               5                   10                  15

Val Gln Ser Ala Thr Lys Leu Thr Glu Lys Tyr Glu Leu Lys Glu
                20                  25                  30

Gly Gln Thr Leu Asp Val Lys Cys Asp Tyr Thr Leu Glu Lys Phe Ala
                35                  40                  45

Ser Ser Gln Lys Ala Trp Gln Ile Ile Arg Asp Gly Glu Met Pro Lys
50                  55                  60

Thr Leu Ala Cys Thr Glu Arg Pro Ser Lys Asn Ser His Pro Val Gln
65                  70                  75                  80

Val Gly Arg Ile Ile Leu Glu Asp Tyr His Asp His Gly Leu Leu Arg
                85                  90                  95

Val Arg Met Val Asn Leu Gln Val Glu Asp Ser Gly Leu Tyr Gln Cys
                100                 105                 110

Val Ile Tyr Gln Pro Pro Lys Glu Pro His Met Leu Phe Asp Arg Ile
                115                 120                 125

Arg Leu Val Val Thr Lys Gly Phe Ser Gly Thr Pro Gly Ser Asn Glu
130                 135                 140

Asn Ser Thr Gln Asn Val Tyr Lys Ile Pro Pro Thr Thr Thr Lys Ala
145                 150                 155                 160

Leu Cys Pro Leu Tyr Thr Ser Pro Arg Thr Val Gly Gly Gly Ser
                165                 170                 175

Gly Gly Gly Gly Ser Gly Gly Gly Ser Asp Lys Thr His Thr Cys
                180                 185                 190

Pro Pro Cys Pro Ala Pro Glu Leu Leu Gly Gly Pro Ser Val Phe Leu
                195                 200                 205

Phe Pro Pro Lys Pro Lys Asp Thr Leu Met Ile Ser Arg Thr Pro Glu
                210                 215                 220

Val Thr Cys Val Val Val Asp Val Ser His Glu Asp Pro Glu Val Lys
225                 230                 235                 240
```

```
Phe Asn Trp Tyr Val Asp Gly Val Glu Val His Asn Ala Lys Thr Lys
                245                 250                 255

Pro Arg Glu Glu Gln Tyr Gln Ser Thr Tyr Arg Val Val Ser Val Leu
            260                 265                 270

Thr Val Leu His Gln Asp Trp Leu Asn Gly Lys Glu Tyr Lys Cys Lys
        275                 280                 285

Val Ser Asn Lys Ala Leu Pro Ala Pro Ile Glu Lys Thr Ile Ser Lys
    290                 295                 300

Ala Lys Gly Gln Pro Arg Glu Pro Gln Val Tyr Thr Leu Pro Pro Ser
305                 310                 315                 320

Arg Glu Glu Met Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Val Leu Asp Ser Asp Gly
        355                 360                 365

Ser Phe Phe Leu Tyr Ser Lys Leu Thr Val Asp Lys Ser Arg Trp Gln
    370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys
                405                 410

<210> SEQ ID NO 42
<211> LENGTH: 408
<212> TYPE: PRT
<213> ORGANISM: Artificial Sequence
<220> FEATURE:
<223> OTHER INFORMATION: Leader- ectodomain of human TREML1- Linker- Fc
      domain of human IgG1(a glycosylation site N297Q mutation)

<400> SEQUENCE: 42

Met Glu Phe Gly Leu Ser Trp Val Phe Leu Val Ala Leu Phe Arg Gly
1               5                   10                  15

Val Gln Ser Gln Gly Ile Val Gly Ser Leu Pro Glu Val Leu Gln Ala
            20                  25                  30

Pro Val Gly Ser Ser Ile Leu Val Gln Cys His Tyr Arg Leu Gln Asp
        35                  40                  45

Val Lys Ala Gln Lys Val Trp Cys Arg Phe Leu Pro Glu Gly Cys Gln
    50                  55                  60

Pro Leu Val Ser Ser Ala Val Asp Arg Arg Ala Pro Ala Gly Arg Arg
65                  70                  75                  80

Thr Phe Leu Thr Asp Leu Gly Gly Gly Leu Leu Gln Val Glu Met Val
                85                  90                  95

Thr Leu Gln Glu Glu Asp Ala Gly Glu Tyr Gly Cys Met Val Asp Gly
            100                 105                 110

Ala Arg Gly Pro Gln Ile Leu His Arg Val Ser Leu Asn Ile Leu Pro
        115                 120                 125

Pro Glu Glu Glu Glu Thr His Lys Ile Gly Ser Leu Ala Glu Asn
    130                 135                 140

Ala Phe Ser Asp Pro Ala Gly Ser Ala Asn Pro Leu Glu Pro Ser Gln
145                 150                 155                 160

Asp Glu Lys Ser Ile Pro Gly Gly Gly Ser Gly Gly Gly Gly Ser
                165                 170                 175

Gly Gly Gly Gly Ser Asp Lys Thr His Thr Cys Pro Pro Cys Pro Ala
            180                 185                 190
```

```
Pro Glu Leu Leu Gly Gly Pro Ser Val Phe Leu Phe Pro Pro Lys Pro
            195                 200                 205

Lys Asp Thr Leu Met Ile Ser Arg Thr Pro Glu Val Thr Cys Val Val
        210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
            245                 250                 255

Tyr Gln Ser Thr Tyr Arg Val Val Ser Val Leu Thr Val Leu His Gln
        260                 265                 270

Asp Trp Leu Asn Gly Lys Glu Tyr Lys Cys Lys Val Ser Asn Lys Ala
            275                 280                 285

Leu Pro Ala Pro Ile Glu Lys Thr Ile Ser Lys Ala Lys Gly Gln Pro
        290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
            325                 330                 335

Asp Ile Ala Val Glu Trp Glu Ser Asn Gly Gln Pro Glu Asn Asn Tyr
        340                 345                 350

Lys Thr Thr Pro Pro Val Leu Asp Ser Asp Gly Ser Phe Phe Leu Tyr
            355                 360                 365

Ser Lys Leu Thr Val Asp Lys Ser Arg Trp Gln Gln Gly Asn Val Phe
        370                 375                 380

Ser Cys Ser Val Met His Glu Ala Leu His Asn His Tyr Thr Gln Lys
385                 390                 395                 400

Ser Leu Ser Leu Ser Pro Gly Lys
            405

<210> SEQ ID NO 43
<211> LENGTH: 424
<212> TYPE: PRT
<213> ORGANISM: Artificial Sequence
<220> FEATURE:
<223> OTHER INFORMATION: Leader- ectodomain of human TREML2- Linker- Fc
      domain of human IgG1(a glycosylation site N297Q mutation)

<400> SEQUENCE: 43

Met Glu Phe Gly Leu Ser Trp Val Phe Leu Val Ala Leu Phe Arg Gly
1               5                   10                  15

Val Gln Ser Pro Ser Ala Asp Ser Val Tyr Thr Lys Val Arg Leu Leu
            20                  25                  30

Glu Gly Glu Thr Leu Ser Val Gln Cys Ser Tyr Lys Gly Tyr Lys Asn
        35                  40                  45

Arg Val Glu Gly Lys Val Trp Cys Lys Ile Arg Lys Lys Lys Cys Glu
    50                  55                  60

Pro Gly Phe Ala Arg Val Trp Val Lys Gly Pro Arg Tyr Leu Leu Gln
65                  70                  75                  80

Asp Asp Ala Gln Ala Lys Val Val Asn Ile Thr Met Val Ala Leu Lys
            85                  90                  95

Leu Gln Asp Ser Gly Arg Tyr Trp Cys Met Arg Asn Thr Ser Gly Ile
        100                 105                 110

Leu Tyr Pro Leu Met Gly Phe Gln Leu Asp Val Ser Pro Ala Pro Gln
    115                 120                 125

Thr Glu Arg Asn Ile Pro Phe Thr His Leu Asp Asn Ile Leu Lys Ser
```

```
            130                 135                 140
Gly Thr Val Thr Thr Gly Gln Ala Pro Thr Ser Gly Pro Asp Ala Pro
145                 150                 155                 160

Phe Thr Thr Gly Val Met Val Phe Thr Pro Gly Leu Ile Thr Leu Pro
                165                 170                 175

Arg Leu Leu Ala Ser Thr Gly Gly Gly Ser Gly Gly Gly Gly Ser
            180                 185                 190

Gly Gly Gly Gly Ser Asp Lys Thr His Thr Cys Pro Pro Cys Pro Ala
        195                 200                 205

Pro Glu Leu Leu Gly Gly Pro Ser Val Phe Leu Phe Pro Pro Lys Pro
    210                 215                 220

Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
                245                 250                 255

Asp Gly Val Glu Val His Asn Ala Lys Thr Lys Pro Arg Glu Glu Gln
            260                 265                 270

Tyr Gln Ser Thr Tyr Arg Val Val Ser Val Leu Thr Val Leu His Gln
        275                 280                 285

Asp Trp Leu Asn Gly Lys Glu Tyr Lys Cys Lys Val Ser Asn Lys Ala
    290                 295                 300

Leu Pro Ala Pro Ile Glu Lys Thr Ile Ser Lys Ala Lys Gly Gln Pro
305                 310                 315                 320

Arg Glu Pro Gln Val Tyr Thr Leu Pro Pro Ser Arg Glu Glu Met Thr
                325                 330                 335

Lys Asn Gln Val Ser Leu Thr Cys Leu Val Lys Gly Phe Tyr Pro Ser
            340                 345                 350

Asp Ile Ala Val Glu Trp Glu Ser Asn Gly Gln Pro Glu Asn Asn Tyr
        355                 360                 365

Lys Thr Thr Pro Pro Val Leu Asp Ser Asp Gly Ser Phe Phe Leu Tyr
    370                 375                 380

Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
                405                 410                 415

Ser Leu Ser Leu Ser Pro Gly Lys
            420

<210> SEQ ID NO 44
<211> LENGTH: 200
<212> TYPE: PRT
<213> ORGANISM: Artificial Sequence
<220> FEATURE:
<223> OTHER INFORMATION: full-length wild-type human TREML4

<400> SEQUENCE: 44

Met Ala Trp Gly Gly Val His Thr Cys Cys Phe His Leu Cys Cys Cys
1               5                   10                  15

Cys Ser Trp Pro Gln Gly Ala Val Pro Glu Glu Leu His Lys His Pro
            20                  25                  30

Gly Gln Thr Leu Leu Gln Cys Gln Tyr Ser Pro Lys Arg Gly Pro
        35                  40                  45

Tyr Gln Pro Lys Ser Trp Cys Gln Gln Thr Ser Pro Ser Arg Cys Thr
    50                  55                  60

Leu Leu Val Thr Ser Ser Lys Pro Trp Thr Ala Val Gln Lys Ser His
```

```
                65                  70                  75                  80
Tyr Thr Ile Trp Asp Lys Pro Asn Ala Gly Phe Phe Asn Ile Thr Met
                85                  90                  95

Ile Gln Leu Thr Gln Asn Asp Ser Gly Phe Tyr Trp Cys Gly Ile Tyr
                100                 105                 110

Asn Ala Ser Glu Asn Ile Ile Thr Val Leu Arg Asn Ile Ser Leu Val
                115                 120                 125

Val Ser Pro Ala Pro Thr Thr Ser Pro Met Trp Thr Leu Pro Trp Leu
            130                 135                 140

Pro Thr Ser Thr Val Leu Ile Thr Ser Pro Glu Gly Thr Ser Gly His
145                 150                 155                 160

Pro Ser Ile Asn Gly Ser Glu Thr Arg Lys Ser Arg Ala Pro Ala Cys
                165                 170                 175

Leu Gly Ser Gly Gly Pro Arg Phe Leu Val Leu Val Leu Cys Gly Leu
                180                 185                 190

Leu Leu Ala Lys Gly Leu Met Leu
                195                 200

<210> SEQ ID NO 45
<211> LENGTH: 143
<212> TYPE: PRT
<213> ORGANISM: Artificial Sequence
<220> FEATURE:
<223> OTHER INFORMATION: hTREM2

<400> SEQUENCE: 45

His Asn Thr Thr Val Phe Gln Gly Val Ala Gly Gln Ser Leu Gln Val
1               5                   10                  15

Ser Cys Pro Tyr Asp Ser Met Lys His Trp Gly Arg Arg Lys Ala Trp
                20                  25                  30

Cys Arg Gln Leu Gly Glu Lys Gly Pro Cys Gln Arg Val Val Ser Thr
            35                  40                  45

His Asn Leu Trp Leu Leu Ser Phe Leu Arg Arg Trp Asn Gly Ser Thr
        50                  55                  60

Ala Ile Thr Asp Asp Thr Leu Gly Gly Thr Leu Thr Ile Thr Leu Arg
65                  70                  75                  80

Asn Leu Gln Pro His Asp Ala Gly Leu Tyr Gln Cys Gln Ser Leu His
                85                  90                  95

Gly Ser Glu Ala Asp Thr Leu Arg Lys Val Leu Val Glu Val Leu Ala
                100                 105                 110

Asp Pro Leu Asp His Arg Asp Ala Gly Asp Leu Trp Phe Pro Gly Glu
            115                 120                 125

Ser Glu Ser Phe Glu Asp Ala His Val Glu His Ser Ile Ser Arg
        130                 135                 140

<210> SEQ ID NO 46
<211> LENGTH: 164
<212> TYPE: PRT
<213> ORGANISM: Artificial Sequence
<220> FEATURE:
<223> OTHER INFORMATION: mTREML4

<400> SEQUENCE: 46

Glu Glu Leu His Arg Met Val Gly Gln Ser Leu Ser Val Gln Cys Gln
1               5                   10                  15

Tyr Lys Pro Lys Glu Glu Ser Tyr Val Leu Lys Thr Trp Cys Arg Gln
                20                  25                  30
```

```
Thr Ala Pro Ser Lys Cys Thr Arg Val Val Thr Thr Ser Glu Pro Arg
        35                  40                  45

Lys Ala Ala Arg Glu Leu Gln His Thr Ile Trp Asp Asp Pro Glu Ala
    50                  55                  60

Gly Phe Phe Asn Ile Thr Met Thr Gln Leu Thr Glu Asp Asp Ser Ala
65                  70                  75                  80

Phe Tyr Trp Cys Gly Pro Tyr Pro Ser Leu Arg Glu Val Thr Val
                85                  90                  95

Leu Arg Asn Ile Ser Leu Val Val Ser Pro Ala Pro Ser Thr Leu Pro
                100                 105                 110

Ser Gln Thr Ile Ala Pro Leu Pro Glu Ser Thr Ala Thr Ile Phe Met
        115                 120                 125

Pro Phe Pro Val Leu Thr Thr Ser Pro Glu Glu Thr Thr Asp Ser Ser
        130                 135                 140

Ile Asn Gly Thr Gly His Arg Asn Gln Ser Ser Ser Ser Pro Gly Trp
145                 150                 155                 160

Thr Ser Pro Gly

<210> SEQ ID NO 47
<211> LENGTH: 150
<212> TYPE: PRT
<213> ORGANISM: Artificial Sequence
<220> FEATURE:
<223> OTHER INFORMATION: hTREML4

<400> SEQUENCE: 47

Glu Glu Leu His Lys His Pro Gly Gln Thr Leu Leu Leu Gln Cys Gln
1               5                   10                  15

Tyr Ser Pro Lys Arg Gly Pro Tyr Gln Pro Lys Ser Trp Cys Gln Gln
                20                  25                  30

Thr Ser Pro Ser Arg Cys Thr Leu Leu Val Thr Ser Ser Lys Pro Trp
            35                  40                  45

Thr Ala Val Gln Lys Ser His Tyr Thr Ile Trp Asp Lys Pro Asn Ala
    50                  55                  60

Gly Phe Phe Asn Ile Thr Met Ile Gln Leu Thr Gln Asn Asp Ser Gly
65                  70                  75                  80

Phe Tyr Trp Cys Gly Ile Tyr Asn Ala Ser Glu Asn Ile Ile Thr Val
                85                  90                  95

Leu Arg Asn Ile Ser Leu Val Val Ser Pro Ala Pro Thr Thr Ser Pro
                100                 105                 110

Met Trp Thr Leu Pro Trp Leu Pro Thr Ser Thr Val Leu Ile Thr Ser
        115                 120                 125

Pro Glu Gly Thr Ser Gly His Pro Ser Ile Asn Gly Ser Glu Thr Arg
        130                 135                 140

Lys Ser Arg Ala Pro Ala
145                 150
```

COMPOSITIONS FOR MODULATION OF A TREM OR TREML PROTEIN AND METHODS OF USE

CROSS REFERENCE TO RELATED APPLICATIONS

This application is a U.S. national phase application filed under 35 U.S.C. § 371 claiming benefit to International Patent Application No. PCT/US2019/018044, filed Feb. 14, 2019, which is entitled to priority under 35 U.S.C. § 119(e) to U.S. Provisional Application No. 62/630,333, filed Feb. 14, 2018 and U.S. Provisional Application No. 62/771,730, filed Nov. 27, 2018, each of which applications is hereby incorporated herein by reference in its entirety.

BACKGROUND OF THE INVENTION

Inflammation and inflammation-associated organ damage are final common end pathways in many prevalent human diseases with unmet needs, including autoimmune diseases, autoinflammatory diseases, coronary and peripheral vascular diseases and other complications of metabolic syndrome, neurodegenerative and neuropsychiatric syndromes, as well as sepsis, the prototypic infection-associated inflammatory disorder. Sepsis is a maladaptive condition that occurs when the immune response to a serious infection causes catastrophic changes in hemodynamics, leading to hypotension, hypoxemia, organ failure, and death. Despite being a leading cause of death worldwide, there are no effective interventions for sepsis beyond early administration of antibiotics and supportive care. Dozens of clinical agents have been proposed and clinically evaluated in sepsis, ranging from agents that sequester bacterial products (e.g., anti-LPS antibodies) to inhibitors of inflammatory cytokines (e.g., anti-TNF-alpha antibodies and interleukin-1 antagonists). However, none of these agents were found to provide a significant benefit in patients.

Thus, there remains a need in the art for improved treatments for sepsis, and other conditions characterized by elevated inflammation, including autoimmune diseases and disorders. The present invention addresses this unmet need.

SUMMARY OF THE INVENTION

In one aspect, the present invention provides a composition for reducing inflammation in a subject, comprising a protein comprising an ectodomain of Triggering Receptor Expressed on Myeloid cells (TREM)-like 4 (TREML4).

In one embodiment, the ectodomain of TREML4 comprises the amino acid sequence selected from the group consisting of: SEQ ID NO: 1, an amino acid sequence that is at least 90% homologous to SEQ ID NO: 1, SEQ ID NO: 14, and an amino acid sequence that is at least 90% homologous to SEQ ID NO: 14.

In one embodiment, the ectodomain of TREML4 comprises one or more mutations that confer binding of the ectodomain to a necrotic cell or necroptotic cell. In one embodiment, the one or more mutations are at one or more residues selected from the group consisting of T35, L65, L66, S69, K71, K78, K86, T95, G156, and H160, relative to full-length human TREML4.

In one embodiment, the ectodomain of TREML4 comprises the amino acid sequence selected from the group consisting of: SEQ ID NO: 2, an amino acid sequence that is at least 90% homologous to SEQ ID NO: 2, SEQ ID NO: 3, an amino acid sequence that is at least 90% homologous to SEQ ID NO: 3, SEQ ID NO: 4, an amino acid sequence that is at least 90% homologous to SEQ ID NO: 4, SEQ ID NO: 5, an amino acid sequence that is at least 90% homologous to SEQ ID NO: 5, SEQ ID NO: 6, an amino acid sequence that is at least 90% homologous to SEQ ID NO: 6, SEQ ID NO: 7, an amino acid sequence that is at least 90% homologous to SEQ ID NO: 7, SEQ ID NO: 8, an amino acid sequence that is at least 90% homologous to SEQ ID NO: 8, SEQ ID NO: 9, an amino acid sequence that is at least 90% homologous to SEQ ID NO: 9, SEQ ID NO: 10, an amino acid sequence that is at least 90% homologous to SEQ ID NO: 10, SEQ ID NO: 11, an amino acid sequence that is at least 90% homologous to SEQ ID NO: 11, SEQ ID NO: 12, an amino acid sequence that is at least 90% homologous to SEQ ID NO: 12, SEQ ID NO: 13, and an amino acid sequence that is at least 90% homologous to SEQ ID NO: 13.

In one embodiment, the protein comprises a first domain and a second domain; wherein the first domain comprises the ectodomain of TREML4; and wherein the second domain comprises at least one region of an immunoglobulin. In one embodiment, the second domain comprises an Fc domain of an immunoglobulin. In one embodiment, the second domain comprises the Fc domain of human IgG1. In one embodiment, the second domain comprises an Fc domain of an immunoglobulin that comprises one or more mutations to remove Fc effector function through Fc receptors or complement. In one embodiment, the second domain comprises an Fc domain of human IgG1 comprising a mutation at residue N297, relative to wildtype human IgG1, rendering the Fc domain aglycosylated. In one embodiment, the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22.

In one embodiment, the protein comprises an amino acid sequence selected from the group consisting of: SEQ ID NO: 26, an amino acid sequence that is at least 90% homologous to SEQ ID NO: 26, SEQ ID NO: 27, an amino acid sequence that is at least 90% homologous to SEQ ID NO: 27, SEQ ID NO: 28, an amino acid sequence that is at least 90% homologous to SEQ ID NO: 28, SEQ ID NO: 29, an amino acid sequence that is at least 90% homologous to SEQ ID NO: 29, SEQ ID NO: 30, an amino acid sequence that is at least 90% homologous to SEQ ID NO: 30, SEQ ID NO: 31, an amino acid sequence that is at least 90% homologous to SEQ ID NO: 31, SEQ ID NO: 32, an amino acid sequence that is at least 90% homologous to SEQ ID NO: 32, SEQ ID NO: 33, an amino acid sequence that is at least 90% homologous to SEQ ID NO: 33, SEQ ID NO: 34, an amino acid sequence that is at least 90% homologous to SEQ ID NO: 34, SEQ ID NO: 35, an amino acid sequence that is at least 90% homologous to SEQ ID NO: 35, SEQ ID NO: 36, an amino acid sequence that is at least 90% homologous to SEQ ID NO: 36, SEQ ID NO: 37, an amino acid sequence that is at least 90% homologous to SEQ ID NO: 37, SEQ ID NO: 38, an amino acid sequence that is at least 90% homologous to SEQ ID NO: 38, SEQ ID NO: 39, and an amino acid sequence that is at least 90% homologous to SEQ ID NO: 39.

In one aspect, the present invention provides an isolated nucleic acid molecule comprising a nucleotide sequence encoding a protein comprising an ectodomain of TREML4.

In one aspect, the present invention provides a composition for reducing inflammation in a subject, comprising a protein comprising a first domain and a second domain, wherein the first domain comprises an ectodomain of Triggering Receptor Expressed on Myeloid cells 2 (TREM2); and wherein the second domain comprises an Fc domain of an immunoglobulin that comprises one or more mutations to remove Fc effector function through Fc receptors or complement.

In one embodiment, the second domain comprises an Fc domain of human IgG1 comprising a mutation at residue N297, relative to wildtype human IgG1, rendering the Fc domain aglycosylated.

In one embodiment, the ectodomain of TREM2 comprises the amino acid sequence selected from the group consisting of: SEQ ID NO: 15, and an amino acid sequence that is at least 90% homologous to SEQ ID NO: 15. In one embodiment, the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22.

In one embodiment, the protein comprises an amino acid sequence selected from the group consisting of SEQ ID NO: 40, and an amino acid sequence that is at least 90% homologous to SEQ ID NO: 40.

In one aspect, the present invention provides an isolated nucleic acid molecule comprising a nucleotide sequence encoding a protein comprising a first domain and a second domain, wherein the first domain comprises TREM2; and wherein the second domain comprises an Fc domain of an immunoglobulin comprising one or more mutations to reduce Fc effector function.

In one aspect, the present invention provides a method of reducing inflammation in a subject, comprising administering to the subject a protein comprising an ectodomain of TREML4. In one embodiment, the ectodomain of TREML4 comprises the amino acid sequence selected from the group consisting of: SEQ ID NO: 1, an amino acid sequence that is at least 90% homologous to SEQ ID NO: 1, SEQ ID NO: 14, and an amino acid sequence that is at least 90% homologous to SEQ ID NO: 14. In one embodiment, the protein comprises a first domain and a second domain; wherein the first domain comprises the ectodomain of TREML4; and wherein the second domain comprises at least one region of an immunoglobulin.

In one embodiment, the ectodomain of TREML4 comprises one or more mutations that confer binding of the ectodomain to a necrotic cell or necroptotic cell. In one embodiment, the one or more mutations are selected from the group consisting of T35, L65, L66, S69, K71, K78, K86, T95, G156, and H160, relative to full-length human TREML4.

In one embodiment, the ectodomain of TREML4 comprises the amino acid sequence selected from the group consisting of: SEQ ID NO: 2, an amino acid sequence that is at least 90% homologous to SEQ ID NO: 2, SEQ ID NO: 3, an amino acid sequence that is at least 90% homologous to SEQ ID NO: 3, SEQ ID NO: 4, an amino acid sequence that is at least 90% homologous to SEQ ID NO: 4, SEQ ID NO: 5, an amino acid sequence that is at least 90% homologous to SEQ ID NO: 5, SEQ ID NO: 6, an amino acid sequence that is at least 90% homologous to SEQ ID NO: 6, SEQ ID NO: 7, an amino acid sequence that is at least 90% homologous to SEQ ID NO: 7, SEQ ID NO: 8, an amino acid sequence that is at least 90% homologous to SEQ ID NO: 8, SEQ ID NO: 9, an amino acid sequence that is at least 90% homologous to SEQ ID NO: 9, SEQ ID NO: 10, an amino acid sequence that is at least 90% homologous to SEQ ID NO: 10, SEQ ID NO: 11, an amino acid sequence that is at least 90% homologous to SEQ ID NO: 11, SEQ ID NO: 12, an amino acid sequence that is at least 90% homologous to SEQ ID NO: 12, SEQ ID NO: 13, and an amino acid sequence that is at least 90% homologous to SEQ ID NO: 13.

In one embodiment, the second domain comprises an Fc domain of an immunoglobulin. In one embodiment, the second domain comprises the Fc domain of human IgG1. In one embodiment, the second domain comprises an Fc domain of an immunoglobulin that comprises one or more mutations to remove Fc effector function through Fc receptors or complement. In one embodiment, the second domain comprises an Fc domain of human IgG1 comprising a mutation at residue N297, relative to wildtype human IgG1, rendering the Fc domain aglycosylated. In one embodiment, the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22. In one embodiment, the protein comprises an amino acid sequence selected from the group consisting of SEQ ID NO: 26, an amino acid sequence that is at least 90% homologous to SEQ ID NO: 26, SEQ ID NO: 27, an amino acid sequence that is at least 90% homologous to SEQ ID NO: 27, SEQ ID NO: 28, an amino acid sequence that is at least 90% homologous to SEQ ID NO: 28, SEQ ID NO: 29, an amino acid sequence that is at least 90% homologous to SEQ ID NO: 29, SEQ ID NO: 30, an amino acid sequence that is at least 90% homologous to SEQ ID NO: 30, SEQ ID NO: 31, an amino acid sequence that is at least 90% homologous to SEQ ID NO: 31, SEQ ID NO: 32, an amino acid sequence that is at least 90% homologous to SEQ ID NO: 32, SEQ ID NO: 33, an amino acid sequence that is at least 90% homologous to SEQ ID NO: 33, SEQ ID NO: 34, an amino acid sequence that is at least 90% homologous to SEQ ID NO: 34, SEQ ID NO: 35, an amino acid sequence that is at least 90% homologous to SEQ ID NO: 35, SEQ ID NO: 36, an amino acid sequence that is at least 90% homologous to SEQ ID NO: 36, SEQ ID NO: 37, an amino acid sequence that is at least 90% homologous to SEQ ID NO: 37, SEQ ID NO: 38, an amino acid sequence that is at least 90% homologous to SEQ ID NO: 38, SEQ ID NO: 39, and an amino acid sequence that is at least 90% homologous to SEQ ID NO: 39.

In one embodiment, the subject has an inflammatory, autoinflammatory, or autoimmune disease or disorder. In one embodiment, the subject is at risk for developing an inflammatory, autoinflammatory, or autoimmune disease or disorder.

In one embodiment, the prevent invention provides a method for reducing inflammation in a subject, comprising administering to the subject a protein comprising a first domain and a second domain, wherein the first domain comprises an ectodomain of TREM2; and wherein the second domain comprises an Fc domain of an immunoglobulin that comprises one or more mutations to remove Fc effector function through Fc receptors or complement. In one embodiment, the second domain comprises an Fc domain of human IgG1 comprising a mutation at residue N297, relative to wildtype human IgG1, rendering the Fc domain aglycosylated.

In one embodiment, the ectodomain of TREM2 comprises the amino acid sequence selected from the group consisting of: SEQ ID NO: 15, and an amino acid sequence that is at least 90% homologous to SEQ ID NO: 15. In one embodiment, the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22. In one embodiment, the protein comprises an amino acid sequence selected from the group consisting of SEQ ID NO: 40, and an amino acid sequence that is at least 90% homologous to SEQ ID NO: 40.

In one embodiment, the subject has an inflammatory, autoinflammatory, or autoimmune disease or disorder. In one embodiment, the subject is at risk for developing an inflammatory, autoinflammatory, or autoimmune disease or disorder.

In one aspect, the present invention provides a composition for reducing inflammation comprising an inhibitor of the interaction between (a) a TREM or TREML protein and (b) one selected from the group consisting of: mitochondria derived or released from necroptotic cells and cardiolipin. In one embodiment, the inhibitor is selected from the group consisting of: a small molecule, antibody, antibody fragment, protein, and peptidomimetic.

In one aspect, the present invention provides a method for reducing inflammation in a subject, comprising administering to the subject a composition comprising an of the interaction between (a) a TREM or TREML protein and (b) one selected from the group consisting of: mitochondria derived or released from necroptotic cells and cardiolipin. In one embodiment, the inhibitor is selected from the group consisting of: a small molecule, antibody, antibody fragment, protein, and peptidomimetic. In one embodiment, the subject has an inflammatory, autoinflammatory, or autoimmune disease or disorder. In one embodiment, the subject is at risk for developing an inflammatory, autoinflammatory, or autoimmune disease or disorder.

In one aspect, the present invention provides a method comprising obtaining a sample of subject; detecting the level of at least one biomarker in the sample, wherein the at least one biomarker is selected from the group consisting of: mitochondria derived or released from necroptotic cells and cardiolipin; and detecting that the level of the at least one biomarker is increased as compared to the level of the at least one biomarker in a control group or control sample.

In one embodiment, the method further comprises administering to the subject a treatment for an inflammatory, autoinflammatory, or autoimmune disorder. In one embodiment, the method comprises administering to the subject a composition comprising a protein comprising an ectodomain of TREML4, or variant thereof. In one embodiment, the method comprises administering to the subject a composition comprising a protein comprising a first domain and a second domain, wherein the first domain comprises an ectodomain of TREM2 or variant thereof; and wherein the second domain comprises an Fc domain of an immunoglobulin that comprises one or more mutations to remove Fc effector function through Fc receptors or complement. In one embodiment, the second domain comprises an Fc domain of human IgG1 comprising a mutation at residue N297, relative to wildtype human IgG1, rendering the Fc domain aglycosylated. In one embodiment, the method comprises administering to the subject a composition comprising an inhibitor of (a) the interaction between a TREM or TREML protein and mitochondria derived or released from necroptotic cells and cardiolipin; or (b) the interaction between a TREM or TREML protein and cardiolipin.

In one aspect, the present invention provides a composition for detecting a necroptotic cell, wherein the composition comprises comprising an ectodomain of TREML4, or a variant thereof, and a detectable label. In one embodiment, the ectodomain of TREML4 comprises the amino acid sequence selected from the group consisting of: SEQ ID NO: 1, an amino acid sequence that is at least 90% homologous to SEQ ID NO: 1, SEQ ID NO: 14, and an amino acid sequence that is at least 90% homologous to SEQ ID NO: 14.

In one embodiment, the ectodomain of TREML4 comprises one or more mutations that confer binding of the ectodomain to a necrotic cell or necroptotic cell. In one embodiment, the one or more mutations are selected from the group consisting of T35, L65, L66, S69, K71, K78, K86, T95, G156, and H160, relative to full-length human TREML4. In one embodiment, the ectodomain of TREML4 comprises the amino acid sequence selected from the group consisting of: SEQ ID NO: 2, an amino acid sequence that is at least 90% homologous to SEQ ID NO: 2, SEQ ID NO: 3, an amino acid sequence that is at least 90% homologous to SEQ ID NO: 3, SEQ ID NO: 4, an amino acid sequence that is at least 90% homologous to SEQ ID NO: 4, SEQ ID NO: 5, an amino acid sequence that is at least 90% homologous to SEQ ID NO: 5, SEQ ID NO: 6, an amino acid sequence that is at least 90% homologous to SEQ ID NO: 6, SEQ ID NO: 7, an amino acid sequence that is at least 90% homologous to SEQ ID NO: 7, SEQ ID NO: 8, an amino acid sequence that is at least 90% homologous to SEQ ID NO: 8, SEQ ID NO: 9, an amino acid sequence that is at least 90% homologous to SEQ ID NO: 9, SEQ ID NO: 10, an amino acid sequence that is at least 90% homologous to SEQ ID NO: 10, SEQ ID NO: 11, an amino acid sequence that is at least 90% homologous to SEQ ID NO: 11, SEQ ID NO: 12, an amino acid sequence that is at least 90% homologous to SEQ ID NO: 12, SEQ ID NO: 13, and an amino acid sequence that is at least 90% homologous to SEQ ID NO: 13.

In one embodiment, the protein comprises a first domain and a second domain; wherein the first domain comprises the ectodomain of TREML4; and wherein the second domain comprises at least one region of an immunoglobulin. In one embodiment, the second domain comprises an Fc domain of an immunoglobulin. In one embodiment, the second domain comprises the Fc domain of human IgG1. In one embodiment, the second domain comprises an Fc domain of an immunoglobulin that comprises one or more mutations to remove Fc effector function through Fc receptors or complement. In one embodiment, the second domain comprises an Fc domain of human IgG1 comprising a mutation at residue N297, relative to wildtype human IgG1, rendering the Fc domain aglycosylated. In one embodiment, the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22.

In one embodiment, the protein comprises an amino acid sequence selected from the group consisting of: SEQ ID NO: 26, an amino acid sequence that is at least 90% homologous to SEQ ID NO: 26, SEQ ID NO: 27, an amino acid sequence that is at least 90% homologous to SEQ ID NO: 27, SEQ ID NO: 28, an amino acid sequence that is at least 90% homologous to SEQ ID NO: 28, SEQ ID NO: 29, an amino acid sequence that is at least 90% homologous to SEQ ID NO: 29, SEQ ID NO: 30, an amino acid sequence that is at least 90% homologous to SEQ ID NO: 30, SEQ ID NO: 31, an amino acid sequence that is at least 90% homologous to SEQ ID NO: 31, SEQ ID NO: 32, an amino acid sequence that is at least 90% homologous to SEQ ID NO: 32, SEQ ID NO: 33, an amino acid sequence that is at least 90% homologous to SEQ ID NO: 33, SEQ ID NO: 34, an amino acid sequence that is at least 90% homologous to SEQ ID NO: 34, SEQ ID NO: 35, an amino acid sequence that is at least 90% homologous to SEQ ID NO: 35, SEQ ID NO: 36, an amino acid sequence that is at least 90% homologous to SEQ ID NO: 36, SEQ ID NO: 37, an amino acid sequence that is at least 90% homologous to SEQ ID NO: 37, SEQ ID NO: 38, an amino acid sequence that is at least 90% homologous to SEQ ID NO: 38, SEQ ID NO: 39, and an amino acid sequence that is at least 90% homologous to SEQ ID NO: 39. In one embodiment, the detectable label comprises a fluorescent molecule, stable metal isotope, or oligonucleotide.

In one aspect, the present invention provides a composition for detecting a necroptotic cell, wherein the composition comprises a protein comprising a first domain and a second domain, wherein the first domain comprises an ectodomain of TREM2 or variant thereof; wherein the second domain comprises an Fc domain of an immunoglobulin that comprises one or more mutations to remove Fc effector function through Fc receptors or complement and wherein the composition further comprises a detectable label. In one embodiment, the second domain comprises an Fc domain of human IgG1 comprising a mutation at residue N297, relative to wildtype human IgG1, rendering the Fc domain aglycosylated.

In one embodiment, the ectodomain of TREM2 comprises the amino acid sequence selected from the group consisting of: SEQ ID NO: 15, and an amino acid sequence that is at least 90% homologous to SEQ ID NO: 15. In one embodiment, the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22. In one embodiment, the protein comprises an amino acid sequence selected from the group consisting of SEQ ID NO: 40, and an amino acid sequence that is at least 90% homologous to SEQ ID NO: 40. In one embodiment, the detectable label comprises a fluorescent molecule, stable metal isotope, or oligonucleotide.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 2 depicts results from example experiments, demonstrating the determination of the therapeutic activity of different dosages of mTREML4-Fc protein in mediating protection from lipopolysaccharide (LPS) sepsis. The Fc variant was aglycosylated human IgG1 with the N297Q mutation. The data demonstrates that mTREML4-Fc protein protects mice from LPS induced endotoxemia. Two hours after i.p LPS injection, mice received 1 mg/kg or 10 mg/kg of mTREML4-Fc protein in experiment #1 or received 5 mg/kg of mTREML4-Fc in experiment #2 by retro orbital injection. Blood glucose and body temperature were measured and recorded. Survival were monitored in every 24 hours for 5 days and analyzed with Mantel-Haenzel Log Rank test.

FIG. 6 depicts the protein sequence alignment of hTREML4 with mTREML4 and hTREM2. Alzheimer Disease (AD) associated positions in hTREM2 are highlighted. hTREML4 has mutations in these critical positions that differ from mTREML4 and hTREM2 and resemble those seen in TREM2 in AD.

FIG. 13A and FIG. 13B, depicts results from the example experiments assessing the ability of mTREML4-Fc, hTREML4-Fc, and hTREML4-K86D-Fc to rescue mice from experimental sepsis due to LPS administration and cecal ligation and puncture (CLP). Mice were randomly grouped and injected with (FIG. 13A) an LD100 dose of LPS or (FIG. 13B) subjected to CLP with 1 cm cecal ligation and 25 G needle puncture. Mice received 10 mg/kg of TREM proteins or isotype control Fc protein (hIgG1 Fc N297Q) intravenously 8 hours after LPS or CLP. Survival was monitored and recorded for 7 days. Survival comparisons were analyzed with the Mantel-Haenzel Log Rank test. The K86D mutation greatly augmented the effectiveness of hTREML4-Fc. The Fc variant used was aglycosylated human IgG1 with the N297Q mutation.

FIG. 19, comprising

FIG. 20, comprising

FIG. 28A and FIG. 28B, depicts the results of example experiments showing that mitochondria accumulate systemically in plasma during sepsis in mice and in patients. (FIG. 28A). Plasma were collected from mice at 24 h post LPS injection or CLP and centrifuged at 12,000 g for 15 min to pellet mitochondria. Mitochondria were stained with Tomm22 Ab and then counted at AccuriC6. (FIG. 28B). Plasma were collected healthy donors and sepsis patients and centrifuged at 12,000 g for 15 min to pellet mitochondria. Mitochondria were stained with Tomm22 Ab and then counted at AccuriC6. These results indicate that measurement of circulating mitochondrial levels in blood could serve as a prospective biomarker to guide the use of TREM-targeting therapeutics such as TREM2-Fc or hTREML4-K86D-Fc.

FIG. 29A, FIG. 29B and FIG. 29C, depicts the results of example experiments showing that TREM2 directly binds the mitochondrial-specific lipid cardiolipin. FIG. 29A summarizes ELISA binding studies showing that hTREM2-Fc, but not control Fc protein binds cardiolipin adsorbed to ELISA plate wells.

FIG. 29B depicts ELISA binding studies showing that hTREML4-K86D but not wildtype hTREML4 binds cardiolipin adsorbed to ELISA plate wells. FIG. 29C depicts the concentration-response relationship of hTREM2, hTREML4 and hTREML4-K86D binding to cardiolipin adsorbed ELISA plate wells.

DETAILED DESCRIPTION

Figure 1:
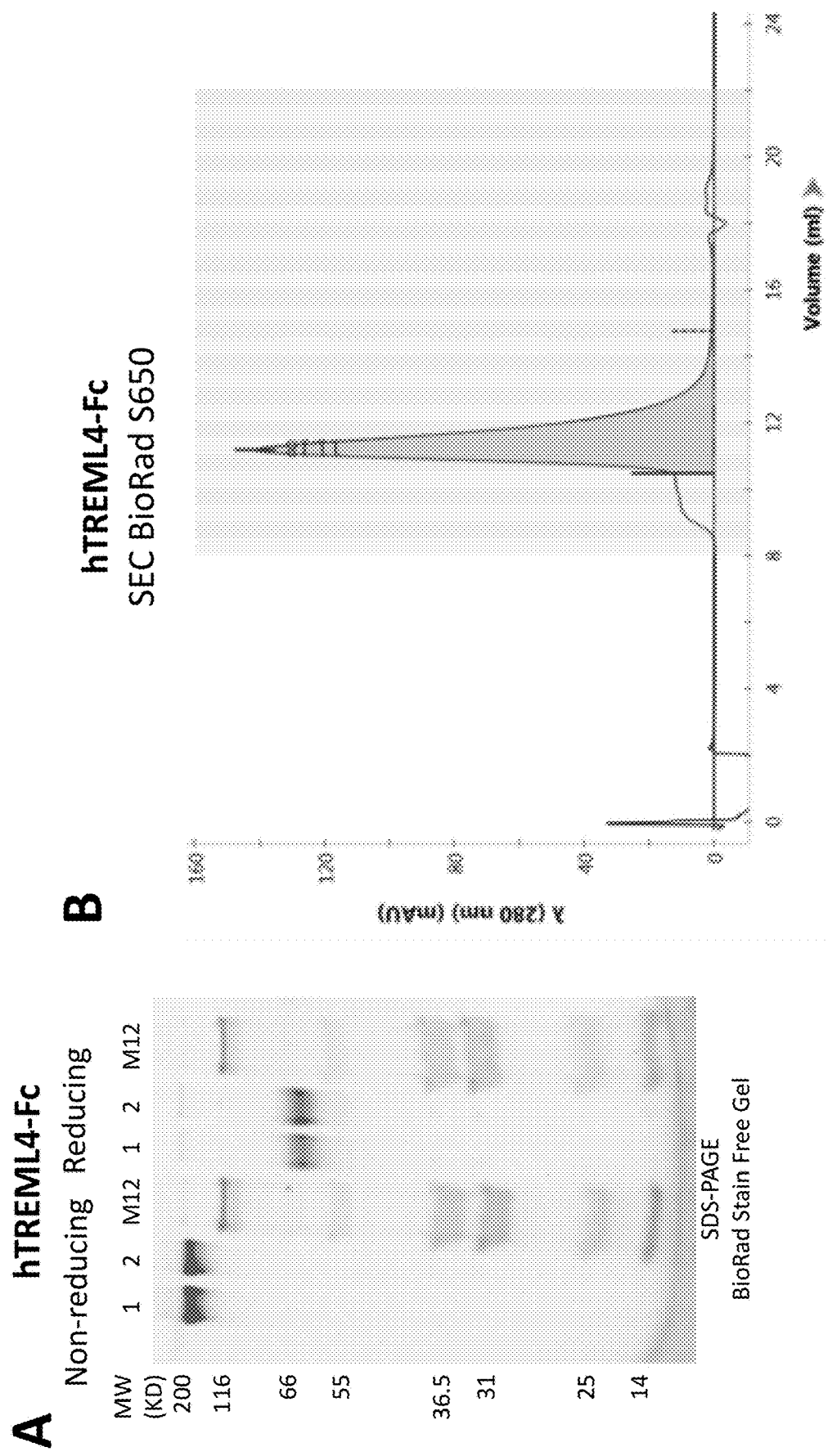
FIG. 1 depicts results from example experiments, demonstrating expression and purification of the TREM ectodomain Fc fusion proteins. The proteins were purified by protein A chromatography (FIG. 1A). Furthermore, analytical size exclusion chromatography showed the majority of the protein was monodisperse and eluted at the expected molecular weight for the dimeric Fc-fusion protein (FIG. 1B).

In one aspect, the present invention provides compositions for the treatment or prevention of an inflammatory, autoinflammatory, or autoimmune diseases or disorders. For example, in certain embodiments, the compositions and methods are based upon inhibition of TREM2 signaling to inhibit, reduce, or prevent inflammation.

During sepsis and other inflammatory disorders, excessive inflammation is sustained by the release of so-called Damage Associated Molecular Patterns (DAMPs) that engage DAMP-receptors on immune cells such as macrophages. Several DAMPs have been described, including, but not limited to extracellular ATP and purine metabolites, extracellular nucleic acid, HMGB1, and the S100 proteins. Some DAMPs have been proposed to be a product of an inflammatory programmed cell necrosis pathway called necroptosis. Necroptosis is driven by high concentrations of inflammatory cytokines such as TNF-alpha and other death receptor pathways that activate RIPK1/RIPK3 signaling such as Fas. It is described herein that released mitochondria from necroptotic cell corpses are a dominant DAMP that are recognized by the receptor TREM2 together with TLR4. Signaling through TREM2/TLR4 promotes inflammatory cytokine production by macrophages and monocytes; pharmacologic blockade of TREM2 reverses sepsis physiology, even at late stages of the disease. Thus, as described herein, the present invention relates to compositions and methods of use of novel TREM receptor antagonists. Furthermore, it is described herein that circulating necroptotic mitochondria are detectable in conditions of inflammation and thus represent a biomarker for TREM and TREML-directed therapeutics.

In certain embodiments, the composition comprises an inhibitor of inhibitor of one or more members of the Triggering Receptor Expressed on Myeloid cells (TREM) family or TREM-like (TREML) family of proteins. For example, in one embodiment, the inhibitor comprises a nucleic acid molecule, a peptide, a polypeptide, a small molecule, an antibody, a peptidomimetic, or the like, which inhibits the activity of at least one TREM or TREML protein. In one embodiment, the inhibitor comprises a peptide that acts as a decoy receptor for at least one TREM or TREML protein, thereby inhibiting the endogenous activity of the TREM or TREML protein. In one embodiment, the protein comprises an ectodomain of at least one TREM or TREML protein, or a variant or fragment thereof.

In some embodiments, the protein is a fusion protein comprising a first domain and a second domain. In one embodiment, the first domain comprises an ectodomain of at least one TREM or TREML protein, or a variant or fragment thereof. In one embodiment, the second domain comprises a peptide that enhances stability or half-life of the fusion protein. For example, in one embodiment, the second domain comprises at least one region of an immunoglobulin, or a variant or fragment thereof. For example, in one embodiment, the second domain comprises an Fc domain of an immunoglobulin.

In one embodiment, the first domain comprises an ectodomain of at least one TREM or TREML protein, or a variant or fragment thereof, and the second domain comprises and Fc domain of an immunoglobulin, or a variant or fragment thereof.

In certain embodiments, the composition comprises an inhibitor that inhibits the interaction between one or more TREM or TREML protein and a mitochondrion, such as a mitochondrion derived or released from a necrotic or necroptotic cell. In one embodiment, the composition comprises an inhibitor that inhibits the interaction between one or more TREM or TREML protein and cardiolipin. In certain embodiments, an inhibitor that inhibits the interaction between one or more TREM or TREML protein and cardiolipin or mitochondria is selected from a nucleic acid molecule, a peptide, a polypeptide, a small molecule, an antibody, an antibody fragment, a peptidomimetic, or the like.

In some embodiments, the present invention provides methods for inhibiting the TREM or TREML signaling pathway in a cell, tissue, or subject. In one embodiment, the method comprises administering to the cell, tissue, or subject, an inhibitor of one or more TREM or TREML protein. In one embodiment, the inhibitor comprises an ectodomain of at least one TREM or TREML protein. In one embodiment, the inhibitor inhibits the interaction between one or more TREM or TREML protein and cardiolipin or mitochondria.

In some embodiments, the present invention provides methods for reducing inflammation in subject by inhibiting one or more TREM or TREML protein in the subject. In one embodiment, the method comprises administering to the cell, tissue, or subject, an inhibitor of one or more TREM or TREML protein. In one embodiment, the inhibitor comprises an ectodomain of at least one TREM or TREML protein. In one embodiment, the inhibitor inhibits the interaction between one or more TREM or TREML protein and cardiolipin or mitochondria.

In some embodiments, the present invention provides methods for treating or preventing an inflammatory, autoinflammatory, or autoimmune disease or disorder in a subject by inhibiting one or more TREM or TREML protein in the subject. In one embodiment, the method comprises administering to the cell, tissue, or subject, an inhibitor of one or more TREM or TREML protein. In one embodiment, the inhibitor comprises an ectodomain of at least one TREM or TREML protein. In one embodiment, the inhibitor inhibits the interaction between one or more TREM or TREML protein and cardiolipin or mitochondria.

In certain embodiments, the present invention provides a method of diagnosing an inflammatory, autoinflammatory, or autoimmune disease or disorder by detecting the presence or amount of cardiolipin or mitochondria, such as mitochondria derived or released from necrotic or necroptotic cells, in a sample, For example, detection of cardiolipin or mitochondria derived or released from necrotic or necroptotic cells can be used to identify a subject as having pro-inflammatory TREM signaling. In some embodiments, detection of cardiolipin or mitochondria derived or released from necrotic or necroptotic cells identifies a subject as a candidate for a treatment or therapy to treat an inflammatory, autoinflammatory, or autoimmune disease or disorder. In one embodiment, detection of cardiolipin or mitochondria derived or released from necrotic or necroptotic cells identifies a subject as a candidate for a treatment with an inhibitor of TREM or TREML signaling described herein, such as an inhibitor that comprises a TREM or TREML ectodomain or an inhibitor that inhibits the interaction between one or more TREM or TREML protein and cardiolipin or mitochondria. In one embodiment, the method comprises detecting the presence or amount of cardiolipin or mitochondria, such as mitochondria derived or released from necrotic or necroptotic cells, in a sample from a subject, and administering to the subject a treatment for an inflammatory, autoinflammatory, or autoimmune disease or disorder. In one embodiment, the method comprises administering to the subject an inhibitor of TREM or TREML signaling, as described herein.

In one aspect, the present invention provides a composition and method for detection of necroptotic cells. For example, in one embodiment, the composition comprises a peptide comprising a TREM or TREML protein, or a variant or fragment thereof. In one embodiment, the peptide comprises the ectodomain on a TREM or TREML protein, or a variant or fragment thereof. In some embodiments, the composition comprises a detectable label, including but not limited to a fluorescent label, DNA barcode, heavy metal, radioactive label, or the like. The composition can be used as reagent for flow cytometry, mass cytometry, CITE-seq, immunofluorescence, or other assay suitable for detection of necroptotic cells.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" of a compound is that amount of compound which is sufficient to provide an effect to the subject or system to which the compound is administered.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In some embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for the inhibition of the TREM or TREML signaling pathways. In some embodiments, the compositions and methods described herein are used to reduce inflammation and treat or prevent inflammatory and autoimmune diseases and disorders. The present invention is based in part on the discovery that inhibitors comprising an ectodomain of a TREM or TREML protein are useful for treating sepsis. For example, it is demonstrated herein that TREM and TREML inhibitors reduce sepsis-mediated mortality.

In certain embodiments, the invention relates to compositions and methods that inhibit the interaction between one or more TREM or TREML protein and cardiolipin or mitochondria. In certain embodiments, the invention relates to compositions comprising a peptide inhibitor comprising a TREM or TREML ectodomain.

Compositions

In one aspect, the present invention provides compositions for modulating TREM or TREML signaling in a subject or biological system. The compositions may be used, for example, to reduce inflammation and to treat or prevent inflammatory, autoinflammatory, or autoimmune diseases or disorders.

In one embodiment, the composition comprises a modulator of one or more TREM or TREML protein. Exemplary TREM proteins include, but are not limited to, TREM1, TREM2, TREM3, TREM4, TREM5, and NCR2 (Nkp44). Exemplary TREML proteins include, but are not limited to TREML1, TREML2, TREML3, TREML4, and TREML6. Further, the present invention encompasses a modulator of TREM or TREML proteins of any species, including, but not limited to human, primate, bovine, canine, mouse, or rat. Further, the present invention encompasses a modulator of any isoform or splice variant of TREM or TREML proteins.

Exemplary modulators of a TREM or TREML protein include, but are not limited to, nucleic acid molecules, vectors, peptides, polypeptides, proteins, antibodies, peptide mimetics, small molecules, and the like.

In some embodiments, the modulator modulates the level or activity of a TREM- or TREML-encoding nucleic acid molecule or TREM or TREML protein by modulating the transcription, translation, splicing, degradation, enzymatic activity, binding activity, or combinations thereof, of a TREM- or TREML-encoding nucleic acid molecule or TREM or TREML protein. In some embodiments, the modulator decreases the expression of a TREM- or TREML-encoding nucleic acid molecule or TREM or TREML protein, thereby decreasing TREM or TREML activity. In some embodiments, the modulator decreases the activity of endogenous TREM- or TREML-encoding nucleic acid molecule or TREM or TREML protein.

In some embodiments, the composition comprises an inhibitor of one or more TREM or TREML proteins. Exemplary inhibitors of a TREM or TREML protein include, but are not limited to, nucleic acid molecules, vectors, peptides, polypeptides, proteins, antibodies, peptide mimetics, small molecules, and the like. In some embodiments, the inhibitor inhibits the expression of one or more TREM- or TREML-encoding nucleic acid molecule or TREM or TREML protein. In some embodiments, the inhibitor inhibits the activity of one or more TREM- or TREML-encoding nucleic acid molecule or TREM or TREML protein. In some embodiments, the inhibitor inhibits the interaction between one or more TREM or TREML protein and cardiolipin or mitochondria. In some embodiments the inhibitor binds to endogenous TREM or TREML protein, thereby inhibiting the activity of the endogenous TREM or TREML protein. In some embodiments, the inhibitor binds the ligand of the endogenous TREM or TREML protein, for instance as a decoy protein or competitive antagonist.

In certain embodiments, the inhibitor comprises a small molecule. For example, in one embodiment, the inhibitor comprises a small molecule that inhibits the interaction between one or more TREM or TREML protein and cardiolipin or mitochondria. When the inhibitor of the invention is a small molecule, a small molecule antagonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In one embodiment, the inhibitor comprises an antibody, or antibody fragment, that inhibits one or more TREM or TREML protein. For example, in one embodiment, the inhibitor comprises an antibody, or antibody fragment, specific for at least one TREM or TREML protein. In one embodiment, the antibody specifically binds to at least one TREM or TREML protein. In one embodiment, the antibody specifically binds to at least one ligand of a TREM or TREML protein. In one embodiment, the antibody specifically binds to cardiolipin or mitochondria. In one embodiment, the antibody inhibits the interaction between one or more TREM or TREML protein and cardiolipin or mitochondria. In one embodiment, the antibody is a polyclonal antibody. In another embodiment, the antibody is a monoclonal antibody. In some embodiments, the antibody is a chimeric antibody. In further embodiments, the antibody is a humanized antibody. In some embodiments, the antibody is an antibody fragment.

In some embodiments, the antibody is an intact monoclonal or polyclonal antibody, or immunologically portion or active fragment thereof. Thus, in various embodiments, the antibody of invention is a polyclonal antibody, monoclonal antibody, intracellular antibody ("intrabody"), Fv, Fab, Fab', F(ab)2 and F(ab')2, single chain antibody (scFv), heavy chain antibody (e.g., such as a camelid antibody), synthetic antibody, chimeric antibody, or humanized antibodies (see, for example, Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426). Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

As will be understood by one skilled in the art, any antibody that can recognize and bind to an antigen of interest is useful in the present invention. Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, NY). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic affinity cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, NY).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least about 70%, 80%, 85%, 86%, 87%, 88%, 89%, 90%, 91%, 92%, 93%, 94%, 95%, 96%, 97%, 98%, or 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

In one embodiment, the composition comprises a protein that inhibits one or more TREM or TREML protein. For example, in some embodiments, the protein inhibitor described herein inhibits the expression or activity of one or more TREM or TREML protein.

For example, in one embodiment, the peptide inhibitor of the invention inhibits at least one TREM or TREML protein by directly by binding to at least one TREM or TREML protein thereby preventing the normal functional activity of at least one TREM or TREML protein. In one embodiment, the peptide inhibitor of the invention inhibits at least one TREM or TREML protein by directly by binding to a ligand of at least one TREM or TREML protein thereby preventing the normal functional activity of at least one TREM or TREML protein. In one embodiment, the peptide inhibitor of the invention inhibits at least one TREM or TREML protein by inhibiting the interaction between one or more TREM or TREML protein and cardiolipin or a mitochondrion. In another embodiment, the peptide inhibitor of the invention inhibits at least one TREM or TREML protein by competing with at least one endogenous TREM or TREML protein. In yet another embodiment, the peptide inhibitor of the invention inhibits the activity of at least one TREM or TREML protein by acting as a transdominant negative mutant.

In one embodiment, the protein inhibitor comprises an ectodomain of a TREM or TREML protein. In some embodiments, the protein inhibitor comprises a fragment or variant of an ectodomain of a TREM or TREML protein. The composition may comprise, for example, an ectodomain from any isoform of a TREM or TREML protein ectodomain, including an ectodomain of a TREM or TREML protein from any organism. In one embodiment, the composition comprises a full-length ectodomain of a TREM or TREML protein. In one embodiment, the composition comprises a recombinant ectodomain of a TREM or TREML protein.

In one embodiment, the protein inhibitor comprises an ectodomain of human TREML4. For example, in one embodiment, the ectodomain of human TREML4 comprises:

```
                                            (SEQ ID NO: 1)
EELHKHPGQTLLLQCQYSPKRGPYQPKSWCQQTSPSRCTLLVTSSKPWT

AVQKSHYTIWDKPNAGFFNITMIQLTQNDSGFYWCGIYNASENIITVLR

NISLVVSPAPTTSPMWTLPWLPTSTVLITSPEGTSGHPSINGSETRKSR

APA,
``` or a variant or fragment thereof.

In some embodiments, the protein inhibitor comprises an ectodomain of human TREML4 comprising one or more mutations. For example, in some embodiments, the protein inhibitor comprises an ectodomain of human TREML4 comprising one or more mutations at one more residues selected from: T35, L65, L66, S69, K71, K78, K86, T95, G156, and H160, in relation to full-length wild-type human TREML4. In one embodiment, full-length wild-type human TREML4, including its native signal peptide, comprises

```
                                            (SEQ ID NO: 44)
MAWGGVHTCCFHLCCCCSWPQGAVPEELHKHPGQTLLLQCQYSPKRGPYQ

PKSWCQQTSPSRCTLLVTSSKPWTAVQKSHYTIWDKPNAGFFNITMIQLT

QNDSGFYWCGIYNASENIITVLRNISLVVSPAPTTSPMWTLPWLPTSTVL

ITSPEGTSGHPSINGSETRKSRAPACLGSGGPRFLVLVLCGLLLAKGLML
```

(Uniport Q6UXN2). In certain embodiments, the notation of the mutations within the ectodomain of human TREML4 described herein are relative to SEQ ID NO: 44. For example an hTREML4 eaodomain comprising a mutation at 135 refers to a fragment of hTREML4 that comprises the hTREML4 ectodomain but having a mutation at a residue that correlates with the threonine at position 35 of full-length wild-type human TREML4 (SEQ ID NO: 44).

In some embodiments, the protein inhibitor comprises an ectodomain of human TREML4 comprising one or more mutations selected from: T35X, L65X, L66X, S69X, K71X, K78X, K86X, T95X, G156X, and H160X, in relation to full-length wild-type human TREML4, where X is any amino acid. In some embodiments, the protein inhibitor comprises an ectodomain of human TREML4 comprising one or more mutations selected from: T35S, L65R, L66V, S69T, K71E, K78E, K86D, T95K, G156E, and H160D, in relation to full-length wild-type human TREML4.

In one embodiment, the protein inhibitor comprises an ectodomain of human TREML4 comprising a K86X mutation, where X is any amino acid. In one embodiment, the protein inhibitor comprises an ectodomain of human TREML4 comprising a K86D mutation in relation to full-length wild-type human TREML4 (hTREML4-K86D). For example, in one embodiment, the ectodomain of hTREML4-K86D comprises:

```
                                            (SEQ ID NO: 2)
EELHKHPGQTLLLQCQYSPKRGPYQPKSWCQQTSPSRCTLLVTSSKPWT

AVQKSHYTIWDDPNAGFFNITMIQLTQNDSGFYWCGIYNASENIITVLR

NISLVVSPAPTTSPMWTLPWLPTSTVLITSPEGTSGHPSINGSETRKSR

APA,
``` or a variant or fragment thereof.

In one embodiment, the protein inhibitor comprises an ectodomain of human TREML4 comprising a L65X mutation, where X is any amino acid. In one embodiment, the protein inhibitor comprises an ectodomain of human TREML4 comprising a L65R mutation in relation to full-length wild-type human TREML4 (hTREML4-L65R). For example, in one embodiment, the ectodomain of hTREML4-L65R comprises:

```
                                            (SEQ ID NO: 3)
EELHKHPGQTLLLQCQYSPKRGPYQPKSWCQQTSPSRCTRLVTSSKPWT

AVQKSHYTIWDKPNAGFFNITMIQLTQNDSGFYWCGIYNASENIITVLR

NISLVVSPAPTTSPMWTLPWLPTSTVLITSPEGTSGHPSINGSETRKSR

APA,
``` or a variant or fragment thereof.

In one embodiment, the protein inhibitor comprises an ectodomain of human TREML4 comprising a K71X mutation, where X is any amino acid. In one embodiment, the protein inhibitor comprises an ectodomain of human TREML4 comprising a K71E mutation in relation to full-length wild-type human TREML4 (hTREML4-K71E). For example, in one embodiment, the ectodomain of hTREML4-K71E comprises:

```
                                            (SEQ ID NO: 4)
EELHKHPGQTLLLQCQYSPKRGPYQPKSWCQQTSPSRCTLLVTSSEPWT

AVQKSHYTIWDKPNAGFFNITMIQLTQNDSGFYWCGIYNASENIITVLR

NISLVVSPAPTTSPMWTLPWLPTSTVLITSPEGTSGHPSINGSETRKSR

AP,
``` or a variant or fragment thereof.

In one embodiment, the protein inhibitor comprises an ectodomain of human TREML4 comprising a T95K mutation, where X is any amino acid. In one embodiment, the protein inhibitor comprises an ectodomain of human TREML4 comprising a T95K mutation in relation to full-length wild-type human TREML4 (hTREML4-T95K). For example, in one embodiment, the ectodomain of hTREML4-T95K comprises:

(SEQ ID NO: 5)
EELHKHPGQTLLLQCQYSPKRGPYQPKSWCQQTSPSRCTLLVTSSKPWT

AVQKSHYTIWDKPNAGFFNIKMIQLTQNDSGFYWCGIYNASENIITVLR

NISLVVSPAPTTSPMWTLPWLPTSTVLITSPEGTSGHPSINGSETRKSR

APA, or a variant or fragment thereof.

In one embodiment, the protein inhibitor comprises an ectodomain of human TREML4 comprising a T35X mutation, where X is any amino acid. In one embodiment, the protein inhibitor comprises an ectodomain of human TREML4 comprising a T35S mutation in relation to full-length wild-type human TREML4 (hTREML4-T35S). For example, in one embodiment, the ectodomain of hTREML4-T35S comprises:

(SEQ ID NO: 6)
EELHKHPGQSLLLQCQYSPKRGPYQPKSWCQQTSPSRCTLLVTSSKPWT

AVQKSHYTIWDKPNAGFFNITMIQLTQNDSGFYWCGIYNASENIITVLR

NISLVVSPAPTTSPMWTLPWLPTSTVLITSPEGTSGHPSINGSETRKSR

APA.

In one embodiment, the protein inhibitor comprises an ectodomain of human TREML4 comprising a L66X mutation, where X is any amino acid. In one embodiment, the protein inhibitor comprises an ectodomain of human TREML4 comprising a L66V mutation in relation to full-length wild-type human TREML4 (hTREML4-L66V). For example, in one embodiment, the ectodomain of hTREML4-L66V comprises:

(SEQ ID NO: 7)
EELHKHPGQTLLLQCQYSPKRGPYQPKSWCQQTSPSRCTLVVTSSKPWT

AVQKSHYTIWDKPNAGFFNITMIQLTQNDSGFYWCGIYNASENIITVLR

NISLVVSPAPTTSPMWTLPWLPTSTVLITSPEGTSGHPSINGSETRKSR

APA.

In one embodiment, the protein inhibitor comprises an ectodomain of human TREML4 comprising a S69X mutation, where X is any amino acid. In one embodiment, the protein inhibitor comprises an ectodomain of human TREML4 comprising a S69T mutation in relation to full-length wild-type human TREML4 (hTREML4-S69T). For example, in one embodiment, the ectodomain of hTREML4-S69T comprises:

(SEQ ID NO: 8)
EELHKHPGQTLLLQCQYSPKRGPYQPKSWCQQTSPSRCTLLVTSKPWT

AVQKSHYTIWDKPNAGFFNITMIQLTQNDSGFYWCGIYNASENIITVLR

NISLVVSPAPTTSPMWTLPWLPTSTVLITSPEGTSGHPSINGSETRKSR

APA.

In one embodiment, the protein inhibitor comprises an ectodomain of human TREML4 comprising a K78X mutation, where X is any amino acid. In one embodiment, the protein inhibitor comprises an ectodomain of human TREML4 comprising a K78E mutation in relation to full-length wild-type human TREML4 (hTREML4-K78E). For example, in one embodiment, the ectodomain of hTREML4-K78E comprises:

(SEQ ID NO: 9)
EELHKHPGQTLLLQCQYSPKRGPYQPKSWCQQTSPSRCTLLVTSSKPWT

AVQESHYTIWDKPNAGFFNITMIQLTQNDSGFYWCGIYNASENIITVLR

NISLVVSPAPTTSPMWTLPWLPTSTVLITSPEGTSGHPSINGSETRKSR

APA.

In one embodiment, the protein inhibitor comprises an ectodomain of human TREML4 comprising a G156X mutation, where X is any amino acid. In one embodiment, the protein inhibitor comprises an ectodomain of human TREML4 comprising a G156E mutation in relation to full-length wild-type human TREML4 (hTREML4-G156E). For example, in one embodiment, the ectodomain of hTREML4-G156E comprises:

(SEQ ID NO: 10)
EELHKHPGQTLLLQCQYSPKRGPYQPKSWCQQTSPSRCTLLVTSSKPWT

AVQKSHYTIWDKPNAGFFNITMIQLTQNDSGFYWCGIYNASENIITVLR

NISLVVSPAPTTSPMWTLPWLPTSTVLITSPEETSGHPSINGSETRKSR

APA.

In one embodiment, the protein inhibitor comprises an ectodomain of human TREML4 comprising a H160X mutation, where X is any amino acid. In one embodiment, the protein inhibitor comprises an ectodomain of human TREML4 comprising a H160D mutation in relation to full-length wild-type human TREML4 (hTREML4-H160D). For example, in one embodiment, the ectodomain of hTREML4-H160D comprises:

(SEQ ID NO: 11)
EELHKHPGQTLLLQCQYSPKRGPYQPKSWCQQTSPSRCTLLVTSSKPWT

AVQKSHYTIWDKPNAGFFNITMIQLTQNDSGFYWCGIYNASENIITVLR

NISLVVSPAPTTSPMWTLPWLPTSTVLITSPEGTSGDPSINGSETRKSR

APA.

In one embodiment, the protein inhibitor comprises an ectodomain of human TREML4 comprising a triple mutation of L65R/K71E/K86D in relation to full-length wild-type human TREML4 (hTREML4-L65R/K71E/K86D). For example, in one embodiment, the ectodomain of hTREML4-L65R/K71E/K86D comprises:

(SEQ ID NO: 12)
EELHKHPGQTLLLQCQYSPKRGPYQPKSWCQQTSPSRCTRLVTSSEPWT

AVQKSHYTIWDDPNAGFFNITMIQLTQNDSGFYWCGIYNASENIITVLR

NISLVVSPAPTTSPMWTLPWLPTSTVLITSPEGTSGHPSINGSETRKSR

APA, or a variant or fragment thereof.

In one embodiment, the protein inhibitor comprises an ectodomain of human TREML4 comprising a quadruple mutation of in relation to full-length wild-type human TREML4 L65R/K71E/K86D/T95K (hTREML4-L65R/K71E/K86D/T95K). For example, in one embodiment, the ectodomain of hTREML4-L65R/K71E/K86D/T95K comprises:

(SEQ ID NO: 13)
EELHKHPGQTLLLQCQYSPKRGPYQPKSWCQQTSPSRCT<u>R</u>LVTSS<u>E</u>PWT

AVQKSHYTIWD<u>D</u>PNAGFFNI<u>K</u>MIQLTQNDSGFYWCGIYNASENIITVLR

NISLVVSPAPTTSPMWTLPWLPTSTVLITSPEGTSGHPSINGSETRKSR

APA, or a variant or fragment thereof.

In one embodiment, the protein inhibitor comprises an ectodomain of murine TREML4. For example, in one embodiment, the ectodomain of murine TREML4 comprises:

(SEQ ID NO: 14)
EELHRMVGQSLSVQCQYKPKEESYVLKTWCRQTAPSKCTRVVTTSEPRKA

ARELQHTIWDDPEAGFFNITMTQLTEDDSAFYWCGPYYPSLREVTVLRNI

SLVVSPAPSTLPSQTIAPLPESTATIFMPFPVLTTSPEETTDSSINGTGH

RNQSSSSPGWTSPG, or a variant or fragment thereof.

In one embodiment, the protein inhibitor comprises an ectodomain of human TREM2. For example, in one embodiment, the ectodomain of TREM2 comprises:

(SEQ ID NO: 15)
HNTTVFQGVAGQSLQVSCPYDSMKHWGRRKAWCRQLGEKGPCQRVVSTHN

LWLLSFLRRWNGSTAITDDTLGGTLTITLRNLQPHDAGLYQCQSLHGSEA

DTLRKVLVEVLADPLDHRDAGDLWFPGESESFEDAHVEHSISR, or a variant or fragment thereof.

In one embodiment, the protein inhibitor comprises an ectodomain of human TREM1. For example, in one embodiment, the ectodomain of TREM1 comprises:

(SEQ ID NO: 16)
ATKLTEEKYELKEGQTLDVKCDYTLEKFASSQKAWQIIRDGEMPKTLACT

ERPSKNSHPVQVGRIILEDYHDHGLLRVRMVNLQVEDSGLYQCVIYQPPK

EPHMLFDRIRLVVTKGFSGTPGSNENSTQNVYKIPPTTTKALCPLYTSPR

TV, or a variant or fragment thereof.

In one embodiment, the protein inhibitor comprises an ectodomain of human TREML1. For example, in one embodiment, the ectodomain of TREML1 comprises:

(SEQ ID NO: 17)
QGIVGSLPEVLQAPVGSSILVQCHYRLQDVKAQKVWCRFLPEGCQPLVSS

AVDRRAPAGRRTFLTDLGGGLLQVEMVTLQEEDAGEYGCMVDGARGPQIL

HRVSLNILPPEEEEETHKIGSLAENAFSDPAGSANPLEPSQDEKSIP, or a variant or fragment thereof.

In one embodiment, the protein inhibitor comprises an ectodomain of human TREML2. For example, in one embodiment, the ectodomain of TREML2 comprises:

(SEQ ID NO: 18)
PSADSVYTKVRLLEGETLSVQCSYKGYKNRVEGKVWCKIRKKKCEPGFAR

VWVKGPRYLLQDDAQAKVVNITMVALKLQDSGRYWCMRNTSGILYPLMGF

QLDVSPAPQTERNIPFTHLDNILKSGTVTTGQAPTSGPDAPFTTGVMVFT

PGLITLPRLLAST, or a variant or fragment thereof.

In some embodiments, the protein inhibitor comprises a fusion protein comprising a first domain and a second domain. In one embodiment, the first domain comprises an ectodomain of one or more TREM or TREML proteins. For example, in one embodiment, the first domain comprises an ectodomain provided by at least one of SEQ ID NOS: 1-18, or a variant or fragment thereof.

In one embodiment, the second domain comprises a peptide that enhances stability or half-life of the fusion protein. For example, in one embodiment, the second domain comprises at least one region of an immunoglobulin, human serum albumin (HSA), or a peptide or antibody fragment that binds to immunoglobulin, HSA, the erythrocyte cell surface, or the neonatal Fc receptor. In one embodiment, the second domain comprises a fragment or variant of at least one region of an immunoglobulin. For example, in one embodiment, the second domain comprises an Fc region of an immunoglobulin. Exemplary immunoglobulins include, but is not limited to, IgG1, IgG2, IgG3, IgG4, IgM, IgA, IgE, and IgD. In certain embodiments, the peptide comprises an immunoglobulin comprising one or more mutations to reduce effector function, as described, for example in, Lo et al., 2017, J Biol Chem, 292(9): 3900-3908; Bolt et al., 1993, Eur J Immunol, 23: 403-411; Leabman et al., 2013, MAbs, 5: 896-903; Tao and Morrison, 1989, J Immunol, 143: 2595-2601; Walker et al., 1989, Biochem J, 347-353; Alegre et al., 1992, J Immunol, 148: 3461-3468; Xu et al., 2000, Cell Immunol, 200: 16-26; Rother et al., 2007, Nat Biotechnol, 25: 1256-1264; An et al., 2009, MAbs, 1: 572-579; Vafa et al., 2014, Methods, 65: 114-126, and Wang et al., 2018, Protein Cell, 9(1): 63-73; each of which are incorporated by reference herein in their entireties.

In one embodiment, the second domain comprises the Fc domain of human IgG1. For example, in one embodiment, the Fc domain of wild-type human IgG1 comprises:

(SEQ ID NO: 19)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK, or a variant or fragment thereof.

In one embodiment, the second domain comprises a fragment or variant of the Fc domain of human IgG1. In some embodiments, the Fc domain is mutated to reduce Fc effector functions through Fc receptors or complement. For example, in certain embodiments the Fc domain of IgG1 is mutated at one or more of D265, N297, L234, L235, P331, P329 or K332 to reduce effector function. For example, in certain embodiments the Fc domain of IgG1 is mutated at one or more of D265A, N297Q, N297A, N297G, L234A, L234F, L235E, L235A, K322A, P329G, and P331S. The peptide may comprise IgG1 having one or more mutations in the Fc region as described, for example in, Lo et al., 2017, J Biol Chem, 292(9): 3900-3908; Bolt et al., 1993, Eur J Immunol, 23: 403-411; Leabman et al., 2013, MAbs, 5: 896-903; Tao and Morrison, 1989, J Immunol, 143: 2595-2601; Walker et al., 1989, Biochem J, 347-353; Alegre et al., 1992, J Immunol, 148: 3461-3468; Xu et al., 2000, Cell Immunol, 200: 16-26; Rother et al., 2007, Nat Biotechnol, 25: 1256-1264; An et al., 2009, MAbs, 1: 572-579; and Vafa et al., 2014, Methods, 65: 114-126.

In certain embodiments, the peptide comprises an IgG1 domain comprising one or more mutations in its hinge region to reduce effector function, as described for example in Dall'Acqua et al., 2006, J Immunol, 177(2): 1129-1138, which is incorporated by reference herein in its entirety.

In one embodiment, the second domain comprises a fragment or variant of the Fc domain of human IgG2. In some embodiments, the Fc domain is mutated to reduce Fc effector functions through Fc receptors or complement. For example, in certain embodiments the Fc domain of IgG2 is mutated at one or more of H268, V309, A330, P331, V234, G237, P238, and H268 to reduce effector function. For example, in certain embodiments the Fc domain of IgG1 is mutated at one or more of H268Q, V309I, A330S, P331S, V234A, G237A, P238S, and H268A.

In one embodiment, the second domain comprises a fragment or variant of the Fc domain of human IgG4. In some embodiments, the Fc domain is mutated to reduce Fc effector functions through Fc receptors or complement. For example, in certain embodiments the Fc domain of IgG4 is mutated at one or more of F234 and L235 to reduce effector function. For example, in certain embodiments the Fc domain of IgG1 is mutated at one or more of F234A and L235A. In one embodiment, the second domain comprises and IgG2/IgG4 cross isotype.

For example, in some embodiments, the second domain comprises an aglycosylated variant of the Fc domain of human IgG1. In some embodiments, the second domain comprises a variant of the Fc domain of human IgG1 where N297 is mutated to prevent glycosylation. In some embodiments, the second domain comprises a variant of the Fc domain of human IgG1 comprising an N297Q, N297A, or N297G mutation, relative to wildtype full-length IgG1.

For example, in one embodiment, the second domain comprises a variant of the Fc domain of human IgG1, wherein the variant comprises an N297Q mutation. For example, in one embodiment, the variant of the Fc domain comprises:

(SEQ ID NO: 20)
DKTHTCPPCPAPELLGGPSVFLFPPKPKDTLMISRTPEVTCVVVDVSHED

PEVKFNWYVDGVEVHNAKTKPREEQYQSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK, or a variant or fragment thereof.

For example, in one embodiment, the second domain comprises a variant of the Fc domain of human IgG1, wherein the variant comprises an N297A mutation. For example, in one embodiment, the variant of the Fc domain comprises:

(SEQ ID NO: 21)
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

For example, in one embodiment, the second domain comprises a variant of the Fc domain of human IgG1, wherein the variant comprises an N297G mutation. For example, in one embodiment, the variant of the Fc domain comprises:

(SEQ ID NO: 22)
DKTHTCPPCPAPELLGGPSVFLFPPKPKDTLMISRTPEVTCVVVDVSHED

PEVKFNWYVDGVEVHNAKTKPREEQYGSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

In some embodiments, the second domain comprises a fragment or variant of an Fc domain containing mutations that confer enhanced half-life in serum. In some embodiments, the mutations increase the association of the Fc domain with the neonatal Fc receptor (FcRn). In some embodiments, those mutations include the "YTE" triple mutation (M252Y/S254T/T256E). In some embodiments, those mutations include the "LS" double mutation (M428L/N434S).

In some embodiments, the second domain comprises a fragment or variant of an Fc domain that contains combinations of mutations that both remove or reduce effector functions and also extend the half-life of the Fc domain. For example, the combination of the N297A mutation with the YTE triple mutation ("AYTE"), or the combination of the N297A mutation with the LS double mutation ("ALS").

In some embodiments, the fusion protein comprises a linker domain separating the first domain and second domain. In one embodiment, the linker domain comprises GGGSGGSGGSGGS (SEQ ID NO: 23). In another embodiment, the linker domain comprises one or more repeats of the 5-mer (GGGGS (SEQ ID NO: 24). In one embodiment, the linker domain comprises 3 repeats of GGGGS (SEQ ID NO: 24). In another embodiment, the linker domain comprises AAA. In one embodiment, the linker domain comprises GGGSGGSGGSGGS (SEQ ID NO: 23) and AAA.

In some embodiments, the fusion protein comprises a secretory leader sequence. For example in one embodiment, the leader sequence comprises the H7 leader peptide derived from the leader sequence of the IgG heavy chain. In one embodiment, the leader sequence comprises MEFGLSWVFLVALFRGVQS (SEQ ID NO: 25). Other exemplary leader peptides include, but are not limited to, the IgG kappa light chain, the IgG lambda light chain, the leader peptide from Human Serum Albumin, and the leader peptide from Interleukin-2.

In one embodiment, the fusion protein comprises a first domain comprising human TREML4 and a second domain comprising a variant of the Fc domain of human IgG1, wherein the Fc domain comprises a glycosylation site N297Q mutation. For example, in one embodiment, the fusion protein comprises the amino acid sequence of (SEQ ID NO: 26)
MEFGLSWVFLVALFRGVQS<u>EELHKHPGQTLLLQCQYSPKRGPYQPKSWCQ</u>

<u>QTSPSRCTLLVTSSKPWTAVQKSHYTIWDKPNAGFFNITMIQLTQNDSGF</u>

<u>YWCGIYNASENIITVLRNISLVVSPAPTTSPMWTLPWLPTSTVLITSPEG</u>

<u>TSGHPSINGSETRKSRAPA</u>GGGGSGGGGSGGGGSDKTHTCPPCPAPELLG

GPSVFLFPPKPKDTLMISRTPEVTCVVVDVSHEDPEVKFNWYVDGVEVHN

AKTKPREEQYQSTYRVVSVLTVLHQDWLNGKEYKCKVSNKALPAPIEKTI

SKAKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHNHY

TQKSLSLSPGK, where the ectodomain is underlined.

In one embodiment, the fusion protein comprises a first domain comprising hTREML4-K86D and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 27)
MEFGLSWVFLVALFRGVQS<u>EELHKHPGQTLLLQCQYSPKRGPYQPKSWCQ</u>

<u>QTSPSRCTLLVTSSKPWTAVQKSHYTIWDDPNAGFFNITMIQLTQNDSGF</u>

<u>YWCGIYNASENIITVLRNISLVVSPAPTTSPMWTLPWLPTSTVLITSPEG</u>

<u>TSGHPSINGSETRKSRAPA</u>GGGGSGGGGSGGGGSDKTHTCPPCPAPELLG

GPSVFLFPPKPKDTLMISRTPEVTCVVVDVSHEDPEVKFNWYVDGVEVHN

AKTKPREEQYQSTYRVVSVLTVLHQDWLNGKEYKCKVSNKALPAPIEKTI

SKAKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHNHY

TQKSLSLSPGK, where the ectodomain is underlined.

In one embodiment, the fusion protein comprises a first domain comprising hTREML4-L65R and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 28)
MEFGLSWVFLVALFRGVQS<u>EELHKHPGQTLLLQCQYSPKRGPYQPKHSWC</u>

<u>QQTSPSRCTRLVTSSKPWTAVQKSHYTIWDKPNAGFFNITMIQLTQNDSG</u>

<u>FYWCGIYNASENIITVLRNISLVVSPAPTTSPMWTLPWLPTSTVLITSPE</u>

<u>GTSGHPSINGSETRKSRAPA</u>GGGGSGGGGSGGGGSDKTHTCPPCPAPELL

GGPSVFLFPPKPKDTLMISRTPEVTCVVVDVSHEDPEVKFNWYVDGVEVH

NAKTKPREEQYQSTYRVVSVLTVLHQDWLNGKEYKCKVSNKALPAPIEKT

ISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNH

YTQKSLSLSPGK, where the ectodomain is underlined.

In one embodiment, the fusion protein comprises a first domain comprising hTREML4-K71E and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 29)
MEFGLSWVFLVALFRGVQS<u>EELHKUPGQTLLLQCQYSPKRGPYQPK</u>

<u>SWCQQTSPSRCTLLVTSSEPWTAVQKSHYTIWDKPNAGFFNITMIQ</u>

<u>LTQNDSGFYWCGIYNASENIITVLRNISLVVSPAPTTSPMWTLPWL</u>

<u>PTSTVLITSPEGTSGHPSINGSETRKSRAPA</u>GGGGSGGGGSGGGGS

DKTHTCPPCPAPELLGGPSVFLFPPKPKDTLMISRTPEVTCVVVDV

SHEDPEVKFNWYVDGVEVHNAKTKPREEQYQSTYRVVSVLTVLHQD

WLNGKEYKCKVSNKALPAPIEKTISKAKGQPREPQVYTLPPSREEM

TKNQVSLTCLVKGFYPSDIAVEWESNGQPENNYKTTPPVLDSDGSF

FLYSKLTVDKSRWQQGNVFSCSVMHEALHNHYTQKSLSLSPGK, where the ectodomain is underlined.

In one embodiment, the fusion protein comprises a first domain comprising hTREML4-T95K and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 30)
MEFGLSWVELVALFRGVQS<u>EELHKEIPGQTLLLQCQYSPKRGPYQP</u>

<u>KSWCQQTSPSRCTLLVTSSKPWTAVQKSHYTIWDKPNAGFFNIKMI</u>

<u>QLTQNDSGFYWCGIYNASENIITVLRNISLVVSPAPTTSPMWTLPW</u>

<u>LPTSTVLITSPEGTSGHPSINGSETRKSRAPA</u>GGGGSGGGGSGGGG

SDKTHTCPPCPAPELLGGPSVFLEPPKPKDTLMISRTPEVTCVVVD

VSHEDPEVKFNWYVDGVEVHNAKTKPREEQYQSTYRVVSVLTVLHQ

DWLNGKEYKCKVSNKALPAPIEKTISKAKGQPREPQVYTLPPSREE

MTKNQVSLTCLVKGFYPSDIAVEWESNGQPENNYKTTPPVLDSDGS

FFLYSKLTVDKSRWQQGNVFSCSVMHEALHNHYTQKSLSLSPGK, where the ectodomain is underlined.

In one embodiment, the fusion protein comprises a first domain comprising hTREML4-T35S and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 31)
MEFGLSWVELVALFRGVQS<u>EELHKEIPGQSLLLQCQYSPKRGPYQP</u>

<u>KSWCQQTSPSRCTLLVTSSKPWTAVQKSHYTIWDKPNAGFFNITMI</u>

-continued

QLTQNDSGFYWCGIYNASENIITVLRNISLVVSPAPTTSPMWTLPW

LPTSTVLITSPEGTSGHPSINGSETRKSRAPAGGGGSGGGGSGGGG

SDKTHTCPPCPAPELLGGPSVFLEPPKPKDTLMISRTPEVTCVVVD

VSHEDPEVKFNWYVDGVEVHNAKTKPREEQYQSTYRVVSVLTVLHQ

DWLNGKEYKCKVSNKALPAPIEKTISKAKGQPREPQVYTLPPSREE

MTKNQVSLTCLVKGFYPSDIAVEWESNGQPENNYKTTPPVLDSDGS

FFLYSKLTVDKSRWQQGNVFSCSVMHEALHNHYTQKSLSLSPGK, where the ectodomain is underlined.

In one embodiment, the fusion protein comprises a first domain comprising hTREML4-L66V and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 32)
MEFGLSWVELVALFRGVQSEELHKEIPGQTLLLQCQYSPKRGPYQ

PKSWCQQTSPSRCTLVVTSSKPWTAVQKSHYTIWDKPNAGFFNIT

MIQLTQNDSGFYWCGIYNASENIITVLRNISLVVSPAPTTSPMWT

LPWLPTSTVLITSPEGTSGHPSINGSETRKSRAPAGGGGSGGGGS

GGGGSDKTHTCPPCPAPELLGGPSVFLEPPKPKDTLMISRTPEVT

CVVVDVSHEDPEVKFNWYVDGVEVHNAKTKPREEQYQSTYRVVSV

LTVLHQDWLNGKEYKCKVSNKALPAPIEKTISKAKGQPREPQVYT

LPPSREEMTKNQVSLTCLVKGFYPSDIAVEWESNGQPENNYKTTP

PVLDSDGSFFLYSKLTVDKSRWQQGNVFSCSVMHEALHNHYTQKS

LSLSPGK, where the ectodomain is underlined.

In one embodiment, the fusion protein comprises a first domain comprising hTREML4-S69T and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 33)
MEFGLSWVELVALFRGVQSEELHKEIPGQTLLLQCQYSPKRGPYQ

PKSWCQQTSPSRCTLLVTTSSKPWTAVQKSHYTIWDKPNAGFFNIT

MIQLTQNDSGFYWCGIYNASENIITVLRNISLVVSPAPTTSPMWT

LPWLPTSTVLITSPEGTSGHPSINGSETRKSRAPAGGGGSGGGGS

GGGGSDKTHTCPPCPAPELLGGPSVFLEPPKPKDTLMISRTPEVT

CVVVDVSHEDPEVKFNWYVDGVEVHNAKTKPREEQYQSTYRVVSV

LTVLHQDWLNGKEYKCKVSNKALPAPIEKTISKAKGQPREPQVYT

LPPSREEMTKNQVSLTCLVKGFYPSDIAVEWESNGQPENNYKTTP

PVLDSDGSFFLYSKLTVDKSRWQQGNVFSCSVMHEALHNHYTQKS

LSLSPGK, where the ectodomain is underlined.

In one embodiment, the fusion protein comprises a first domain comprising hTREML4-K78E and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 34)
MEFGLSWVELVALFRGVQSEELHKEIPGQTLLLQCQYSPKRGPYQ

PKSWCQQTSPSRCTLLVTSSKPWTAVQESHYTIWDKPNAGFFNIT

MIQLTQNDSGFYWCGIYNASENIITVLRNISLVVSPAPTTSPMWT

LPWLPTSTVLITSPEGTSGHPSINGSETRKSRAPAGGGGSGGGGS

GGGGSDKTHTCPPCPAPELLGGPSVFLEPPKPKDTLMISRTPEVT

CVVVDVSHEDPEVKFNWYVDGVEVHNAKTKPREEQYQSTYRVVSV

LTVLHQDWLNGKEYKCKVSNKALPAPIEKTISKAKGQPREPQVYT

LPPSREEMTKNQVSLTCLVKGFYPSDIAVEWESNGQPENNYKTTP

PVLDSDGSFELYSKLTVDKSRWQQGNVFSCSVMHEALHNHYTQKS

LSLSPGK, where the ectodomain is underlined.

In one embodiment, the fusion protein comprises a first domain comprising hTREML4-G156E and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 35)
MEFGLSWVELVALFRGVQSEELHKEIPGQTLLLQCQYSPKRGPY

QPKSWCQQTSPSRCTLLVTSSKPWTAVQKSHYTIWDKPNAGFFN

ITMIQLTQNDSGFYWCGIYNASENIITVLRNISLVVSPAPTTSP

MWTLPWLTPSTVLITSPEETSGHPSINGSETRKSRAPAGGGGSG

GGGSGGGGSDKTHTCPPCPAPELLGGPSVFLEPPKPKDTLMISR

TPEVTCVVVDVSHEDPEVKFNWYVDGVEVHNAKTKPREEQYQST

YRVVSVLTVLHQDWLNGKEYKCKVSNKALPAPIEKTISKAKGQP

REPQVYTLPPSREEMTKNQVSLTCLVKGFYPSDIAVEWESNGQP

ENNYKTTPPVLDSDGSFELYSKLTVDKSRWQQGNVFSCSVMHEA

LHNHYTQKSLSLSPGK, where the ectodomain is underlined.

In one embodiment, the fusion protein comprises a first domain comprising hTREML4-H160D and a second domain comprising a variant of the Fc domain of human IgG1, wherein the Fc domain contains a glycosylation site N297Q mutation. For example, in one embodiment, the fusion protein comprises the amino acid sequence of (SEQ ID NO: 36)
MEFGLSWVELVALFRGVQSEELHKEIPGQTLLLQCQYSPKRGPY

QPKSWCQQTSPSRCTLLVTSSKPWTAVQKSHYTIWDKPNAGFFN

ITMIQLTQNDSGFYWCGIYNASENIITVLRNISLVVSPAPTTSP

MWTLPWLTPSTVLITSPEGTSGDPSINGSETRKSRAPAGGGGSG

GGGSGGGGSDKTHTCPPCPAPELLGGPSVFLEPPKPKDTLMISR

```
TPEVTCVVVDVSHEDPEVKFNWYVDGVEVHNAKTKPREEQYQST
YRVVSVLTVLHQDWLNGKEYKCKVSNKALPAPIEKTISKAKGQP
REPQVYTLPPSREEMTKNQVSLTCLVKGFYPSDIAVEWESNGQP
ENNYKTTPPVLDSDGSFELYSKLTVDKSRWQQGNVFSCSVMHEA
LHNHYTQKSLSLSPGK,
``` where the ectodomain is underlined.

In one embodiment, the fusion protein comprises a first domain comprising hTREML4-L65R/K71E/K86D and a second domain comprising a variant of the Fc domain of human IgG1, wherein the Fc domain contains a glycosylation site N297Q mutation. For example, in one embodiment, the fusion protein comprises the amino acid sequence of

```
                                    (SEQ ID NO: 37)
MEFGLSWVELVALFRGVQSEELHKEIPGQTLLLQCQYSPKRGPY
QPKSWCQQTSPSRCTRLVTSSEPWTAVQKSHYTIWDDPNAGFFN
ITMIQLTQNDSGFYWCGIYNASENIITVLRNISLVVSPAPTTSP
MWTLPWLPTSTVLITSPEGTSGHPSINGSETRKSRAPAGGGGSG
GGGSGGGGSDKTHTCPPCPAPELLGGPSVFLEPPKPKDTLMISR
TPEVTCVVVDVSHEDPEVKFNWYVDGVEVHNAKTKPREEQYQST
YRVVSVLTVLHQDWLNGKEYKCKVSNKALPAPIEKTISKAKGQP
REPQVYTLPPSREEMTKNQVSLTCLVKGFYPSDIAVEWESNGQP
ENNYKTTPPVLDSDGSFELYSKLTVDKSRWQQGNVFSCSVMHEA
LHNHYTQKSLSLSPGK,
``` where the ectodomain is underlined.

In one embodiment, the fusion protein comprises a first domain comprising hTREML4-L65R/K71E/K86D/T95K and a second domain comprising a variant of the Fc domain of human IgG1, wherein the Fc domain contains a glycosylation site N297Q mutation. For example, in one embodiment, the fusion protein comprises the amino acid sequence of

```
                                    (SEQ ID NO: 38)
MEFGLSWVFLVALFRGVQSEELHKHPGQTLLLOCQYSPKRGPY
QPKSWCQQTSPSRCTRLVTSSEPWTAVQKSHYTIWDDPNAGFF
NIKMIQLTQNDSGFYWCGIYNASENIITVLRNISLVVSPAPTT
SPMWTLPWLPTSTVLITSPEGTSGHPSINGSETRKSRAPAGGG
GSGGGGSGGGGSDKTHTCPPCPAPELLGGPSVFLEPPKPKDTL
MISRTPEVTCVVVDVSHEDPEVKFNWYVDGVEVHNAKTKPREE
QYQSTYRVVSVLTVLHQDWLNGKEYKCKVSNKALPAPIEKTIS
KAKGQPREPQVYTLPPSREEMTKNQVSLTCLVKGEYPSDIAVE
WESNGQPENNYKTTPPVLDSDGSFFLYSKLTVDKSRWQQGNVF
SCSVMHEALHNHYTQKSLSLSPGK,
``` where the ectodomain is underlined.

In one embodiment, the fusion protein comprises a first domain comprising murine TREML4 and a second domain comprising a variant of the Fc domain of human IgG1, wherein the Fc domain comprises a glycosylation site N297Q mutation. For example, in one embodiment, the fusion protein comprises the amino acid sequence of

```
                                    (SEQ ID NO: 39)
MEFGLSWVFLVALFRGVQSEELHRMVGQSLSVOCQYKPKEESY
VLKTWCRQTAPSKCTRVVTTSEPRKAARELQHTIWDDPEAGFF
NITMTQLTEDDSAFYWCGPYYPSLREVTVLRNISLVVSPAPST
LPSQTIAPLPESTATIFMPFPVLTTSPEETTDSSINGTGHRNQ
SSSSPGWTSPGGGGGSGGGGSGGGGSDKTHTCPPCPAPELLGG
PSVFLFPPKPKDTLMISRTPEVTCVVVDVSHEDPEVKFNWYVD
GVEVHNAKTKPREEQYQSTYRVVSVLTVLHQDWLNGKEYKCKV
SNKALPAPIEKTISKAKGQPREPQVYTLPPSREEMTKNQVSLT
CLVKGFYPSDIAVEWESNGQPENNYKTTPPVLDSDGSFFLYSK
LTVDKSRWQQGNVFSCSVMHEALHNHYTQKSLSLSPGK,
``` where the ectodomain is underlined.

In one embodiment, the fusion protein comprises a first domain comprising human TREM2 and a second domain comprising a variant of the Fc domain of human IgG1, wherein the Fc domain comprises a glycosylation site N297Q mutation. For example, in one embodiment, the fusion protein comprises the amino acid sequence of

```
                                    (SEQ ID NO: 40)
MEFGLSWVFLVALFRGVQSHNTTVFQGVAGQSLQVSCPYDSMK
HWGRRKAWCRQLGEKGPCQRVVSTHNLWLLSFLRRWNGSTAIT
DDTLGGTLTITLRNLQPHDAGLYQCQSLHGSEADTLRKVLVEV
LADPLDHRDAGDLWFPGESESFEDAHVEHSISRGGGGSGGGGS
GGGGSDKTHTCPPCPAPELLGGPSVFLFPPKPKDTLMISRTPE
VTCVVVDVSHEDPEVKFNWYVDGVEVHNAKTKPREEQYQSTYR
VVSVLTVLHQDWLNGKEYKCKVSNKALPAPIEKTISKAKGQPR
EPQVYTLPPSREEMTKNQVSLTCLVKGFYPSDIAVEWESNGQP
ENNYKTTPPVLDSDGSFFLYSKLTVDKSRWQQGNVFSCSVMHE
ALHNHYTQKSLSLSPGK,
``` where the ectodomain is underlined.

In one embodiment, the fusion protein comprises a first domain comprising human TREM1 and a second domain comprising a variant of the Fc domain of human IgG1, wherein the Fc domain comprises a glycosylation site N297Q mutation. For example, in one embodiment, the fusion protein comprises the amino acid sequence of

```
                                    (SEQ ID NO: 41)
MEFGLSWVFLVALFRGVQSATKLTEEKYELKEGQTLDVKCDYT
LEKFASSQKAWQIIRDGEMPKTLACTERPSKNSHPVQVGRIIL
EDYHDHGLLRVRMVNLQVEDSGLYQCVIYQPPKEPHMLFDRIR
LVVTKGFSGTPGSNENSTQNVYKIPPTTTKALCPLYTSPRTVG
GGGSGGGGSGGGGSDKTHTCPPCPAPELLGGPSVFLFPPKPKD
TLMISRTPEVTCVVVDVSHEDPEVKFNWYVDGVEVHNAKTKPR
```

-continued

```
EEQYQSTYRVVSVLTVLHQDWLNGKEYKCKVSNKALPAPIEKT

ISKAKGQPREPQVYTLPPSREEMTKNQVSLTCLVKGFYPSDIA

VEWESNGQPENNYKTTPPVLDSDGSFFLYSKLTVDKSRWQQGN

VFSCSVMHEALHNHYTQKSLSLSPGK,
``` where the ectodomain is underlined.

In one embodiment, the fusion protein comprises a first domain comprising human TREML1 and a second domain comprising a variant of the Fc domain of human IgG1, wherein the Fc domain comprises a glycosylation site N297Q mutation. For example, in one embodiment, the fusion protein comprises the amino acid sequence of

```
                                        (SEQ ID NO: 42)
MEFGLSWVFLVALFRGVQSQGIVGSLPEVLQAPVGSSILVQCH

YRLQDVKAQKVWCRFLPEGCQPLVSSAVDRRAPAGRRTFLTDL

GGGLLQVEMVTLQEEDAGEYGCMVDGARGPQILHRVSLNILPP

EEEEETHKIGSLAENAFSDPAGSANPLEPSQDEKSIPGGGGSG

GGGSGGGGSDKTHTCPPCPAPELLGGPSVFLFPPKPKDTLMIS

RTPEVTCVVVDVSHEDPEVKFNWYVDGVEVHNAKTKPREEQYQ

STYRVVSVLTVLHQDWLNGKEYKCKVSNKALPAPIEKTISKAK

GQPREPQVYTLPPSREEMTKNQVSLTCLVKGEYPSDIAVEWES

NGQPENNYKTTPPVLDSDGSFFLYSKLTVDKSRWQQGNVFSCS

VMHEALHNHYTQKSLSLSPGK,
``` where the ectodomain is underlined.

In one embodiment, the fusion protein comprises a first domain comprising human TREML2 and a second domain comprising a variant of the Fc domain of human IgG1, wherein the Fc domain comprises a glycosylation site N297Q mutation. For example, in one embodiment, the fusion protein comprises the amino acid sequence of

```
                                        (SEQ ID NO: 43)
MEFGLSWVFLVALFRGVQSPSADSVYTKVRLLEGETLSVQCSY

KGYKNRVEGKVWCKIRKKKCEPGFARVWVKGPRYLLQDDAQAK

VVNITMVALKLQDSGRYWCMRNTSGILYPLMGFQLDVSPAPQT

ERNIPFTHLDNILKSGTVTTGQAPTSGPDAPFTTGVMVFTPGL

ITLPRLLASTGGGSGGGGSGGGGSDKTHTCPPCPAPELLGGP

SVFLEPPKPKDTLMISRTPEVTCVVVDVSHEDPEVKFNWYVDG

VEVHNAKTKPREEQYQSTYRVVSVLTVLHQDWLNGKEYKCKVS

NKALPAPIEKTISKAKGQPREPQVYTLPPSREEMTKNQVSLTC

LVKGFYPSDIAVEWESNGQPENNYKTTPPVLDSDGSFFLYSKL

TVDKSRWQQGNVFSCSVMHEALHNHYTQKSLSLSPGK,
``` where the ectodomain is underlined.

In one embodiment, a composition of the invention comprises a dimer two of the proteins described herein. In one embodiment, the dimer is a homodimer, comprising two identical proteins. In one embodiment, the dimer is a heterodimer, comprising two non-identical proteins.

The invention should also be construed to include any form of a protein variant having substantial homology to an amino acid sequence disclosed herein. In one embodiment, a protein variant is at least about 50%, 70%, 80%, 85%, 86%, 87%, 88%, 89%, 90%, 91%, 92%, 93%, 94%, 95%, 96%, 97%, 98%, or 99% homologous to an amino acid sequence disclosed herein.

The invention should also be construed to include any form of a fragment having a substantial length of an amino acid sequence disclosed herein. In one embodiment, a fragment is at least about 50%, 70%, 80%, 85%, 86%, 87%, 88%, 89%, 90%, 91%, 92%, 93%, 94%, 95%, 96%, 97%, 98%, or 99% of the length of an amino acid sequence disclosed herein.

The invention should also be construed to include any form of a fragment of a protein variant, having both substantial homology to and a substantial length of an amino acid sequence disclosed herein. In one embodiment, a fragment of a protein variant is at least about 50%, 70%, 80%, 85%, 86%, 87%, 88%, 89%, 90%, 91%, 92%, 93%, 94%, 95%, 96%, 97%, 98%, or 99% homologous to an amino acid sequence disclosed herein, and is at least about 50%, 70%, 80%, 85%, 86%, 87%, 88%, 89%, 90%, 91%, 92%, 93%, 94%, 95%, 96%, 97%, 98%, or 99% of the length of an amino acid sequence disclosed herein.

The protein may alternatively be made by recombinant means or by cleavage from a longer protein. The protein may be confirmed by amino acid analysis or sequencing.

The variants of the proteins according to the present invention may be (i) one in which one or more of the amino acid residues are substituted with a conserved or non-conserved amino acid residue (e.g., a conserved amino acid residue) and such substituted amino acid residue may or may not be one encoded by the genetic code, (ii) one in which there are one or more modified amino acid residues, e.g., residues that are modified by the attachment of substituent groups, (iii) one in which the protein comprises an alternative splice variant of the proteins or domains described herein, (iv) fragments of the proteins or domains described herein and/or (v) one in which the protein is fused with another protein or peptide, such as a leader or secretory sequence or a sequence which is employed for purification (for example, His-tag) or for detection (for example, Sv5 epitope tag). The fragments include proteins or peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, e.g., different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two polypeptides may be determined using computer algorithms and methods that are widely known for the persons skilled in the art. The identity between two amino acid sequences may be determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The protein of the invention may or may not be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction. A polypeptide or protein of the invention may be phosphorylated using conventional methods such as the method described in Reedijk et al. (The EMBO Journal 11(4):1365, 1992).

The protein of the invention may include unnatural amino acids formed by post-translational modification or by introducing unnatural amino acids during translation. A variety of approaches are available for introducing unnatural amino acids during polypeptide translation.

A protein of the invention may be conjugated with other molecules, such as polyethylene glycol (PEG). This may be accomplished by inserting cysteine mutations or unnatural amino acids that can be modified with a chemically reactive PEG derivative. In one embodiment, the protein is conjugated to other proteins, to prepare fusion proteins. This may be accomplished, for example, by the synthesis of N-terminal or C-terminal fusion proteins provided that the resulting fusion protein retains the functionality of the protein inhibitor described herein.

Cyclic derivatives of the proteins of the invention are also part of the present invention. Cyclization may allow the protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic protein which is more flexible than the cyclic proteins containing peptide bond linkages as described above. A more flexible protein may be prepared by introducing cysteines at the right and left position of the polypeptide and forming a disulfide bridge between the two cysteines. The two cysteines are arranged so as not to deform the beta-sheet and turn. The protein is more flexible as a result of the length of the disulfide linkage and the smaller number of hydrogen bonds in the beta-sheet portion. The relative flexibility of a cyclic protein can be determined by molecular dynamics simulations.

The invention also relates to a peptide inhibitor described herein fused to, or integrated into, a targeting protein, or a targeting domain capable of directing the resulting protein to a desired cellular component or cell type or tissue. The chimeric or fusion proteins may also contain additional amino acid sequences or domains. The chimeric or fusion proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate, for example, with vesicles or with the cell surface. In one embodiment, the targeting domain can target a protein to a particular cell type or tissue. For example, the targeting domain can be a cell surface ligand or an antibody against cell surface antigens of a target tissue. A targeting domain may target a protein of the invention to a cellular component.

A protein of the invention may be synthesized by conventional techniques. For example, the proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a polypeptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or protein of the invention, conjugated with at least one other molecule, may be prepared by fusing, through recombinant techniques, the N-terminal or C-terminal end of the peptide or protein, and the sequence of a selected protein or selectable marker with a desired biological function. The resultant fusion proteins contain the protein comprising the TREM or TREML ectodomain fused to the selected protein or marker protein as described herein. Examples of proteins which may be used to prepare fusion proteins include immunoglobulins and regions thereof, glutathione-S-transferase (GST), hemagglutinin (HA), and truncated myc.

A protein of the invention may be developed using a biological expression system. The use of these systems allows the production of large libraries of random sequences and the screening of these libraries for sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The protein of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acids.

The present invention further encompasses fusion proteins in which the protein of the invention or fragments thereof, are recombinantly fused or chemically conjugated (including both covalent and non-covalent conjugations) to heterologous proteins (i.e., an unrelated protein or portion thereof, e.g., at least 10, at least 20, at least 30, at least 40, at least 50, at least 60, at least 70, at least 80, at least 90, at least 100, at least 125, at least 150, at least 175, at least 200, at least 225, at least 250, at least 275, at least 300, or at least 500 amino acids of the polypeptide) to generate fusion proteins. The fusion does not necessarily need to be direct, but may occur through linker sequences.

In one example, a fusion protein in which a protein of the invention or a fragment thereof can be fused to sequences derived from various types of immunoglobulins. For example, a polypeptide of the invention can be fused to a constant region (e.g., hinge, CH2, and CH3 domains) of human IgG or IgM molecule, for example, as described herein, so as to make the fused protein or fragments thereof more soluble and stable in vivo. In another embodiment, such fusion proteins can be administered to a subject so as to inhibit interactions between a ligand and its receptors in vivo. Such inhibition of the interaction will block or suppress signal transduction which triggers certain cellular responses.

In one aspect, the fusion protein comprises a polypeptide of the invention which is fused to a heterologous signal sequence at its N-terminus. For example, the signal sequence naturally found in the protein of the invention can be replaced by a signal sequence which is derived from a heterologous origin. Various signal sequences are commercially available. For example, the secretory sequences of melittin and human placental alkaline phosphatase (Stratagene; La Jolla, Calif.) are available as eukaryotic heterologous signal sequences. As examples of prokaryotic heterologous signal sequences, the phoA secretory signal (Sambrook, et al., supra; and Current Protocols in Molecular Biology, 1992, Ausubel, et al., eds., John Wiley & Sons) and the protein A secretory signal (Pharmacia Biotech; Piscataway, N.J.) can be listed. Another example is the gp67 secretory sequence of the baculovirus envelope protein (Current Protocols in Molecular Biology, 1992, Ausubel, et al., eds., John Wiley & Sons).

In another embodiment, a protein of the invention can be fused to tag sequences, e.g., a hexa-histidine peptide, such as the tag provided in a pQE vector (QIAGEN, Inc., 9259 Eton Avenue, Chatsworth, Calif., 91311), among others, many of which are commercially available. As described in Gentz, et al., 1989, Proc. Natl. Acad. Sci. USA 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson, et al., 1984, Cell 37:767) and the "flag" tag (Knappik, et al., 1994, Biotechniques 17(4):754-761). These tags are especially useful for purification of recombinantly produced proteins of the invention.

In one embodiment, the present invention provides a composition comprising an isolated nucleic acid sequence encoding a protein inhibitor described herein. For example, in one embodiment, the composition comprises an isolated nucleic acid molecule encoding an antibody or protein inhibitor that inhibits the interaction between one or more TREM or TREML protein and cardiolipin or mitochondria. In one embodiment, the isolated nucleic acid molecule encodes a peptide inhibitor comprising an ectodomain of a TREM or TREML protein.

In one embodiment, the composition comprises an isolated nucleic acid sequence encoding a biologically functional fragment of a protein inhibitor described herein. As would be understood in the art, a biologically functional fragment is a portion or portions of a full-length sequence that retains a biological function of the full-length sequence.

In various embodiments, the isolated nucleic acid sequence encodes a protein inhibitor comprising an amino acid sequence selected from the group consisting of SEQ ID NOs 1-43.

Further, the invention encompasses an isolated nucleic acid encoding a polypeptide having substantial homology to a protein inhibitor disclosed herein. In some embodiments, the isolated nucleic acid sequence encodes protein inhibitor comprising an amino acid sequence having at least about 75%, 80%, 85%, 86%, 87%, 88%, 89%, 90%, 91%, 92%, 93%, 94%, 95%, 96%, 97%, 98%, or 99% sequence homology with an amino acid sequence selected from SEQ ID NOs 1-43.

The isolated nucleic acid sequence encoding a protein inhibitor can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA, cDNA, and RNA. For example, in one embodiment, the composition comprises an isolated DNA molecule, including for example, an isolated cDNA molecule, encoding a protein inhibitor or functional fragment thereof. In one embodiment, the composition comprises an isolated RNA molecule encoding a protein inhibitor or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. The above modifications may be combined.

In some instances, the nucleic acid molecule comprises at least one of the following chemical modifications: 2'-H, 2'-O-methyl, or 2'-OH modification of one or more nucleotides. In some embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, for example different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., noncharged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a protein inhibitor is typically achieved by operably linking a nucleic acid encoding the protein inhibitor or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders.

AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In some embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a protein inhibitor, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a peptide or protein into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York).

Biological methods for introducing a peptide or protein of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a peptide or protein into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular polypeptide, e.g., by immunological means (ELISAs and Western blots) or by assays described herein to identify agents falling within the scope of the invention.

In one embodiment, the present invention provides a delivery vehicle comprising a protein inhibitor, or a nucleic acid molecule encoding protein inhibitor. Exemplary delivery vehicles include, but are not limited to, microspheres, microparticles, nanoparticles, polymerosomes, liposomes, and micelles. For example, in some embodiments, the delivery vehicle is loaded with protein inhibitor, or a nucleic acid molecule encoding a protein inhibitor. In some embodiments, the delivery vehicle provides for controlled release, delayed release, or continual release of its loaded cargo. In some embodiments, the delivery vehicle comprises a targeting moiety that targets the delivery vehicle to a treatment site.

In one embodiment, the present invention provides an implantable scaffold or device comprising the protein inhibitor or nucleic acid molecule encoding the protein inhibitor. For example, in some embodiments, the present invention provides a tissue engineering scaffold, including but not limited to, a hydrogel, electrospun scaffold, polymeric matrix, or the like, comprising the protein inhibitor or nucleic acid molecule encoding the protein inhibitor in or on the scaffold.

Pharmaceutical Compositions

The present invention also provides pharmaceutical compositions comprising one or more of the compositions described herein. Formulations may be employed in admixtures with conventional excipients, i.e., pharmaceutically acceptable organic or inorganic carrier substances suitable for administration to a treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group: benzyl alcohol, sorbic acid, parabens, imidurea and combinations thereof.

In one embodiment, the composition includes an antioxidant and a chelating agent that inhibits the degradation of one or more components of the composition. Exemplary antioxidants for some compounds are BHT, BHA, alpha-tocopherol and ascorbic acid. Exemplary chelating agents include edetate salts (e.g. disodium edetate) and citric acid. The chelating agent is useful for chelating metal ions in the composition that may be detrimental to the shelf life of the formulation. While BHT and disodium edetate may be the antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the compounds or other compositions of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid.

Methods of Inhibiting TREM and TREML Signaling

In one aspect, the present invention provides a method of inhibiting TREM and TREML signaling. For example, it is demonstrated herein that the administration of a inhibitor described herein reduces TREM and TREML-mediated signaling and reduces inflammation.

The compositions described herein may be introduced to a subject or biological system (e.g., a cell, a population of cells, a tissue, an organ, or another system) to inhibit TREM or TREML signaling, or to reduce inflammation, or treat and inflammatory or autoimmune disease or disorder, in the subject or biological system.

Treatment Methods

The present invention provides a method for the treatment or prevention of an inflammatory, autoinflammatory, or autoimmune disease or disorder in a subject in need thereof. The present method may be used to treat or prevent any disease or disorder characterized by aberrant TREM or TREML activity.

Examples of inflammatory, autoinflammatory, and autoimmune diseases and disorders that may be treated or prevented by way of the present method include, but are not limited to, systemic inflammatory response syndrome, sepsis, severe sepsis, septic shock, septicemia, primary and secondary macrophage activation syndrome, primary and secondary hemophagocytic lymphohistiocytosis, cytokine release syndrome, cytokine storm syndrome, tumor lysis syndrome, Adult Onset Still's disease, ischemia-reperfusion injuries such as those resulting from percutaneous or surgical revascularization, embolic diseases, vasospastic diseases, vasculitic diseases, peripheral vascular diseases, low-perfusion states, stroke or myocardial infarction, acute respiratory distress syndrome, asthma, allergic diseases, anaphylaxis, encephalitis, inflammatory bowel disease including but not limited to Crohn's disease and ulcerative colitis, chronic obstructive pulmonary disease (COPD), interstitial lung diseases, non-specific interstitial pneumonia, cryptogenic organizing pneumonia, allergic disorders, pulmonary fibrosis, undifferentiated spondyloarthropathy, undifferentiated arthropathy, inflammatory osteolysis, psoriasis, cerebral malaria, arthritis, such as rheumatoid arthritis, folliculitis, impetigo, granulomas, lipoid pneumonias, vasculitis, osteoarthritis, neurodegenerative diseases and chronic inflammation resulting from chronic viral or bacterial infections, insulin-dependent diabetes mellitus (or type 1 diabetes), type II diabetes, metabolic syndrome, obesity-associated syndromes, insulin autoimmune syndrome, rheumatoid arthritis, psoriatic arthritis, chronic lyme arthritis, systemic lupus erythematosus, mixed connective tissue disease, undifferentiated connective tissue disease, multiple sclerosis, inflammatory bowel disease including Crohn's disease and ulcerative colitis, celiac disease, autoimmune thyroid disease including Hashimoto's thyroiditis and Graves' disease, autoimmune myocarditis, autoimmune hepatitis, pemphigus, anti-tubular basement membrane disease (kidney), familial dilated cardiomyopathy, hypertrophic cardiomyopathy, Taktsubo cardiomyopahy, Goodpasture's syndrome, Sjogren's syndrome, myasthenia gravis, polyendocrine failure, vitiligo, peripheral neuropathy, autoimmune polyglandular syndrome type I, acute glomerulonephritis, adult-onset idiopathic hypoparathyroidism (AOIH), alopecia totalis, Addison's disease, chronic beryllium syndrome, ankylosing spondylitis, juvenile dermatomyositis, polychondritis, scleroderma, regional enteritis, distal ileitis, granulomatous enteritis, regional ileitis, and terminal ileitis, pancreatitis from any etiology, amyotrophic lateral sclerosis, ankylosing spondylitis, autoimmune aplastic anemia, autoimmune hemolytic anemia, idiopathic thrombocytopenic purpura (ITP), Behcet's disease, Celiac disease, chronic active hepatitis, CREST syndrome and systenic sclerosis, dermatomyositis, polymyositis, necrotizing myositides, eosinophilia-myalgia syndrome, eosinophilic granulomatous polyangiitis, ANCA-associated vasculitides, ANCA-negative vasculitides, epidermolisis bullosa acquisita (EBA), giant cell arteritis, Goodpasture's syndrome, Guillain-Barr syndrome, hemochromatosis, Henoch-Schonlein purpura, idiopathic IgA nephropathy, insulin autoimmune syndrome, juvenile rheumatoid arthritis, Lambert-Eaton syndrome, linear IgA dermatosis, narcolepsy, neonatal lupus syndrome (NLE), periodic fever, nephrotic syndrome, pemphigoid, pemphigus, primary sclerosing cholangitis, non-alcoholic steatotic hepatitis, hepatic cirrhosis, psoriasis, rapidly-progressive glomerulonephritis (RPGN), Reiter's syndrome, stiff-man syndrome, capillary leak syndrome, osteoarthritis, graft rejection, such as allograft rejection, atherosclerosis from any etiology, and others.

In some embodiments, compositions of the present invention are co-administered with other therapeutics or prophylactics relevant to the diseases including, but not limited to, anti-inflammatory agents, non-steroidal anti-inflammatory drugs (NSAIDs), immunosuppressive agents, steroids, biological therapies, and the like.

In one aspect, the invention provides a method for preventing in a subject, a disease or disorder, by administering to the subject a composition described herein. Subjects at risk for a disease or disorder identified by, for example, any diagnostic or prognostic assay. Administration of a prophylactic agent can occur prior to the manifestation of symptoms characteristic of the disease or disorder, such that the disease or disorder is prevented or delayed in its progression.

Another aspect of the invention pertains to methods of modulating expression or activity of one or more TREM or TREML proteins for therapeutic purposes. The modulatory method of the invention involves contacting a cell or subject with a composition described herein that modulates the expression or activity of one or more TREM or TREML proteins.

In some embodiments, the method comprises administering an effective amount of a composition described herein to a subject diagnosed with, suspected of having, or at risk for developing an inflammatory, autoinflammatory, or autoimmune disease or disorder. In some aspects, the composition is contacted to a cell or tissue where a condition is present or at risk of developing. In one embodiment, the composition is administered systemically to the subject.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

In some embodiments, the composition of the invention is administered before, during, or after another treatment of the disease or disorder. In one embodiment, the composition of the invention is administered before, during, or after administration of antibiotics and use of vasopressors and mechanical ventilation for the treatment of sepsis.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are administered by i.v. injection.

The pharmaceutical compositions useful for practicing the invention may be administered to deliver a dose of from 1 ng/kg/day and 100 mg/kg/day. In one embodiment, the invention envisions administration of a dose which results in a concentration of the compound of the present invention from 1 µM and 10 µM in a mammal.

Typically, dosages which may be administered in a method of the invention to a mammal range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. In one embodiment, the dosage will vary from about 1 µg to about 50 mg per kilogram of body weight of the mammal. In one embodiment, the dosage will vary from about 1 mg to about 10 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

The administration of a nucleic acid or peptide inhibitor of the invention to the subject may be accomplished using gene therapy. Gene therapy, which is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide codifying the polypeptide of the invention can be designed for direct insertion or by insertion through liposomes or viral vectors (for example, adenoviral or retroviral vectors) in the cell. In one embodiment, the cell is a cell of the germinal line, an embryonic cell or egg cell or derived from the same. In some instances, the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

Diagnostic Methods

In one aspect, the present invention provides a method of detecting or diagnosing a subject as having an inflammatory, autoinflammatory, or autoimmune disorder by detecting the presence or abundance of one or more ligands of one or more TREM or TREML protein in a sample of a subject. For example, in certain embodiments, the method comprises detecting the presence or abundance of mitochondria derived or released from necroptotic cell in a sample of a subject. In one embodiment, the method comprises the presence or abundance of cardiolipin in a sample of a subject. In one embodiment, the detection of the presence of cardiolipin or mitochondria derived or released from necroptotic cells identifies the subject as having an inflammatory, autoinflammatory, or autoimmune disorder treatable by way of the inhibitors of one or more TREM or TREML proteins, as described elsewhere herein.

In certain embodiments, the method comprises detection of mitochondria in a sample of a subject. In some embodiments, mitochondria are isolated from a sample using a suitable purification or separation technique, including but not limited to differential centrifugation, immunoprecipitation, fluorescent-activated cell sorting (FACS) or magnetic-activated cell sorting (MACS). In some embodiments, the method comprises detecting one or more mitochondrial-associated markers, such as a mitochondrial membrane protein or phospholipids. Exemplary mitochondrial associated markers that can be used to detect the presence or abundance of mitochondria in the sample include, but is not limited to, VDAC, TOMM20, TOMM22, TOMM40, HSP60, COXIV, cytochrome C, and the like. In some embodiments, the method comprises administering a reagent or dye that specifically stains mitochondria. Exemplary reagents and dyes to stain mitochondria, include but are not limited to, JC-1, JC-9, rhodamine 123, MitoTracker™, and the like.

In certain embodiments, the method comprises detecting the presence or abundance of mitochondria released or derived from necroptotic cells. For example, in one embodiment, the method comprises detecting a marker specific for mitochondria released or derived from necroptotic cells, thereby distinguishing these mitochondria from those associated with healthy, viable, or apoptotic cells.

In certain embodiments, the method comprises detecting a necroptotic cell, via detection of cardiolipin or mitochondria released or derived from a necroptotic cell, by way of the labeled protein reagents described elsewhere herein. For example, as described elsewhere herein, labeled protein reagents comprising the ectodomain of a TREM or TREML protein can be used to detect cardiolipin or mitochondria released or derived from a necroptotic cell can be used in a variety of assays, including, but not limited to, flow cytometry, mass cytometry, CITE-seq, REAP-seq, fluorescence microscopy, immunohistochemistry, immunoassays, and the like.

In one embodiment, the method comprises detecting the presence or abundance of cardiolipin in a sample of a subject. In certain embodiments, cardiolipin is detected by way of an antibody, antibody fragment, or probe that specifically binds to cardiolipin, which can be used in various immunoassays such as Western blot, immunoprecipitation, and radioimmunoassay. The proteins analyzed may be localized intracellularly (most commonly an application of fluorescence microscopy or immunohistochemistry) or extracellularly (most commonly an application of immunoassays such as ELISA).

Biological samples may be of any biological tissue or fluid. Frequently the sample will be a "clinical sample" which is a sample derived from a patient. The biological sample may contain any biological material suitable for detecting the desired biomarkers, and may comprise cellular and/or non-cellular material obtained from the individual. Exemplary biological samples include, but is not limited to, blood, serum, plasma, saliva, urine, lymph, tears, cerebral spinal fluid, sputum, urogenital discharge, purulent discharge, stool, intra-articular (joint) fluid, and the like.

In certain embodiments, the level of the markers described herein (e.g., cardiolipin or mitochondria derived or released from necroptotic cells), is compared to the level of the markers in a control group. For example, in one embodiment, the level of the markers is compared to the level of the makers in an individual or population of healthy subjects. In one embodiment, the level of the markers is compared to the level of the markers in an individual or population of subjects known to not have an inflammatory, autoinflammatory, or autoimmune disorder. In one embodiment, the level of the markers is compared to the level of the markers in an individual or population of subjects with a known severity of an inflammatory, autoinflammatory, or autoimmune disorder. In one embodiment, the level of the markers is compared to the level of the markers in a sample obtained from a subject at an earlier time point. For example, in one embodiment, the level of the markers is compared to the level of the markers in a sample obtained before a treatment regimen is initiated.

As described below, comparison of the level of the markers of the sample to be tested with those of the controls can be used to diagnose an inflammatory, autoinflammatory, or autoimmune disorder; monitor the progression of an inflammatory, autoinflammatory, or autoimmune disorder; identify or classify a subject has being suitable for a specific treatment or evaluate the response to treatment. In some instances, the control groups are only for the purposes of establishing initial cutoffs or thresholds for the assays of the invention. Therefore, in some instances, the systems and methods of the invention can diagnose, monitor or classify an inflammatory, autoinflammatory, or autoimmune disorder without the need to compare with a control group.

Accordingly, the present invention features methods for identifying subjects having an inflammatory, autoinflammatory, or autoimmune disorder, or who are at risk of developing an inflammatory, autoinflammatory, or autoimmune disorder, including those subjects who are asymptomatic or only exhibit non-specific indicators of an inflammatory, autoinflammatory, or autoimmune disorder by detection of the biomarkers disclosed herein.

These biomarkers are also useful for monitoring subjects undergoing treatments and therapies for an inflammatory, autoinflammatory, or autoimmune disorder; and for selecting or modifying therapies and treatments that would be efficacious in subjects having an inflammatory, autoinflammatory, or autoimmune disorder, wherein selection and use of such treatments and therapies slow the progression of an inflammatory, autoinflammatory, or autoimmune disorder, or prevent its onset. In certain embodiments, the biomarkers are used for determining whether a subject has an inflammatory, autoinflammatory, or autoimmune disorder treatable by way of exemplary therapeutics or prophylactics relevant to the disorders including, but not limited to, anti-inflammatory agents, non-steroidal anti-inflammatory drugs (NSAIDs), immunosuppressive agents, steroids, biological therapies, and the like. In certain embodiments, the biomarkers are used for determining whether a subject has TREM or TREML-associated inflammation that can be treated by way of an inhibitor of one or more TREM or TREML proteins, as described elsewhere herein.

The invention provides improved methods for the diagnosis and prognosis of an inflammatory, autoinflammatory, or autoimmune disorder. The risk of developing an inflammatory, autoinflammatory, or autoimmune disorder can be assessed by measuring one or more of the biomarkers described herein, and comparing the measured values to comparator values, reference values, or index values. Such a comparison can be undertaken with mathematical algorithms or formula in order to combine information from results of multiple individual biomarkers and other parameters into a single measurement or index. Subjects identified as having an increased risk of an inflammatory, autoinflammatory, or autoimmune disorder can optionally be selected to receive treatment regimens, such as prophylactic or therapeutic agents, including but not limited to one or more of the inhibitors of one or more TREM or TREML proteins described herein.

Identifying a subject before they develop an inflammatory, autoinflammatory, or autoimmune disorder enables the selection and initiation of various therapeutic interventions or treatment regimens in order to delay, reduce or prevent that subject's conversion to a disease state. Monitoring the levels of at least one biomarker also allows for the course of treatment of an inflammatory, autoinflammatory, or autoimmune disorder to be monitored. For example, a sample can be provided from a subject undergoing treatment regimens or therapeutic interventions for an inflammatory, autoinflammatory, or autoimmune disorder. Samples can be obtained from the subject at various time points before, during, or after treatment.

The present invention also provides methods for identifying agents for treating or preventing an inflammatory, autoinflammatory, or autoimmune disorder that are appropriate or otherwise customized for a specific subject. In this regard, a test sample from a subject, exposed to a therapeutic agent or a drug, can be taken and the level of one or more biomarkers can be determined. The level of one or more biomarkers can be compared to a sample derived from the subject before and after treatment, or can be compared to samples derived from one or more subjects who have shown improvements in risk factors as a result of such treatment or exposure.

Reagents

In one aspect, the present invention provides compositions and methods for detection of necroptotic cells or mitochondria released or derived from necroptotic cells. For example, in certain embodiments, the composition comprises a protein reagent comprising an ectodomain of one or more TREM or TREML protein, as described elsewhere herein, wherein the peptide binds to necroptotic cells or mitochondria released or derived from necroptotic cells. In certain embodiments, the protein reagent is fused to, or otherwise conjugated to, a detectable label to allow for the protein to be used in a suitable assay, including but not limited to, immunoassays, flow cytometry, mass cytometry, CITE-seq, immunofluorescence, and the like. Exemplary labels include, but is not limited to, fluorescent molecules (e.g., green fluorescent protein, phycoerythrin, Allophycocyanin, etc.), fluorescent dyes, stable metal isotopes, oligonucleotide barcodes, protein tags (e.g., streptavidin, Histag), enzymes (e.g., HRP, luciferase, etc.), chemical haptens (e.g., biotin, DNP, PEG, azides, alkynes (for click chemistry)) and the like.

In one embodiment, the protein reagent comprises an ectodomain of a TREM or TREML protein. In some embodiments, the protein reagent comprises a fragment or variant of an ectodomain of a TREM or TREML protein. The composition may comprise, for example, an ectodomain from any isoform of a TREM or TREML protein ectodomain, including an ectodomain of a TREM or TREML protein from any organism. In one embodiment, the composition comprises a full-length ectodomain of a TREM or TREML protein. In one embodiment, the composition comprises a recombinant ectodomain of a TREM or TREML protein.

In one embodiment, the protein reagent comprises an ectodomain of human TREML4. For example, in one embodiment, the ectodomain of human TREML4 comprises the amino acid sequence of SEQ ID NO: 1, or a variant or fragment thereof.

In some embodiments, the protein reagent comprises an ectodomain of human TREML4 comprising one or more mutations. For example, in some embodiments, the protein reagent comprises an ectodomain of human TREML4 comprising one or more mutations at one more residues selected from: T35, L65, L66, K71, S69, K71, K78, K86, T95, G156, and H160, in relation to full-length wild-type human TREML4.

In some embodiments, the protein reagent comprises an ectodomain of human TREML4 comprising one or more mutations selected from: T35X, L65X, L66X, S69X, K71X, K78X, K86X, T95X, G156X, and H160X, in relation to full-length wild-type human TREML4, where X is any amino acid. In some embodiments, the protein reagent comprises an ectodomain of human TREML4 comprising one or more mutations selected from: T35S, L65R, L66V, S69T, K71E, K78E, K86D, T95K, G156E, and H160D, in relation to full-length wild-type human TREML4.

In one embodiment, the protein reagent comprises an ectodomain of human TREML4 comprising a K86X mutation, where X is any amino acid. In one embodiment, the protein reagent comprises an ectodomain of human TREML4 comprising a K86D mutation in relation to full-length wild-type human TREML4 (hTREML4-K86D). For example, in one embodiment, the ectodomain of hTREML4-K86D comprises the amino acid sequence of SEQ ID NO: 2, or a variant or fragment thereof.

In one embodiment, the protein reagent comprises an ectodomain of human TREML4 comprising a L65X mutation, where X is any amino acid. In one embodiment, the protein reagent comprises an ectodomain of human TREML4 comprising a L65R mutation in relation to full-length wild-type human TREML4 (hTREML4-L65R). For example, in one embodiment, the ectodomain of hTREML4-L65R comprises the amino acid sequence of SEQ ID NO: 3, or a variant or fragment thereof.

In one embodiment, the protein reagent comprises an ectodomain of human TREML4 comprising a K71X mutation, where X is any amino acid. In one embodiment, the protein reagent comprises an ectodomain of human TREML4 comprising a K71E mutation in relation to full-length wild-type human TREML4 (hTREML4-K71E). For example, in one embodiment, the ectodomain of hTREML4-K71E comprises the amino acid sequence of SEQ ID NO: 4, or a variant or fragment thereof.

In one embodiment, the protein reagent comprises an ectodomain of human TREML4 comprising a T95K mutation, where X is any amino acid. In one embodiment, the protein reagent comprises an ectodomain of human TREML4 comprising a T95K mutation in relation to full-length wild-type human TREML4 (hTREML4-T95K). For example, in one embodiment, the ectodomain of hTREML4-T95K comprises the amino acid sequence of SEQ ID NO: 5, or a variant or fragment thereof.

In one embodiment, the protein reagent comprises an ectodomain of human TREML4 comprising a T35X mutation, where X is any amino acid. In one embodiment, the protein reagent comprises an ectodomain of human TREML4 comprising a T35S mutation in relation to full-length wild-type human TREML4 (hTREML4-T35S). For example, in one embodiment, the ectodomain of hTREML4-T35S comprises the amino acid sequence of SEQ ID NO: 6, or a variant or fragment thereof.

In one embodiment, the protein reagent comprises an ectodomain of human TREML4 comprising a L66X mutation, where X is any amino acid. In one embodiment, the protein reagent comprises an ectodomain of human TREML4 comprising a L66V mutation in relation to full-length wild-type human TREML4 (hTREML4-L66V). For example, in one embodiment, the ectodomain of hTREML4-T35S comprises the amino acid sequence of SEQ ID NO: 7, or a variant or fragment thereof.

In one embodiment, the protein reagent comprises an ectodomain of human TREML4 comprising a S69X mutation, where X is any amino acid. In one embodiment, the protein reagent comprises an ectodomain of human TREML4 comprising a S69T mutation in relation to full-length wild-type human TREML4 (hTREML4-S69T). For example, in one embodiment, the ectodomain of hTREML4-S69T comprises the amino acid sequence of SEQ ID NO: 8, or a variant or fragment thereof.

In one embodiment, the protein reagent comprises an ectodomain of human TREML4 comprising a K78X mutation, where X is any amino acid. In one embodiment, the protein reagent comprises an ectodomain of human TREML4 comprising a K78E mutation in relation to full-length wild-type human TREML4 (hTREML4-K78E). For example, in one embodiment, the ectodomain of hTREML4-K78E comprises the amino acid sequence of SEQ ID NO: 9, or a variant or fragment thereof.

In one embodiment, the protein reagent comprises an ectodomain of human TREML4 comprising a G156X mutation, where X is any amino acid. In one embodiment, the protein reagent comprises an ectodomain of human TREML4 comprising a G156E mutation in relation to full-length wild-type human TREML4 (hTREML4-G156E). For example, in one embodiment, the ectodomain of hTREML4-G156E comprises the amino acid sequence of SEQ ID NO: 10, or a variant or fragment thereof.

In one embodiment, the protein reagent comprises an ectodomain of human TREML4 comprising a H160X mutation, where X is any amino acid. In one embodiment, the protein reagent comprises an ectodomain of human TREML4 comprising a H160D mutation in relation to full-length wild-type human TREML4 (hTREML4-H160D). For example, in one embodiment, the ectodomain of hTREML4-H160D comprises the amino acid sequence of SEQ ID NO: 11, or a variant or fragment thereof.

In one embodiment, the protein reagent comprises an ectodomain of human TREML4 comprising a triple mutation of L65R/K71E/K86D in relation to full-length wild-type human TREML4 (hTREML4-L65R/K71E/K86D). For example, in one embodiment, the ectodomain of hTREML4-L65R/K71E/K86D comprises the amino acid sequence of SEQ ID NO:12, or a variant or fragment thereof.

In one embodiment, the protein reagent comprises an ectodomain of human TREML4 comprising a quadruple mutation of in relation to full-length wild-type human TREML4 L65R/K71E/K86D/T95K (hTREML4-L65R/K71E/K86D/T95K). For example, in one embodiment, the ectodomain of hTREML4-L65R/K71E/K86D/T95K comprises the amino acid sequence of SEQ ID NO: 13, or a variant or fragment thereof.

In one embodiment, the protein reagent comprises an ectodomain of murine TREML4. For example, in one embodiment, the ectodomain of murine TREML4 comprises the amino acid sequence of SEQ ID NO: 14, or a variant or fragment thereof. In one embodiment, the protein reagent comprises an ectodomain of human TREM2. For example, in one embodiment, the ectodomain of TREM2 comprises the amino acid sequence of SEQ ID NO: 15, or a variant or fragment thereof.

In one embodiment, the protein reagent comprises an ectodomain of human TREM1. For example, in one embodiment, the ectodomain of TREM1 comprises: the amino acid sequence of SEQ ID NO: 16, or a variant or fragment thereof.

In one embodiment, the protein reagent comprises an ectodomain of human TREML1. For example, in one embodiment, the ectodomain of TREML1 comprises the amino acid sequence of SEQ ID NO: 17, or a variant or fragment thereof.

In one embodiment, the protein reagent comprises an ectodomain of human TREML2. For example, in one embodiment, the ectodomain of TREML2 comprises the amino acid sequence of SEQ ID NO: 18, or a variant or fragment thereof.

In some embodiments, the protein reagent comprises a fusion protein comprising a first domain and a second domain. In one embodiment, the first domain comprises an ectodomain of one or more TREM or TREML proteins. For example, in one embodiment, the first domain comprises an ectodomain provided by at least one of SEQ ID NOS: 1-18, or a variant or fragment thereof.

In one embodiment, the second domain comprises a peptide that enhances stability or half-life of the fusion protein. For example, in one embodiment, the second domain comprises at least one region of an immunoglobulin, human serum albumin (HSA), or a peptide or antibody fragment that binds to immunoglobulin, HSA, the erythrocyte cell surface, or the neonatal Fc receptor. In one embodiment, the second domain comprises a fragment or variant of at least one region of an immunoglobulin. For example, in one embodiment, the second domain comprises an Fc region of an immunoglobulin. Exemplary immunoglobulins include, but is not limited to, IgG1, IgG2, IgG3, IgG4, IgM, IgA, IgE, and IgD. In certain embodiments, the peptide comprises an immunoglobulin comprising one or more mutations to reduce effector function, as described, for example in, Lo et al., 2017, J Biol Chem, 292(9): 3900-3908; Bolt et al., 1993, Eur J Immunol, 23: 403-411; Leabman et al., 2013, MAbs, 5: 896-903; Tao and Morrison, 1989, J Immunol, 143: 2595-2601; Walker et al., 1989, Biochem J, 347-353; Alegre et al., 1992, J Immunol, 148: 3461-3468; Xu et al., 2000, Cell Immunol, 200: 16-26; Rother et al., 2007, Nat Biotechnol, 25: 1256-1264; An et al., 2009, MAbs, 1: 572-579; Vafa et al., 2014, Methods, 65: 114-126, and Wang et al., 2018, Protein Cell, 9(1): 63-73; each of which are incorporated by reference herein in their entireties.

In one embodiment, the second domain comprises the Fc domain of human IgG1. For example, in one embodiment, the Fc domain of wild-type human IgG1 comprises the amino acid sequence of SEQ ID NO: 19, or a variant or fragment thereof.

In one embodiment, the second domain comprises a fragment or variant of the Fc domain of human IgG1. In some embodiments, the Fc domain is mutated to reduce Fc effector functions through Fc receptors or complement. For example, in certain embodiments the Fc domain of IgG1 is mutated at one or more of D265, N297, L234, L235, P331, P329 or K332 to reduce effector function. For example, in certain embodiments the Fc domain of IgG1 is mutated at one or more of D265A, N297Q, N297A, N297G, L234A, L234F, L235E, L235A, K322A, P329G, and P331S. The peptide may comprise IgG1 having one or more mutations in the Fc region as described, for example in, Lo et al., 2017, J Biol Chem, 292(9): 3900-3908; Bolt et al., 1993, Eur J Immunol, 23: 403-411; Leabman et al., 2013, MAbs, 5: 896-903; Tao and Morrison, 1989, J Immunol, 143: 2595-2601; Walker et al., 1989, Biochem J, 347-353; Alegre et al., 1992, J Immunol, 148: 3461-3468; Xu et al., 2000, Cell Immunol, 200: 16-26; Rother et al., 2007, Nat Biotechnol, 25: 1256-1264; An et al., 2009, MAbs, 1: 572-579; and Vafa et al., 2014, Methods, 65: 114-126.

In certain embodiments, the peptide comprises an IgG1 domain comprising one or more mutations in its hinge region to reduce effector function, as described for example in Dall'Acqua et al., 2006, J Immunol, 177(2): 1129-1138, which is incorporated by reference herein in its entirety.

In one embodiment, the second domain comprises a fragment or variant of the Fc domain of human IgG2. In some embodiments, the Fc domain is mutated to reduce Fc effector functions through Fc receptors or complement. For example, in certain embodiments the Fc domain of IgG2 is mutated at one or more of H268, V309, A330, P331, V234, G237, P238, and H268 to reduce effector function. For example, in certain embodiments the Fc domain of IgG1 is mutated at one or more of H268Q, V309I, A330S, P331S, V234A, G237A, P238S, and H268A.

In one embodiment, the second domain comprises a fragment or variant of the Fc domain of human IgG4. In some embodiments, the Fc domain is mutated to reduce Fc effector functions through Fc receptors or complement. For example, in certain embodiments the Fc domain of IgG4 is mutated at one or more of F234 and L235 to reduce effector function. For example, in certain embodiments the Fc domain of IgG1 is mutated at one or more of F234A and L235A. In one embodiment, the second domain comprises and IgG2/IgG4 cross isotype.

For example, in some embodiments, the second domain comprises an aglycosylated variant of the Fc domain of human IgG1. In some embodiments, the second domain comprises a variant of the Fc domain of human IgG1 where N297 is mutated to prevent glycosylation. In some embodiments, the second domain comprises a variant of the Fc domain of human IgG1 comprising an N297Q, N297A, or N297G mutation, relative to wildtype full-length IgG1.

For example, in one embodiment, the second domain comprises a variant of the Fc domain of human IgG1, wherein the variant comprises an N297Q mutation. For example, in one embodiment, the variant of the Fc domain comprises the amino acid sequence of SEQ ID NO: 20, or a variant or fragment thereof.

For example, in one embodiment, the second domain comprises a variant of the Fc domain of human IgG1, wherein the variant comprises an N297A mutation. For example, in one embodiment, the variant of the Fc domain comprises the amino acid sequence of SEQ ID NO: 21, or a variant or fragment thereof.

For example, in one embodiment, the second domain comprises a variant of the Fc domain of human IgG1, wherein the variant comprises an N297G mutation. For example, in one embodiment, the variant of the Fc domain comprises the amino acid sequence of SEQ ID NO: 22, or a variant or fragment thereof.

In some embodiments, the second domain comprises a fragment or variant of an Fc domain containing mutations that confer enhanced half-life in serum. In some embodiments, the mutations increase the association of the Fc domain with the neonatal Fc receptor (FcRn). In some embodiments, those mutations include the "YTE" triple mutation (M252Y/S254T/T256E). In some embodiments, those mutations include the "LS" double mutation (M428L/N434S).

In some embodiments, the second domain comprises a fragment or variant of an Fc domain that contains combinations of mutations that both remove or reduce effector functions and also extend the half-life of the Fc domain. For example, the combination of the N297A mutation with the YTE triple mutation ("AYTE"), or the combination of the N297A mutation with the LS double mutation ("ALS").

In some embodiments, the fusion protein comprises a linker domain separating the first domain and second domain. In one embodiment, the linker domain comprises GGGSGGSGGSGGS (SEQ ID NO: 23). In another embodiment, the linker domain comprises one or more repeats of the 5-mer (GGGGS (SEQ ID NO: 24). In another embodiment, the linker domain comprises AAA.

In some embodiments, the fusion protein comprises a secretory leader sequence. For example in one embodiment, the leader sequence comprises the H7 leader peptide derived from the leader sequence of the IgG heavy chain. In one embodiment, the leader sequence comprises MEFGLSWVFLVALFRGVQS (SEQ ID NO: 25). Other exemplary leader peptides include, but are not limited to, the IgG kappa light chain, the IgG lambda light chain, the leader peptide from Human Serum Albumin, and the leader peptide from Interleukin-2.

In one embodiment, the fusion protein comprises a first domain comprising human TREML4 and a second domain comprising a variant of the Fc domain of human IgG1, wherein the Fc domain comprises a glycosylation site N297Q mutation. For example, in one embodiment, the fusion protein comprises the amino acid sequence of SEQ ID NO: 26, or a variant or fragment thereof.

In one embodiment, the fusion protein comprises a first domain comprising hTREML4-K86D and a second domain comprising a variant of the Fc domain of human IgG1, wherein the Fc domain contains a glycosylation site N297Q mutation. For example, in one embodiment, the fusion protein comprises the amino acid sequence of SEQ ID NO: 27, or a variant or fragment thereof.

In one embodiment, the fusion protein comprises a first domain comprising hTREML4-L65R and a second domain comprising a variant of the Fc domain of human IgG1, wherein the Fc domain contains a glycosylation site N297Q mutation. For example, in one embodiment, the fusion protein comprises the amino acid sequence of SEQ ID NO: 28, or a variant or fragment thereof.

In one embodiment, the fusion protein comprises a first domain comprising hTREML4-K71E and a second domain comprising a variant of the Fc domain of human IgG1, wherein the Fc domain contains a glycosylation site N297Q mutation. For example, in one embodiment, the fusion protein comprises the amino acid sequence of SEQ ID NO: 29, or a variant or fragment thereof.

In one embodiment, the fusion protein comprises a first domain comprising hTREML4-T95K and a second domain comprising a variant of the Fc domain of human IgG1, wherein the Fc domain contains a glycosylation site N297Q mutation. For example, in one embodiment, the fusion protein comprises the amino acid sequence of SEQ ID NO: 30, or a variant or fragment thereof.

In one embodiment, the fusion protein comprises a first domain comprising hTREML4-T35S and a second domain comprising a variant of the Fc domain of human IgG1, wherein the Fc domain contains a glycosylation site N297Q mutation. For example, in one embodiment, the fusion protein comprises the amino acid sequence of SEQ ID NO: 31, or a variant or fragment thereof.

In one embodiment, the fusion protein comprises a first domain comprising hTREML4-L66V and a second domain comprising a variant of the Fc domain of human IgG1, wherein the Fc domain contains a glycosylation site N297Q mutation. For example, in one embodiment, the fusion protein comprises the amino acid sequence of SEQ ID NO: 32, or a variant or fragment thereof.

In one embodiment, the fusion protein comprises a first domain comprising hTREML4-S69T and a second domain comprising a variant of the Fc domain of human IgG1, wherein the Fc domain contains a glycosylation site N297Q mutation. For example, in one embodiment, the fusion protein comprises the amino acid sequence of SEQ ID NO: 33, or a variant or fragment thereof.

In one embodiment, the fusion protein comprises a first domain comprising hTREML4-K78E and a second domain comprising a variant of the Fc domain of human IgG1, wherein the Fc domain contains a glycosylation site N297Q mutation. For example, in one embodiment, the fusion protein comprises the amino acid sequence of SEQ ID NO: 34, or a variant or fragment thereof.

In one embodiment, the fusion protein comprises a first domain comprising hTREML4-G156E and a second domain comprising a variant of the Fc domain of human IgG1, wherein the Fc domain contains a glycosylation site N297Q mutation. For example, in one embodiment, the fusion protein comprises the amino acid sequence of SEQ ID NO: 35, or a variant or fragment thereof.

In one embodiment, the fusion protein comprises a first domain comprising hTREML4-H160D and a second domain comprising a variant of the Fc domain of human IgG1, wherein the Fc domain contains a glycosylation site N297Q mutation. For example, in one embodiment, the fusion protein comprises the amino acid sequence of SEQ ID NO: 36, or a variant or fragment thereof.

In one embodiment, the fusion protein comprises a first domain comprising hTREML4-L65R/K71E/K86D and a second domain comprising a variant of the Fc domain of human IgG1, wherein the Fc domain contains a glycosylation site N297Q mutation. For example, in one embodiment, the fusion protein comprises the amino acid sequence of SEQ ID NO: 37, or a variant or fragment thereof.

In one embodiment, the fusion protein comprises a first domain comprising hTREML4-L65R/K71E/K86D/T95K and a second domain comprising a variant of the Fc domain of human IgG1, wherein the Fc domain contains a glycosylation site N297Q mutation. For example, in one embodiment, the fusion protein comprises the amino acid sequence of SEQ ID NO: 38, or a variant or fragment thereof.

In one embodiment, the fusion protein comprises a first domain comprising murine TREML4 and a second domain comprising a variant of the Fc domain of human IgG1, wherein the Fc domain comprises a glycosylation site N297Q mutation. For example, in one embodiment, the fusion protein comprises the amino acid sequence of SEQ ID NO: 39, or a variant or fragment thereof.

In one embodiment, the fusion protein comprises a first domain comprising human TREM2 and a second domain comprising a variant of the Fc domain of human IgG1, wherein the Fc domain comprises a glycosylation site N297Q mutation. For example, in one embodiment, the fusion protein comprises the amino acid sequence of SEQ ID NO: 40, or a variant or fragment thereof.

In one embodiment, the fusion protein comprises a first domain comprising human TREM1 and a second domain comprising a variant of the Fc domain of human IgG1, wherein the Fc domain comprises a glycosylation site N297Q mutation. For example, in one embodiment, the fusion protein comprises the amino acid sequence of SEQ ID NO: 41, or a variant or fragment thereof.

In one embodiment, the fusion protein comprises a first domain comprising human TREML1 and a second domain comprising a variant of the Fc domain of human IgG1, wherein the Fc domain comprises a glycosylation site N297Q mutation. For example, in one embodiment, the fusion protein comprises the amino acid sequence of SEQ ID NO: 42, or a variant or fragment thereof.

In one embodiment, the fusion protein comprises a first domain comprising human TREML2 and a second domain comprising a variant of the Fc domain of human IgG1, wherein the Fc domain comprises a glycosylation site N297Q mutation. For example, in one embodiment, the fusion protein comprises the amino acid sequence of SEQ ID NO: 43, or a variant or fragment thereof.

The invention should also be construed to include any form of a protein variant having substantial homology to an amino acid sequence disclosed herein. In one embodiment, a protein variant is at least about 50%, 70%, 80%, 85%, 86%, 87%, 88%, 89%, 90%, 91%, 92%, 93%, 94%, 95%, 96%, 97%, 98%, or 99% homologous to an amino acid sequence disclosed herein.

The invention should also be construed to include any form of a fragment having a substantial length of an amino acid sequence disclosed herein. In one embodiment, a fragment is at least about 50%, 70%, 80%, 85%, 86%, 87%, 88%, 89%, 90%, 91%, 92%, 93%, 94%, 95%, 96%, 97%, 98%, or 99% of the length of an amino acid sequence disclosed herein.

The invention should also be construed to include any form of a fragment of a protein variant, having both substantial homology to and a substantial length of an amino acid sequence disclosed herein. In one embodiment, a fragment of a protein variant at least about 50%, 70%, 80%, 85%, 86%, 87%, 88%, 89%, 90%, 91%, 92%, 93%, 94%, 95%, 96%, 97%, 98%, or 99% homologous to an amino acid sequence disclosed herein, and is at least about 50%, 70%, 80%, 85%, 86%, 87%, 88%, 89%, 90%, 91%, 92%, 93%, 94%, 95%, 96%, 97%, 98%, or 99% of the length of an amino acid sequence disclosed herein.

In certain embodiments, the protein reagent comprises a detectable label. For example, in one embodiment, the protein reagent comprises a protein described above fused to, or otherwise conjugated to, a detectable label. In one embodiment, the detectable label comprises an imaging agent, contrast agent, detection agent, or the like.

Imaging agents are materials that allow the reagent to be visualized after exposure to a cell or tissue. Visualization includes imaging for the naked eye, as well as imaging that requires detecting with instruments or detecting information not normally visible to the eye, and includes imaging that requires detecting of photons, sound or other energy quanta. Examples include stains, vital dyes, fluorescent markers, radioactive markers, enzymes or plasmid constructs encoding markers or enzymes. Suitable imaging agents include, for example, fluorescent molecules, labeled antibodies, labeled avidin:biotin binding agents, colloidal metals (e.g., gold, silver), reporter enzymes (e.g., horseradish peroxidase), superparamagnetic transferrin, second reporter systems (e.g., tyrosinase), and paramagnetic chelates. Many materials and methods for imaging and targeting that may be used are provided in the Handbook of Targeted delivery of Imaging Agents, Torchilin, ed. (1995) CRC Press, Boca Raton, Fla.

In some embodiments, the imaging agent is a magnetic resonance imaging contrast agent. Examples of magnetic resonance imaging contrast agents include, but are not limited to, 1,4,7,10-tetraazacyclododecane-N,N',N'',N'''-tetracetic acid (DOTA), diethylenetriaminepentaacetic (DTPA), 1,4,7,10-tetraazacyclododecane-N,N',N'',N'''-tetraethylphosphorus (DOTEP), 1,4,7,10-tetraazacyclododecane-N,N',N''-triacetic acid (DOTA) and derivatives thereof (see U.S. Pat. Nos. 5,188,816, 5,219,553, and 5,358,704). In some embodiments, the imaging agent is an X-Ray contrast agent. X-ray contrast agents already known in the art include a number of halogenated derivatives, especially iodinated derivatives, of 5-amino-isophthalic acid.

In certain embodiments, the detectable label comprises a label used in flow cytometry assays which can be used, for example, to detect necroptotic cells or mitochondria released or derived from necroptotic cells. For example, in certain embodiments, the detectable label comprises a fluorescent molecule, dye, or the like. In one embodiment, the detectable label of the reagent comprises a biomolecule that interacts with a secondary labeled biomolecule to form a detectable complex (i.e., biotin-streptavidin complex).

In certain embodiments, the detectable label comprises a label used in mass cytometry assays which can be used, for example, to detect necroptotic cells or mitochondria released or derived from necroptotic cells. For example, in certain embodiments, the detectable label comprises a stable metal isotope thereby allowing for detection of the reagent in a mass cytometry assay.

In certain embodiments, the detectable label comprises a fluorescent label, such as fluorescent molecule or dye, used in fluorescent microscopy to detect necroptotic cells or mitochondria released or derived from necroptotic cells. Exemplary fluorescent labels include, but is not limited to GFP, eGFP, YFP, CFP, RFP, mCherry, fluorescein, rhodamine, eosin, Texas red, Oregon green, lucifer yellow, cyanine and derivatives thereof, Alexa Fluor family of labels, and the like.

In certain embodiments, the detectable label comprises an oligonucleotide barcode used in Cellular Indexing of Transcriptomes and Epitopes by Sequencing (CITE-seq) (Stoeckius et al., 2017, Nature Methods, 14: 865-868) to detect necroptotic cells or mitochondria released or derived from necroptotic cells. For example, in some embodiments, the detectable label comprises an oligonucleotide that is detected by various DNA or RNA sequencing techniques, where detection of the oligonucleotide indicates that the reagent has bound to necroptotic cells or mitochondria released or derived from necroptotic cells in a sample.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: TREML4 and TREM2 Ectodomains Reduce Inflammation

The TREML4 gene has recently been identified to be a key regulator of inflammation by amplifying the signals from the Toll Like Receptors (TLRs) that recognize pathogen-associated molecular patterns (PAMPS). These pathways are major drivers of inflammatory processes that mediate diseases such as sepsis and inflammatory and autoimmune diseases and represent major targets for drug development. Though the function of TREML4 has been established in genetic models, there are no pharmacologic agents against this pathway. The first described pharmacologic tool (TREML4-Fc) that can manipulate the TREML4 receptor is described herein, and it is a remarkably potent therapeutic in a murine models of endotoxemia and sepsis.

To date, no therapeutic agents have provided a significant benefit in sepsis patients. A potential reason for these clinical failures is that sepsis is a multi-factorial disease that activates several inflammatory pathways at once, resulting in production of a myriad of downstream pro-inflammatory effectors. Agents that target just one of these pathways (e.g., TLR4/endotoxin) or one of these mediators (e.g., TNF-alpha) are unlikely to be effective. It was desired to identify master regulatory nodes of inflammation that could globally control immune responses to systemic infections.

As macrophages are major producers of inflammatory cytokines and can express the full complement of TLRs, RNAseq experiments comparing bone marrow-derived macrophages stimulated sequentially with TLR agonists were performed, which identified TREML4 as a gene uniquely upregulated in hyper-activated macrophages. These in vitro studies were validated in macrophages taken ex vivo from animal models of sepsis. Together, these studies revealed TREML4 as a significantly upregulated gene in macrophages from septic mice.

TREML4 is a single-pass transmembrane protein of the TREM-like family that couples to the stimulatory DAP12 signaling subunit. The experiments presented herein were conducted to examine whether TREML4 could be a key feed-forward gene in the acute phase of inflammation.

It was examined whether the TREML4 ectodomain could function as an inhibitory decoy receptor of TREML4 signaling. Therefore, both the human and murine TREML4 ectodomains, as well as the human TREM1, TREML1, TREM2, TREML2 ectodomains, comprising the Ig-like superfamily fold fused to the Fc fragment of human IgG1 with an N297Q mutation, were cloned and expressed. The aglycosylated hIgG1 N297Q variant was used so that the Fc portion would confer only an enhancement of serum half-life without conferring unwanted effector functions to the fusion protein. Other mutations such as N297A or N297G would have similar effectiveness, as would additional mutations of Fc that alter its binding to Fc receptor and/or complement. The amino acid sequences of the constructs are as provided elsewhere herein.

The TREM ectodomain Fc fusion proteins were expressed in expi293 cells (Thermo Scientific) by transient transfection using the manufacturer's instructions and purified by protein A chromatography (FIG. 1A). Analytical size exclusion chromatography showed the majority of the protein was monodisperse eluted at the expected molecular weight for the dimeric Fc-fusion protein (FIG. 1B). Yields were in excess of 10 mg/L of expression medium and proteins were buffer-exchanged into sterile phosphate buffered saline using a PD10 column (GE healthcare).

Figure 3:
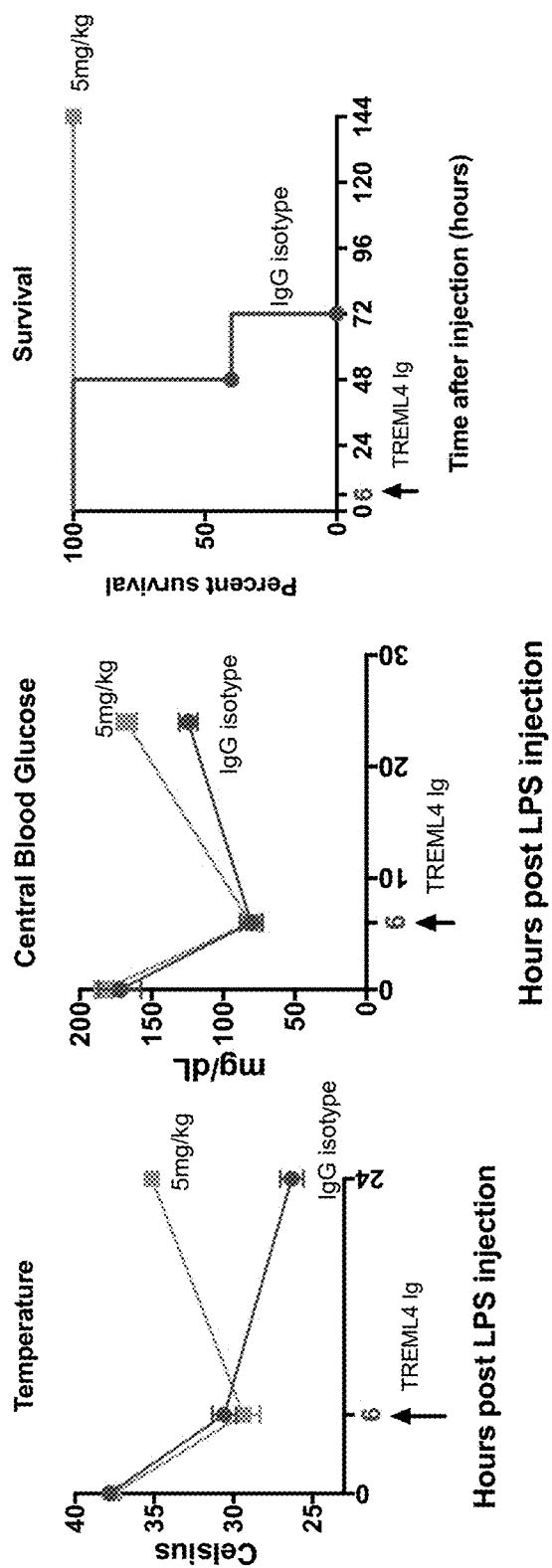
FIG. 3 depicts results from example experiments assessing whether late administration of mTREML4-Fc would be sufficient to rescue mice from LD100 doses of LPS. The Fc variant used was aglycosylated human IgG1 with the N297Q mutation. The data demonstrates that delayed administration of mTREML4-Fc protein rescues mice in lethal endotoxemia. Six hours after treatment of LD100 of LPS, mice were injected with 5 mg/kg mTREML4-Fc protein or human IgG1 FcN297Q variant by retro orbital injection. Blood glucose and body temperature were measured and recorded. Survival was monitored in every 24 h for 6 days and analyzed with Mantel-Haenzel Log Rank test.

To test its effectiveness in sepsis, the standard lipopolysaccharide (LPS) endotoxemia model was used. Lethal dose 100 (LD100) amounts of LPS were administered to 8-week old male mice intraperitoneally. First, the therapeutic activity of different dosages of mTREML4-Fc protein in mediating protection from LPS sepsis were determined (FIG. 2). Two hours later, after verification of known initial events in this model, including decrease in body temperature, locomotive activity, and decrease in plasma glucose, 1 mg/kg or 10 mg/kg (Experiment #1) or 5 mg/kg (Experiment #2) of mTREML4-Fc protein were administered intravenously. Body temperature, blood glucose and mortality were monitored. A dose-dependent effect was noted in the measured parameters. Then, it was tested if late administration of mTREML4-Fc would be sufficient to rescue mice from LD100 doses of LPS (FIG. 3). Five mg/kg administered was administered 6 hours after LPS injection, a time point where all known pathogenic mediators of mortality in this model had been systemically released. It was observed that late-administration was sufficient to reverse changes in body temperature, and rescue mice from LPS-mediated mortality.

Figure 4:
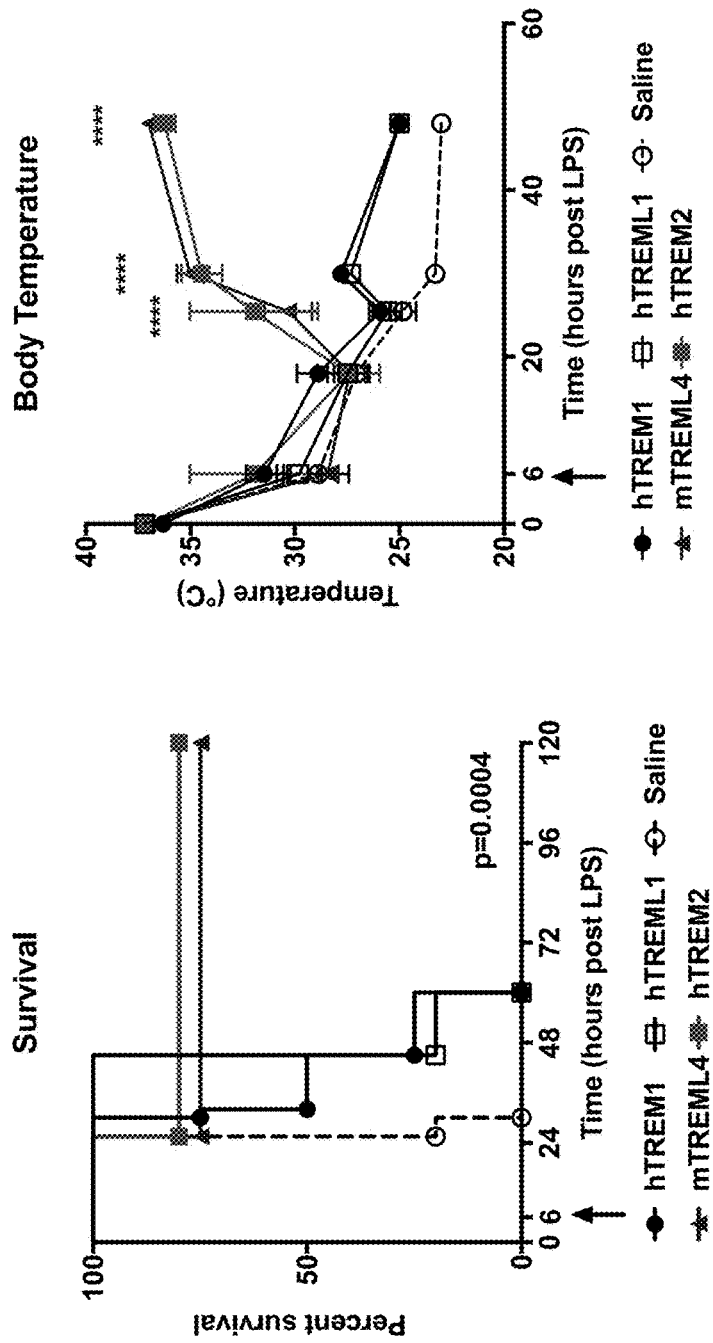
FIG. 4 depicts results from example experiments assessing the specificity of mTREML4, and the ability of hTREM1, hTREML1, and hTREM2 to rescue mice from endotoxemia. The Fc variant used was aglycosylated human IgG1 with the N297Q mutation. The experiments demonstrate the therapeutic activity of TREM-Fc proteins in lethal endotoxemia. Mice were randomly grouped and treated with LD100 of LPS. Six hours after LPS treatment, indicated TREM-Fc proteins were injected to mice in 10 mg/kg by retro orbital injection. Body temperature were measured and recorded by rectal temperature detector. Survival was monitored for 5 days and analyzed with the Mantel-Haenzel Log Rank test.

To determine the specificity of mTREML4, the ability of hTREM1, hTREML1, and hTREM2 to rescue mice from endotoxemia was also tested (FIG. 4). As with previous experiments, these proteins were delivered intravenously six hours after LPS was administered. hTREM2 and mTREML4, but not others, were capable of rescuing endotoxemic mice.

Figure 5:
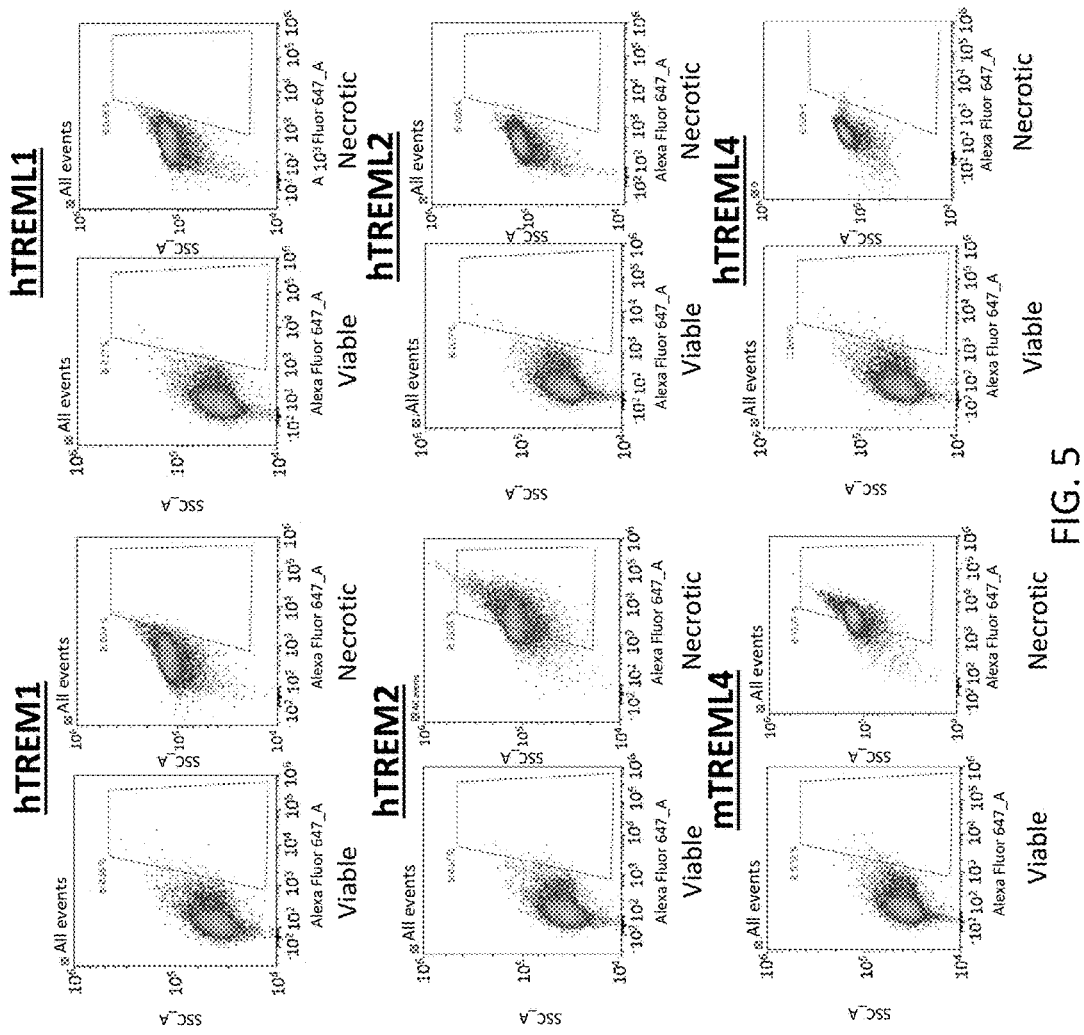
FIG. 5 depicts results of example experiments demonstrating the necrotic cell binding activity of hTREM1, hTREML1, hTREM2, hTREML2, mTREML4, and hTREML4. Necrotic cells were prepared by heat treatment of expi293 cells in 95° C. for 10 min. Indicated TREM-Fc proteins were added to necrotic cells at 10 µg/ml and incubated on ice for 30 min following by staining of anti-human IgG1-Alex Fluor647 secondary antibody. Data were acquired and analyzed by flow cytometer. Only hTREM2 and mTREML4 specifically bound necrotic cells and not viable cells.

Previous studies established that mTREML4 and mTREM2 bind necrotic cells (Hemmi et al., 2009, J Immunol, 182(3): 1278-1286). Thus, experiments were performed to investigate the ability of the present constructs to bind to necrotic cells. hTREM1, hTREML1, hTREM2, hTREML2, mTREML4, and hTREML4 were expressed as Fc (IgG1 N297Q) fusion proteins. The non-glycosylated/aglycosylated version of hIgG1 Fc (N297Q) was used for all studies unless explicitly noted otherwise. Assays were performed to assess their ability to bind necrotic expi293 cells prepared by heat treatment of 95° C. for 10 minutes. Binding was assessed by flow cytometry using an anti-human secondary antibody. As seen in FIG. 5, only hTREM2 and mTREML4 specifically bound necrotic, but not viable cells, correlating with their efficacy in the treatment of endotoxemia.

To understand why hTREML4 does not bind necrotic cells (and perhaps why it does not have efficacy in endotoxemia), the amino acid sequences of hTREML4, mTREML4, and hTREM2 were compared. Interestingly, it was observed that hTREML4 varied from mTREML4 at positions corresponding to Alzheimer's disease (AD) mutations in hTREM2: L65, K71, and K86 (FIG. 6). Constructs were designed where these positions in hTREML4 were mutated to the corresponding residues in mTREML4: L65R, K71E, K86D, and the triple mutant of L65R/K71E/K86D. In hTREM2, mutation of the equivalent position to T95 in hTREML4 to lysine is associated with decreased AD risk.

Therefore, constructs were also designed containing this mutation. As see in FIG. 7, when assessing the necrotic cell binding activity of these hTREML4 variants, it was observed that the K86D mutation was sufficient to confer necrotic cell binding activity. The necrotic binding activity was also observed in the L65R/K71E/K86D triple mutation in the L65R/K71E/K86D/T95K quadruple mutation, both of which contain K86D. These results thus reveal a novel and non-obvious mutation in hTREML4 (K86D) that confers necrotic cell binding activity.

Figure 7:
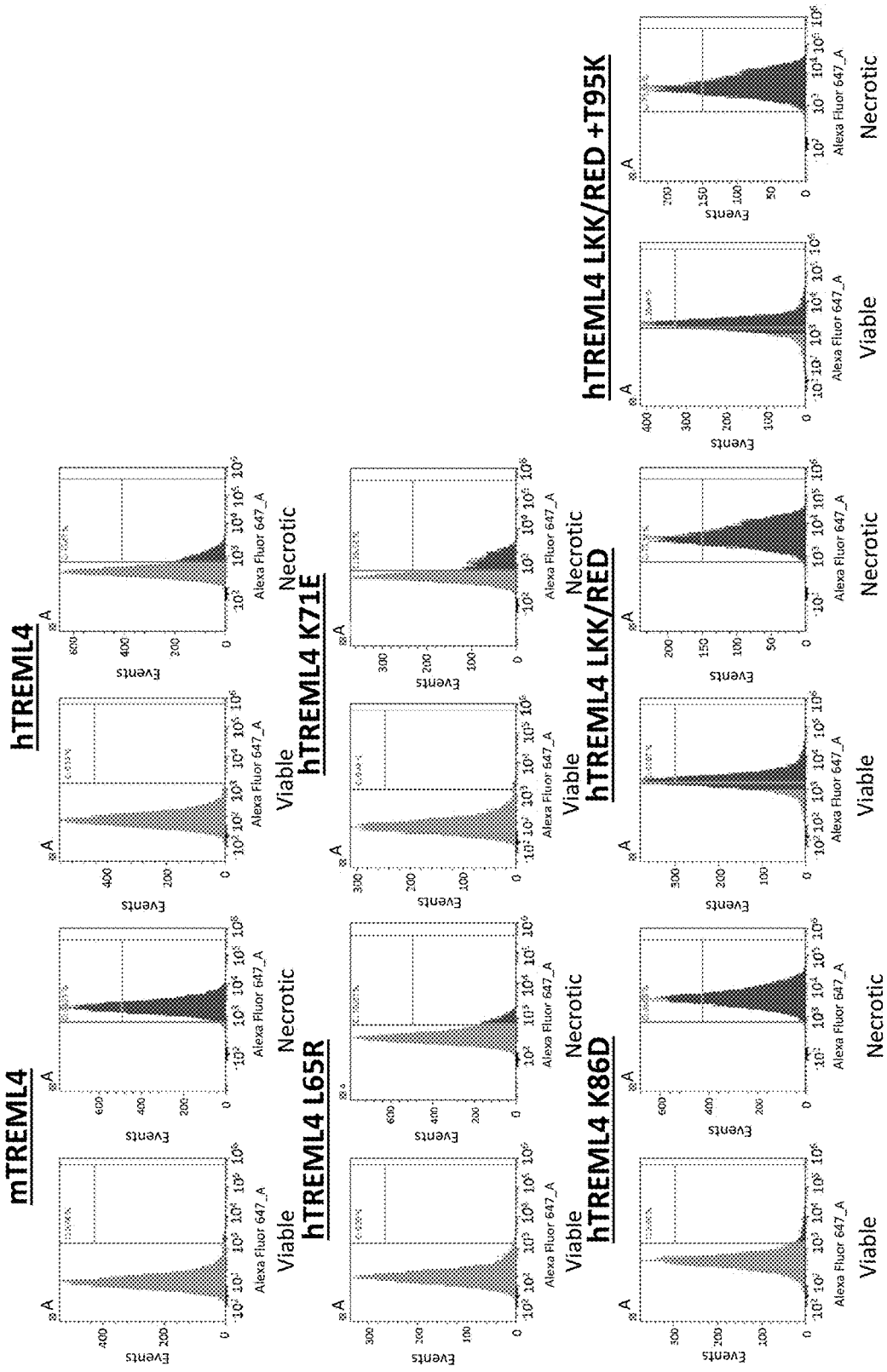
FIG. 7 depicts the results from example experiments demonstrating the necrotic cell binding of hTREML4 and its mutants L65R, K71E, K86D, and the triple mutant at all three of these positions (LKK/RED). Necrotic cells were prepared by heat treatment of expi293 cells in 95° C. for 10 min. TREM-Fc proteins were added to necrotic cells at 10 μg/ml and incubated on ice for 30 min following by staining of anti-human IgG1-Alex Fluor647 secondary antibody. Data was acquired and analyzed by flow cytometry.
Figure 8:
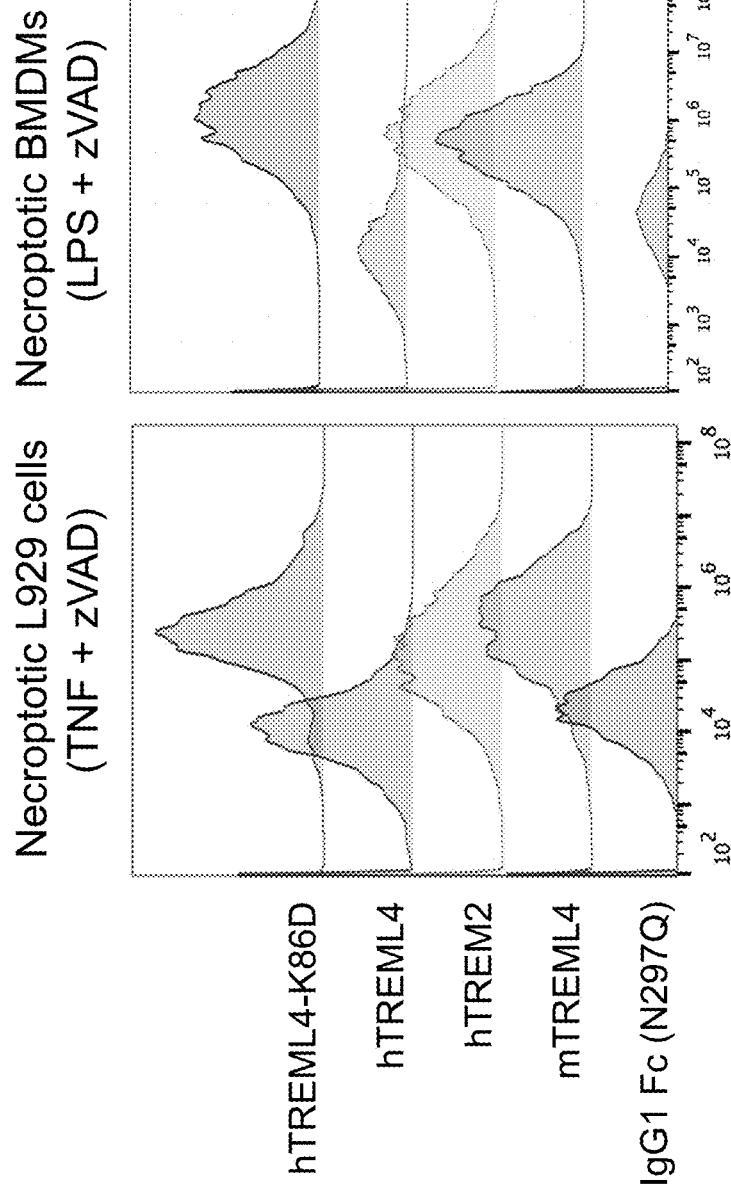
FIG. 8 depicts the results of example experiments demonstrating the cell binding of hTREML4, hTREML4-K86D, hTREM2, mTREML4, and an isotype control (Fc N297Q) to necroptotic L929 fibroblast cells and necroptotic mouse bone marrow derived macrophages (BMDMs). Necroptosis was induced by 50 ng/ml TNF+10 μM zVAD in L929 for 6 h or by 1 μg/ml LPS+25 μM zVAD in BMDMs for 12 h. Indicated TREM proteins were added to necroptotic cells in 10 μg/ml and incubated on ice for 30 min following by anti-human IgG1Fc secondary antibody staining for additional 15 min. Binding of TREM proteins to necroptotic cells were accessed and analyzed by flow cytometer. Consistent with the studies depicted in FIG. 5 and FIG. 7, hTREML4-K86D, hTREM2, and mTREML4 bind to necroptotic cells, establishing the generalizability of their necrotic cell binding activity.

Cells can undergo necrosis in several manners. One way is accidental cell death, such as through physical damage with temperature, osmolarity, force, pH, or chemical exposure. Cells can also undergo programmed inflammatory necrosis, such as through necroptosis, pyroptosis, or ferroptosis. In FIG. 5 and FIG. 7 it is demonstrated that mTREML4, hTREML4-K86D, and hTREM2 could bind heat-killed cells. To see if these same proteins could bind other necrotic cell types, similar cell binding studies were performed with necroptotic L929 fibroblast (treated with 50 ng/mL TNF-alpha+10 μM Z-VAD) and necroptotic mouse bone-marrow derived macrophages (BMDMs; treated with 25 μM Z-VAD+1 μg/mL LPS). As seen in FIG. 8, only hTREML4-K86D, hTREM2, and mTREML4, but not hTREML4 WT or control IgG1 Fc (N297Q) bound these necroptotic cells. These results thus establish that the TREM proteins bind diverse necrotic cells and that hTREML4 requires the K86D mutation to do so.

Figure 9:
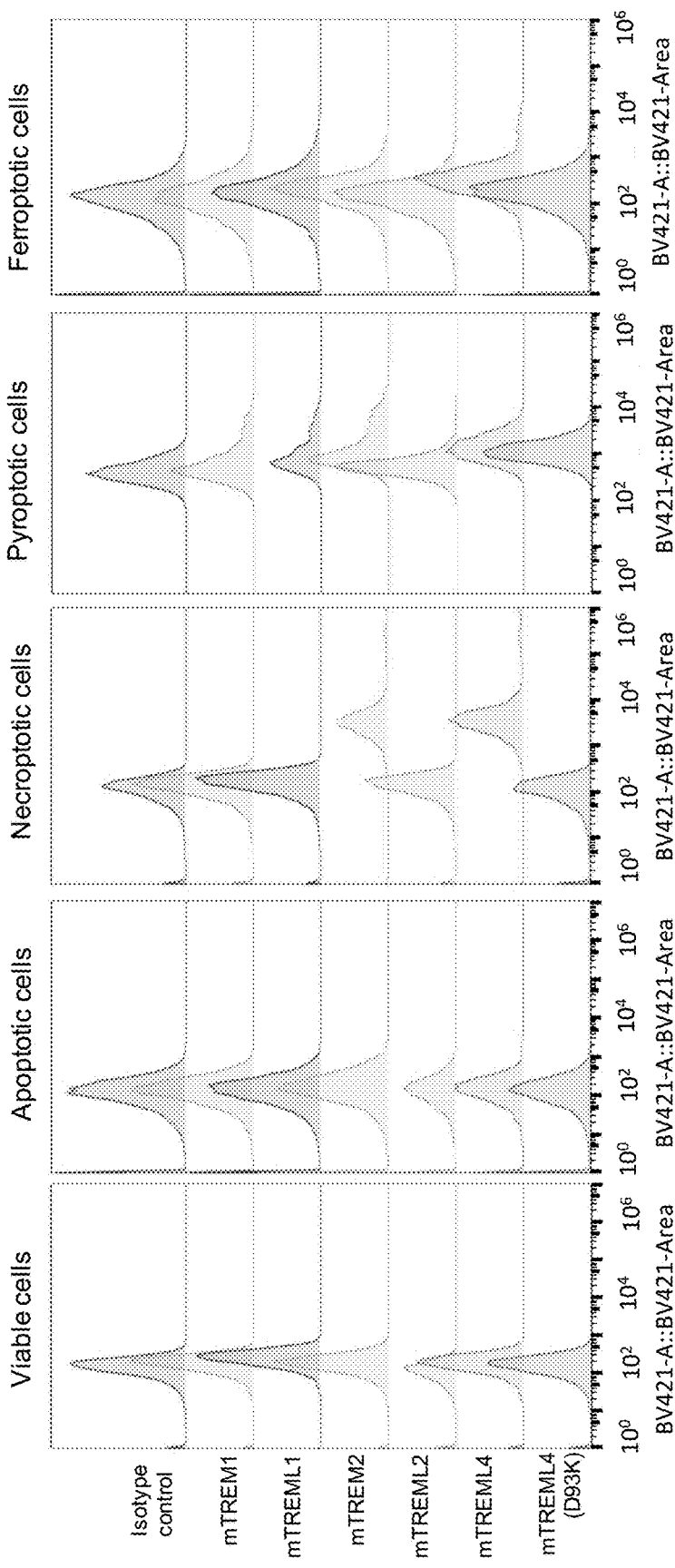
FIG. 9 depicts results of example experiments demonstrating the specificity of dead cell binding of murine TREM-Fc fusion proteins on viable, apoptotic, necroptotic, pyroptotic, and ferroptotic cells. L929 cells were induced with 50 ng/ml anti-CD95 for 16 h for apoptosis and induced with 50 ng/ml TNF+10 μM zVAD for 6 h for necroptosis. Pyroptosis was induced in mouse BMDM cells with 500 ng/ml LPS for 4 hours and then with 3 mM ATP treatment for 30 min. Ferroptosis was induced in L929 cells with 10 μM Erastin for 8 hours. All dead cells were collected and washed with FACS buffer and then incubated with indicated moue TREM proteins at 10 μg/ml on ice for 30 min following by anti-human IgG1Fc secondary antibody staining for additional 15 min. Binding of TREM proteins to necroptotic cells were accessed and analyzed by flow cytometer. mTREM2 and mTREML4 specifically bound necroptotic cells.
Figure 10:
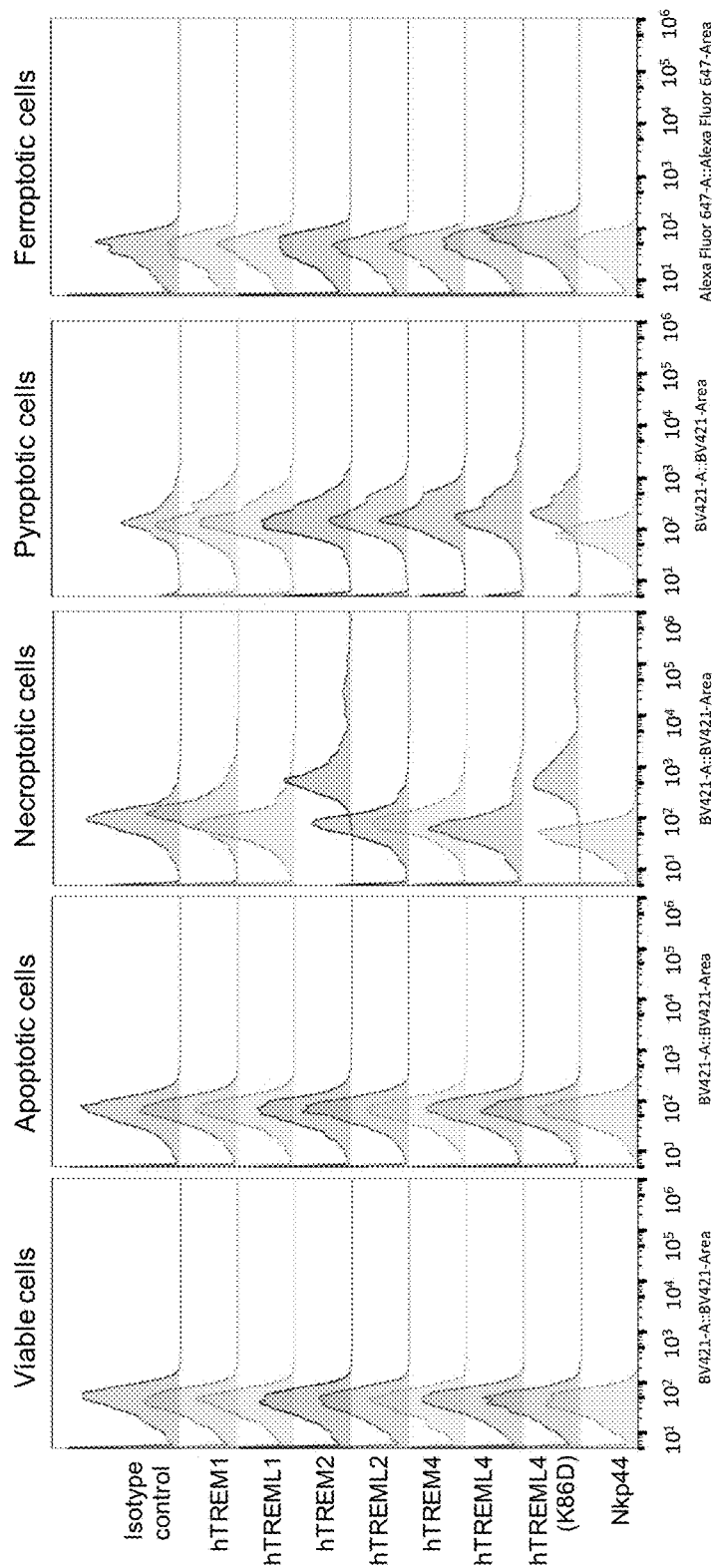
FIG. 10 depicts results of example experiments demonstrating the specificity of dead cell binding of human TREM-Fc fusion proteins on viable, apoptotic, necroptotic, and pyroptotic cells. Jurkat cells were induced with 2.5 μM Staurosporine for 16 h for apoptosis, with 10 μM Erastin for 8 h for ferroptosis or with 1 μg/ml LPS+3 mM ATP for 4 h for pyroptosis. FADD−/− Jurkat cells were induced necroptosis by 20 ng/ml TNF for 16 h. All dead cells were collected and washed with FACS buffer and then incubated with indicated human TREM proteins at 10 μg/ml on ice for 30 min following by anti-human IgG1Fc secondary antibody staining for additional 15 min. Binding of TREM proteins to necroptotic cells were accessed and analyzed by flow cytometry. hTREM2 and hTREML4-K86D specifically bound necroptotic cells.
Figure 11:
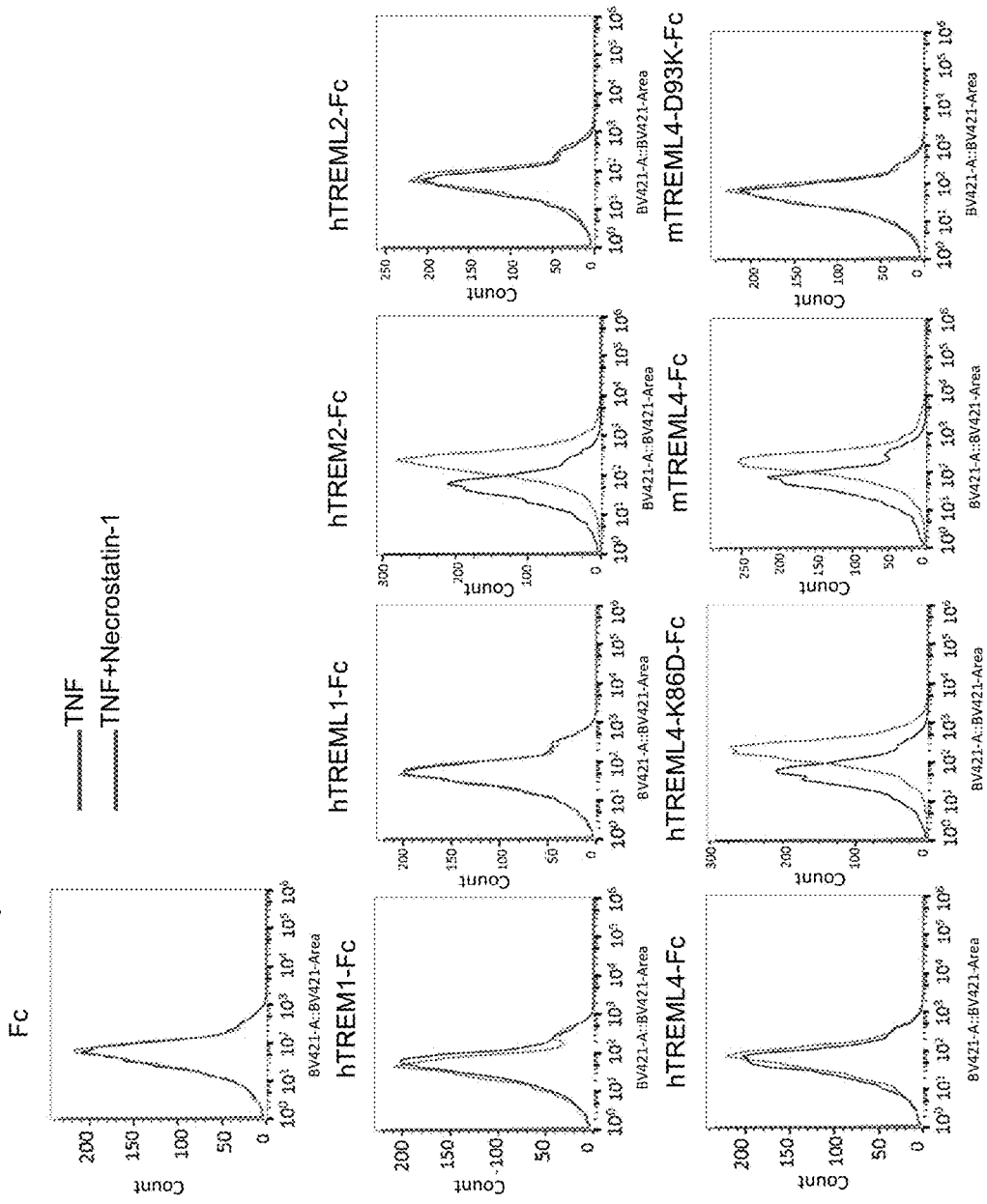
FIG. 11 depicts results of example experiments demonstrating the loss of hTREM2, hTREML4-K86D, and mTREML4 binding to dead cells when necroptosis is inhibited by the RIPK1 inhibitor necrostatin-1. FADD−/− Jurkat cells were treated with either 20 ng/ml human recombinant TNF for 24 h or with 20 ng/ml hTNF and 10 μM necrostatin-1 for 24 h. Cells were harvested and washed three times in FACS buffer and then incubated with indicated the TREM-Fc proteins at 10 μg/ml on ice for 30 min following by anti-human IgG1Fc secondary antibody staining for additional 15 min. Binding of TREM-Fc proteins to necroptotic cells were accessed and analyzed by flow cytometry.

Experiments were conducted to further characterize the spectrum of reactivity of the TREM and TREML family of receptors and different cell corpses. As seen in FIG. 9, of the murine TREM and TREML proteins, only mTREM2 and mTREML4 bound necroptotic cell corpses and not viable cells, apoptotic, pyroptotic, or ferroptotic cells. Mutation of mTREM4 D93K, making the reciprocal mutation to match hTREML4, abrogated binding to necroptotic cells. As seen in FIG. 10, only hTREM2 and hTREML4-K86D bound to necroptotic cells and not any other type of cell, including viable, apoptotic, and pyroptotic cells. Validating the specificity of the interaction on the necroptosis pathway, it was found that binding of hTREM2, hTREML4-K86D, and mTREML4 to necroptotic cells could be abrogated by inhibition of RIPK1 with necrostatin-1 during incubation with TNF-alpha+zVAD (FIG. 11).

Figure 12:
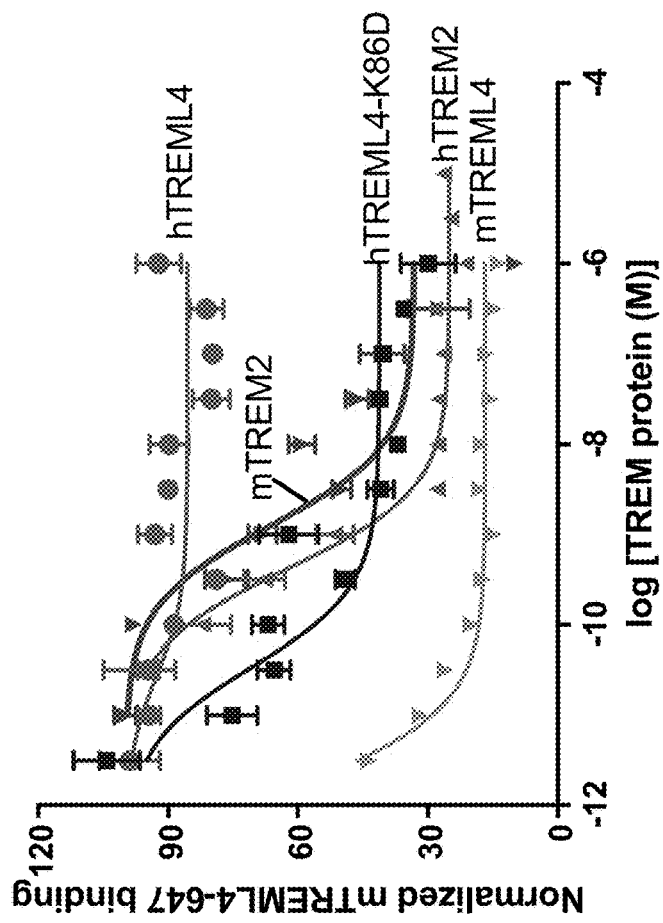
FIG. 12 depicts the results of example experiments using competition binding studies of mTREM2, mTREML4, hTREM2, hTREML4, and hTREML4-K86D with mTREML4-AlexaFluor647. Necrotic cells were prepared by heat treatment of expi293 cells in 95° C. for 10 min. Necrotic expi293 cells were stained with 0.2 μM Alex Fluor 647 conjugated mTREML4-Fc protein along with titrated concentrations of unlabeled mTREM2, mTREML4, hTREM2, hTREML4, or hTREML4-K86D. Cells were incubated on ice for 30 min and then washed three times with FACS buffer. Binding activity of MFI of mTREML4-AlexaFluor647 was acquired by flow cytometer and normalized to % max binding of each protein. mTREM2, mTREML4, hTREM2, and hTREML4-K86D potently inhibit binding of mTREML4-AlexaFluor647 indicating a shared binding epitope.

To determine if mTREML4, hTREM2, and hTREML4-K86D bind a shared epitope on necrotic cells, competition binding studies were performed. Briefly, mTREML4-Fc was conjugated with the amine-reactive dye AlexaFluor647-NHS (Thermo). Necrotic expi293 cells were stained with the mTREML4-Fc-647 conjugate and varying concentrations of unlabeled mTREML4, hTREM2, hTREML4, and hTREML4-K86D (all as Fc fusion proteins) were titrated. As seen in FIG. 12 mTREML4, hTREM2, and hTREML4-K86D, but not WT hTREML4 potently inhibited cell binding of mTREML4-Fc-647, indicating that they bind a shared epitope on necrotic cells.

Figure 13:
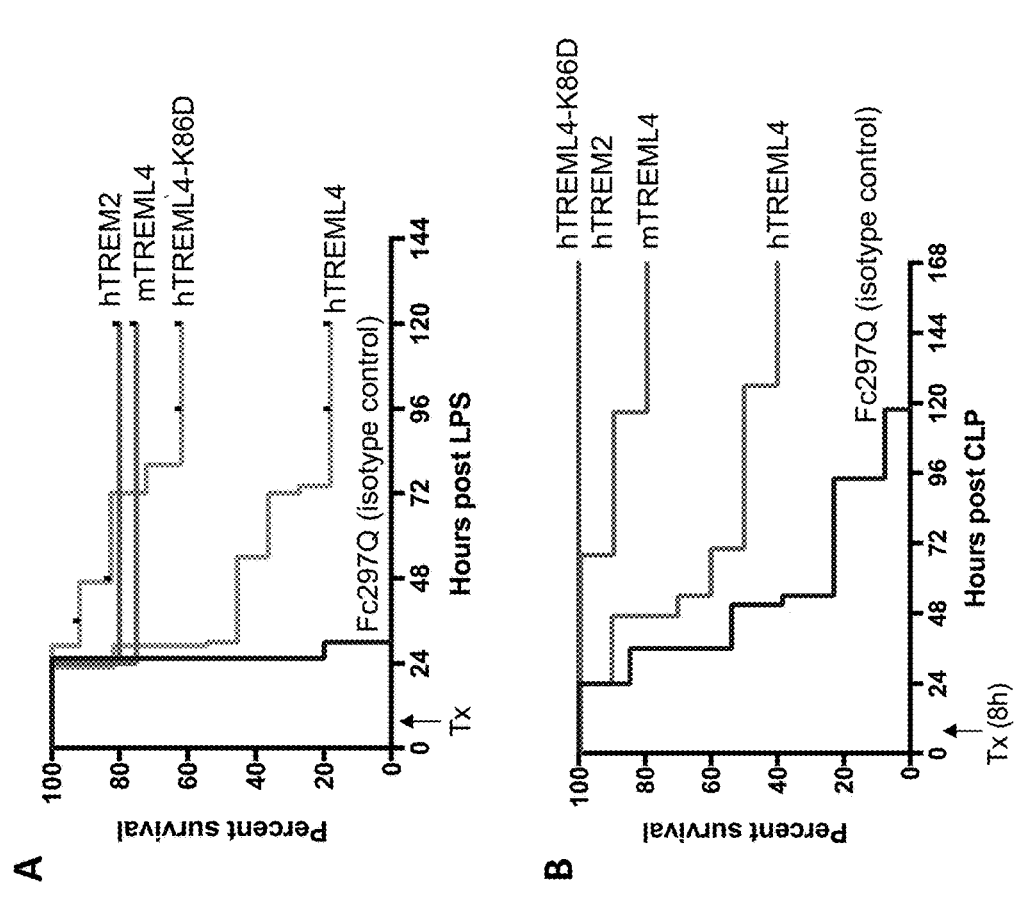
FIG. 13, comprising

Having established that the K86D mutation confers necrotic cell binding to hTREML4, it was sought to determine if that would confer efficacy to hTREML4 protein in the treatment of sepsis. Endotoxemia studies were performed by intraperitoneal administration of LPS, similar to those previous described, finding that hTREML4-K86D-Fc (hIgG1 N297Q) had similar efficacy as hTREM2-Fc or mTREML4-Fc at rescuing mice from sepsis, whereas WT hTREML4-Fc had only modest efficacy (FIG. 13A). To evaluate the efficacy of hTREML4-K86D-Fc in a high-bar sepsis model, experiments were performed using the Cecal Ligation Puncture (CLP) model of sepsis, where the cecum of mice is ligated with a suture and the ligated segment punctured with a needle to allow for escape of luminal contents into the peritoneum. Mice were treated with 5 mg/kg mTREML4-Fc (hIgG1 N297Q), WT hTREML4-Fc (hIgG1 N297Q), hTREML4-K86D-Fc (hIgG1 N297Q), or control IgG1 Fc (N297Q) 8 hours after cecal puncture. As seen in FIG. 13B, the IgG1 control treated mice experienced 100% fatality after 4-5 days. WT hTREML4-Fc (N297Q) afforded modest protection, preventing death in 40% of mice. mTREML4-Fc (N297Q) protected 80% of mice, and hTREML4-K86D-Fc (N297Q) protected 100% of mice. These results confirm the findings in the endotoxemia studies (FIG. 2-FIG. 4) and correlate the necrotic cell binding activity of TREM proteins with their efficacy in sepsis studies. Importantly, the K86D mutation of TREML4 that confers necrotic cell binding is required for efficacy and it is proposed that similar mutations that confer necrotic cell binding will have the same effect on efficacy.

Figure 14:
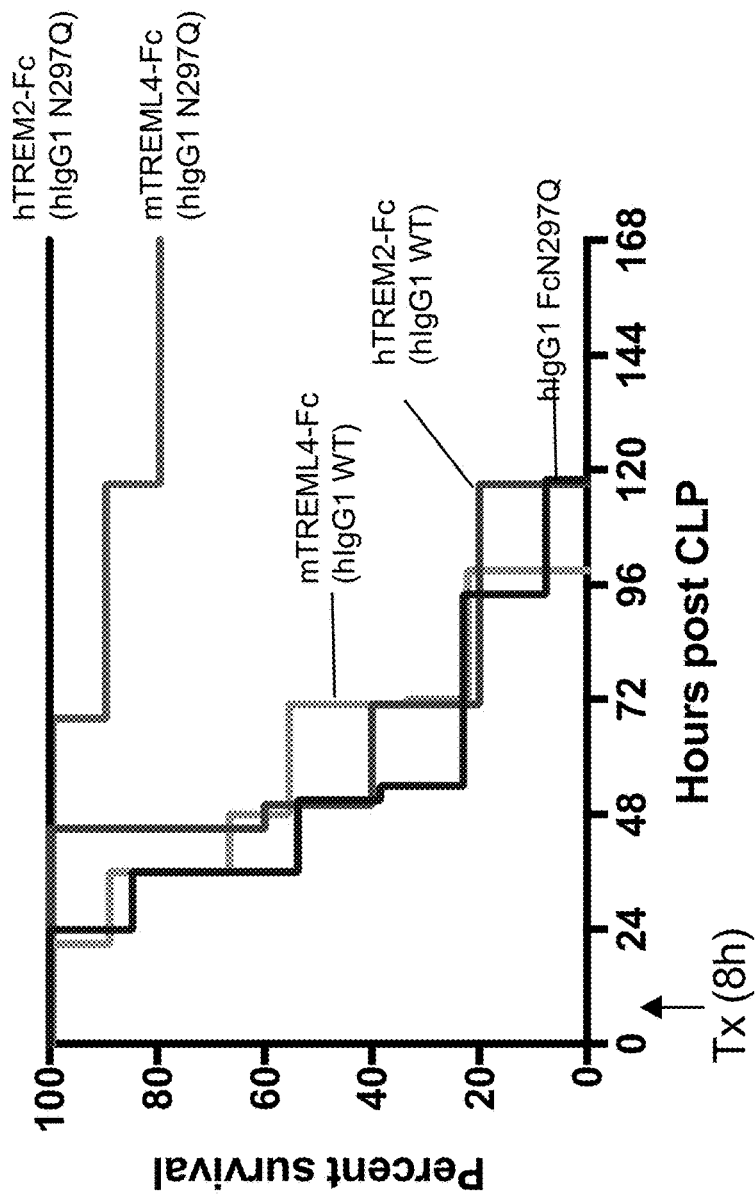
FIG. 14 depicts results from the example experiments assessing the ability of mTREML4-Fc and hTREM2-Fc with different Fc variants to rescue mice from experimental sepsis due to cecal ligation and puncture (CLP). The data demonstrates that Fc-effector functions negate the efficacy of TREM-Fc. Mice were randomly grouped and subjected to CLP with 1 cm cecal ligation and 25 G needle puncture. Mice received 10 mg/kg of the indicated TREM-Fc fusion proteins through intravenous injection in 8 h after CLP. Survival was monitored for 7 days. Survival comparisons were analyzed with the Mantel-Haenzel Log Rank test. Only aglyosylated Fc variants (human IgG1 N297Q) that lack effector functions through FcRs and complement protected mice in contrast to Fc variants with intact effector function (human IgG1).

The present studies consistently used an inactive Fc moiety, the Fc fragment of human IgG1 with a mutation of N297Q to remove the critical glycosylation required for Fc effector functions and complement binding. To see if Fc effector functions affected the efficacy of the TREM proteins in sepsis, the N297Q mutation back was reverted to the WT asparagine to restore Fc effector functions in the TREM-Fc fusion proteins. As seen in FIG. 14, only non-glycosylated (or "aglycosylated") Fc fusion proteins of hTREM2 and mTREML4 that lack Fc effector functions afforded protection in the CLP model, with hTREM2-Fc (N297Q) giving 100% protection and mTREML4-Fc (N297Q) providing 80% protection. Fc control treated mice and mice treated with hTREM2-Fc and mTREML4-Fc with WT IgG1 Fc sequences and intact Fc effector functions provided no protection from sepsis. This unexpected and non-obvious result clearly demonstrates that blockade of the TREM ligand is required for efficacy in sepsis, but that antibody effector functions negate this beneficial effect. It is proposed that similar mutations to inactivate Fc effector activity that alter its binding to Fc receptor and/or complement would have the same effect on TREM-Fc fusion protein efficacy in sepsis.

Figure 15:
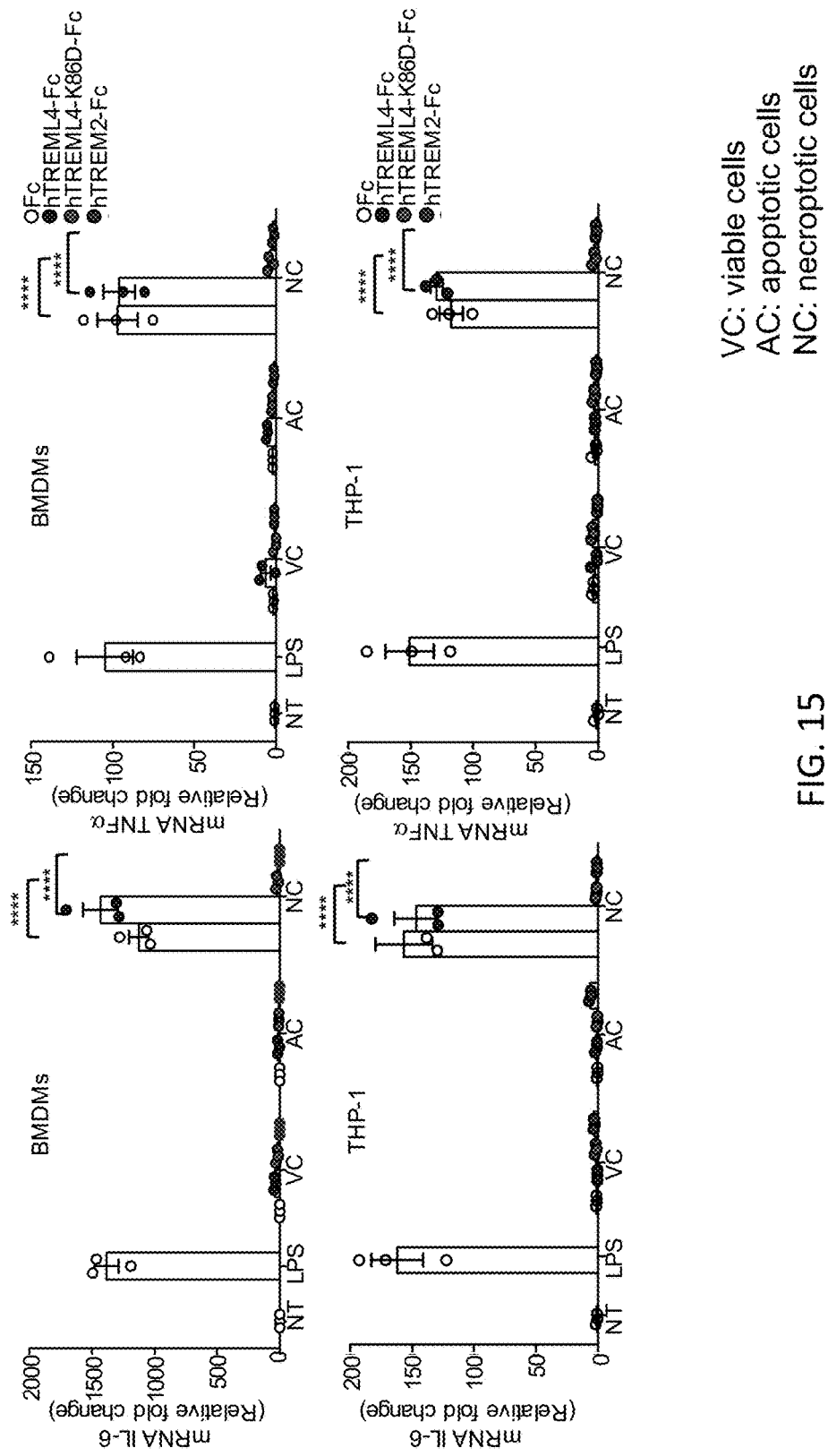
FIG. 15 depicts results of example experiments demonstrating that necroptotic, but not apoptotic cell corpses can activate inflammatory cytokine production which can be blocked by hTREM2-Fc and hTREML4-K86D-Fc. (Top row) qPCR analysis of IL-6 and TNFa in WT and TREM2−/− BMDMs ($1\times10^6$ cells/well) stimulated with 100 ng/ml LPS or 1 million indicated TREM-Fc-coated viable Jurkat cells, apoptotic Jurkat cells (Staurosporine) or necroptotic FADD−/− Jurkat cells (TNFa). (Bottom row) qPCR analysis of IL-6 and TNFa in WT and TREM2−/− THP-1 ($1\times10^6$ cells/well) stimulated with 100 ng/ml LPS or 1 million indicated TREM-Fc-coated viable L929 cells, apoptotic L929 cells (anti-CD95) or necroptotic L929 cells (TNFa+zVAD). Data show mean SEM combined from three independent experiments and analyzed by two-way ANOVA with multiple comparisons. *$P<0.05$, $P<0.01$, *$P<0.001$. The bars for each cell type are, from left to right: Fc, hTREML4-Fc, hTREML4-K86D-Fc, and hTREM2-Fc. The Fc variant used was aglycosylated human IgG1 with the N297Q mutation.

To mechanistically elucidate the effect of TREM2 blockade in the inflammatory response, co-culture in vitro studies were performed by incubating murine bone-marrow derived macrophages (BMDMs) with apoptotic or necroptotic cells. As seen in FIG. 15, addition of necroptotic (shikonin-treated), but not apoptotic (staurosporine-treated) cell corpses increased production of inflammatory cytokines such as IL-6 to a degree similar to LPS treatment. Incubation of the corpses with mTREML4-Fc or hTREML4-K86D-Fc, but not saline, isotype control hIgG1 Fc (N297Q), or WT hTREML4-Fc, abrogated the inflammatory effect. These results indicate that necroptotic cell corpses activate macrophages and that pharmacologic blockade of the TREM-TREM ligand interaction can reverse this effect.

Figure 16:
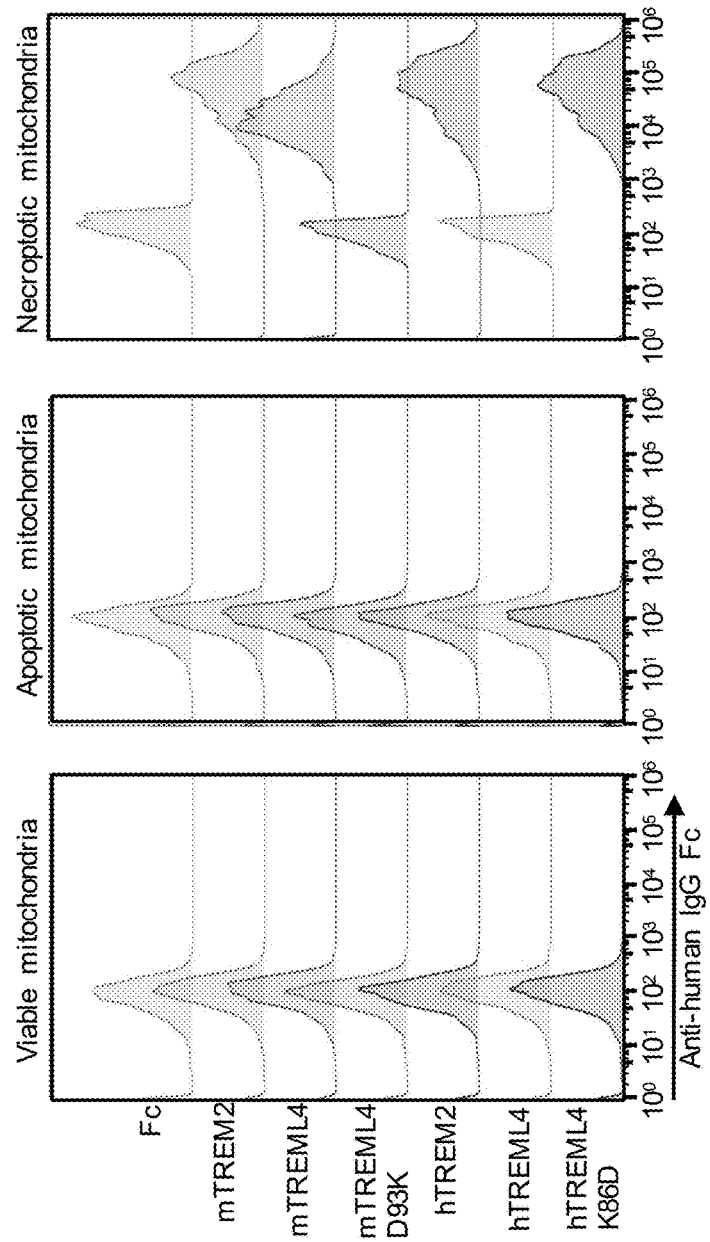
FIG. 16 depicts results of example experiments demonstrating that TREM2, mTREML4, hTREML4-K86D, but not hTREML4 WT, bind mitochondria isolated from necroptotic cells. L929 cells were induced with 50 ng/ml anti-CD95 for 16 h for apoptosis and with 50 ng/nl TNF+10 µM zVAD for 6 h for necroptosis. Mitochondria were isolated from viable, apoptotic and necroptotic L929 cells and incubated with 10 µg/ml indicated TREM-Fc fusion proteins on ice for 30 min and then stained with anti-human IgG secondary and MitotrackerGreen. Staining was acquired and analyzed by flow cytometer.

It was sought to identify the ligand present on necroptotic cells that engages the TREM receptors to stimulate macrophages. When immuno-precipitation/mass-spectroscopy studies were performed using recombinant hTREML4-K86D-Fc on necroptotic cells, it was found that several dozen mitochondrial inner membrane proteins were detected. Therefore the ability of the TREM proteins to bind to different types of mitochondria was assessed by flow cytometry. As seen in FIG. 16, mTREML4 and hTREML4-K86D specifically bind to mitochondria derived from necroptotic, but not viable or apoptotic cells.

Figure 17:
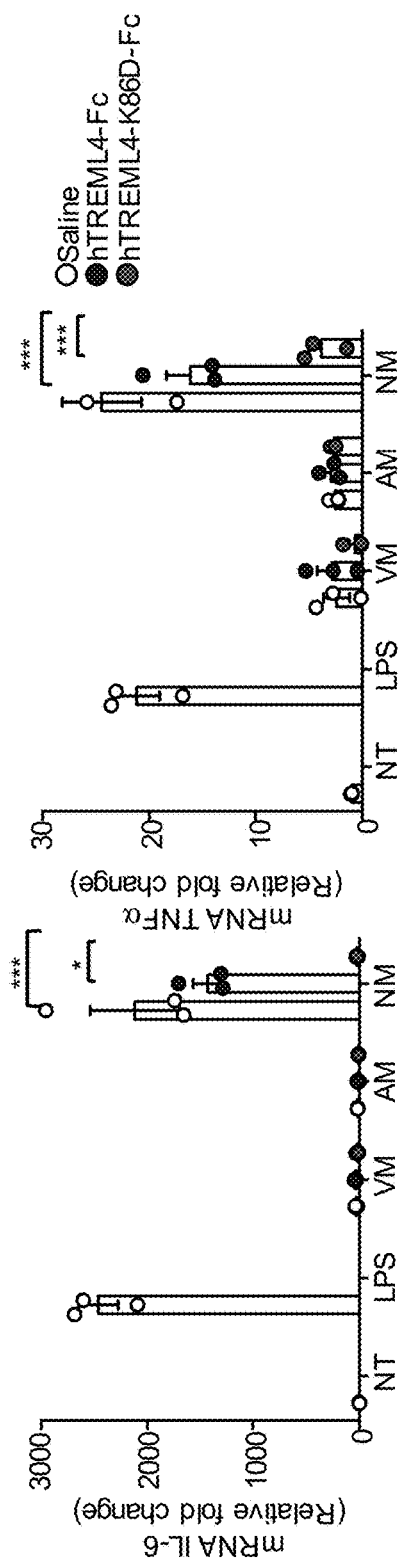
FIG. 17 depicts results of example experiments demonstrating that mitochondria isolated from necroptotic, but not apoptotic or viable cells stimulated inflammatory cytokine production (IL-6, TNF-alpha, and IL1-beta) in mouse BMDMs to a degree identical to LPS stimulation. Furthermore, the inflammatory effect of necroptotic mitochondria on BMDMs was greatly attenuated by administration of hTREML4-K86D-Fc but not WT hTREML4-Fc. L929 cells were incubated with 50 ng/ml anti-CD95 for 16 h to induce apoptosis and with 50 ng/nl TNF+10 µM zVAD for 6 h to induce necroptosis. Mitochondria were isolated from viable, apoptotic and necroptotic L929 cells and incubated with saline, 10 µg/mL hTREML4-Fc, or 10 µg/mL hTREML4-K86D-Fc on ice for 30 min and then washed three times with PBS. One million BMDMs were seeded per well in 24-well plates and stimulated with 100 ng/ml LPS or apoptotic/necroptotic mitochondria isolated from one million L929 cells. Six hours after stimulation, IL-6 and TNFα expression was measured by qPCR. Data show mean SEM combined from three independent experiments and analyzed by two-way ANOVA with multiple comparisons. *P<0.05, P<0.01, *P<0.001. The bars for each cell type are, from left to right: saline, hTREML4-Fc, and hTREML4-K86D-Fc. The Fc variant used was aglycosylated human IgG1 with the N297Q mutation.

To establish if isolated mitochondria from necroptotic cells mediate the inflammatory effect of necroptotic cell corpses as a Damage Associated Molecular Pattern (DAMP), they were applied directly to mouse macrophages. As seen in FIG. 17, mitochondria isolated from necroptotic cells stimulated inflammatory cytokine production (IL-6, IL1-beta, TNF-alpha) in BMDMs and this effect could be specifically blocked with hTREML4-K86D, but not WT hTREML4.

Figure 18:
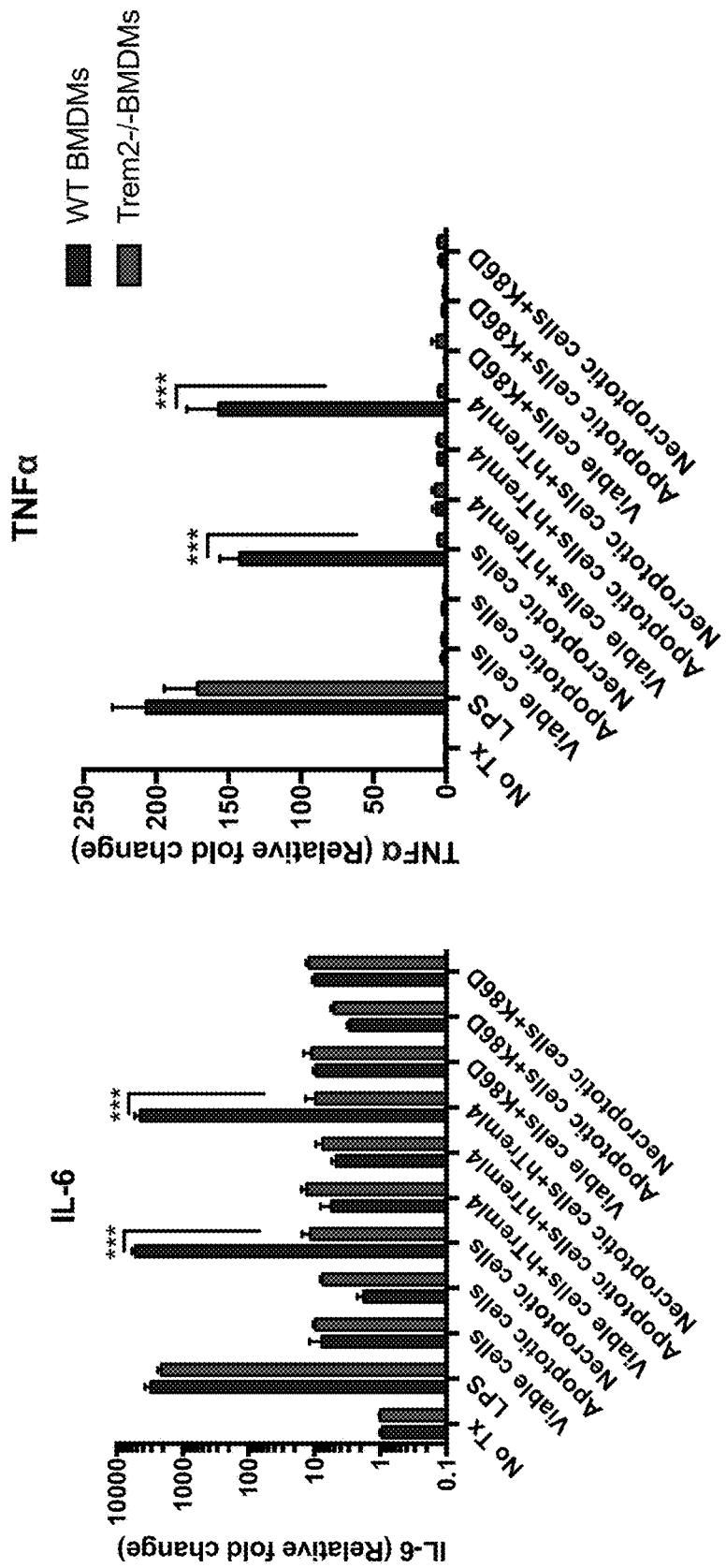
FIG. 18 depicts results of example experiments demonstrating that TREM2 is required for macrophages to respond to necroptotic corpses. BMDMs were prepared from WT or TREM2 deficient mice and incubated with viable, apoptotic, or necroptotic Jurkat cells. Only WT BMDMs produced inflammatory cytokines (IL-6 and TNF-alpha) in response to the application of necroptotic corpses; the effect was lost with knockout of TREM2 or by application of hTREML4-K86D-Fc. WT hTREML4-Fc was ineffective. Jurkat cells were induced with 2.5 µM Staurosporine for 16 h for apoptosis. FADD-/- Jurkat cells were induced with 20 ng/ml TNF for 16 h for necroptosis. Cells were washed and coated with hTREML4-Fc or hTREML4-K86D-Fc protein at 10 µg/ml on ice for 30 min and then washed three times with PBS. One million WT or TREM2-/- BMDMs in each well of 24-well plate were stimulated with 100 ng/ml LPS, 1 million apoptotic cells or 1 million necroptotic cells. Six hours after stimulation, mouse IL-6, and TNFα expression was measured by qPCR. Data show mean SEM combined from three independent experiments and analyzed by two-way ANOVA with multiple comparisons. *P<0.05, P<0.01, *P<0.001. WT BMDMs are the left bar for each group and Trem2-/- BMDMs are the right bar for each group. The Fc variant used was aglycosylated human IgG1 with the N297Q mutation.
Figures 19A, 19B, 19C:
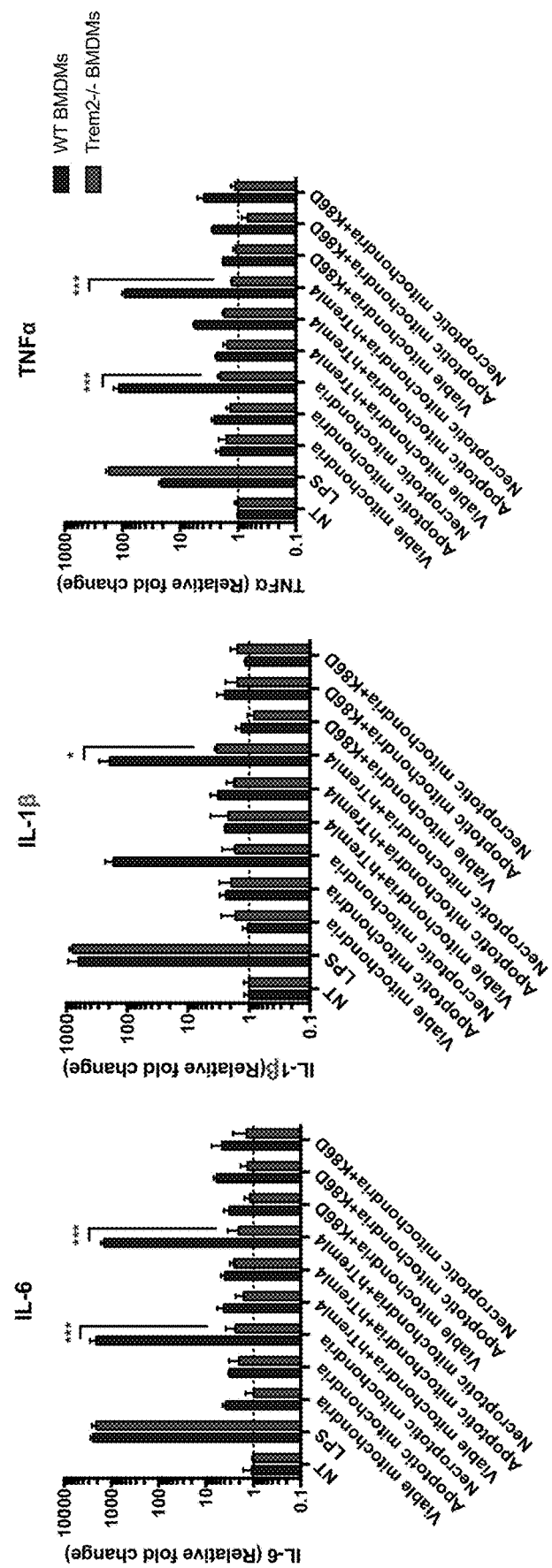
FIG. 19A through FIG. 19C, depicts results of example experiments demonstrating that TREM2 is required for macrophages to respond to necroptotic mitochondria. BMDMs were prepared from WT or TREM2 deficient mice and incubated with mitochondria derived from viable, apoptotic, or necroptotic L929 cells. Only WT BMDMs produced inflammatory cytokines (IL-6, IL1-beta, and TNF-alpha) in response to the application of necroptotic mitochondria; the effect was lost with knockout of TREM2 or by application of hTREML4-K86D-Fc. WT hTREML4-Fc was ineffective. L929 cells were induced with 50 ng/ml anti-CD95 for 16 h for apoptosis and with 50 ng/nl TNF+10 µM zVAD for 6 h for necroptosis. Mitochondria were isolated from viable, apoptotic and necroptotic L929 cells and incubated with hTREML4-Fc or hTREML4-K86D-Fc protein in 10 µg/ml on ice for 30 min and then washed three times with PBS. One million TREM2-/- or WT BMDMs in each well of 24-well plate were stimulated with 100 ng/ml LPS or apoptotic/necroptotic mitochondria from 1 million cells. Six hours after stimulation, IL-6 (FIG. 19A), IL-1β (FIG. 19B), and IL-1beta (FIG. 19C) expression was measured by qPCR. Data show mean SEM combined from three independent experiments and analyzed by two-way ANOVA with multiple comparisons. *P<0.05, P<0.01, *P<0.001. WT BMDMs are the left bar for each group and Trem2-/- BMDMs are the right bar for each group. The Fc variant used was aglycosylated human IgG1 with the N297Q mutation.
Figures 20A, 20B, 20C:
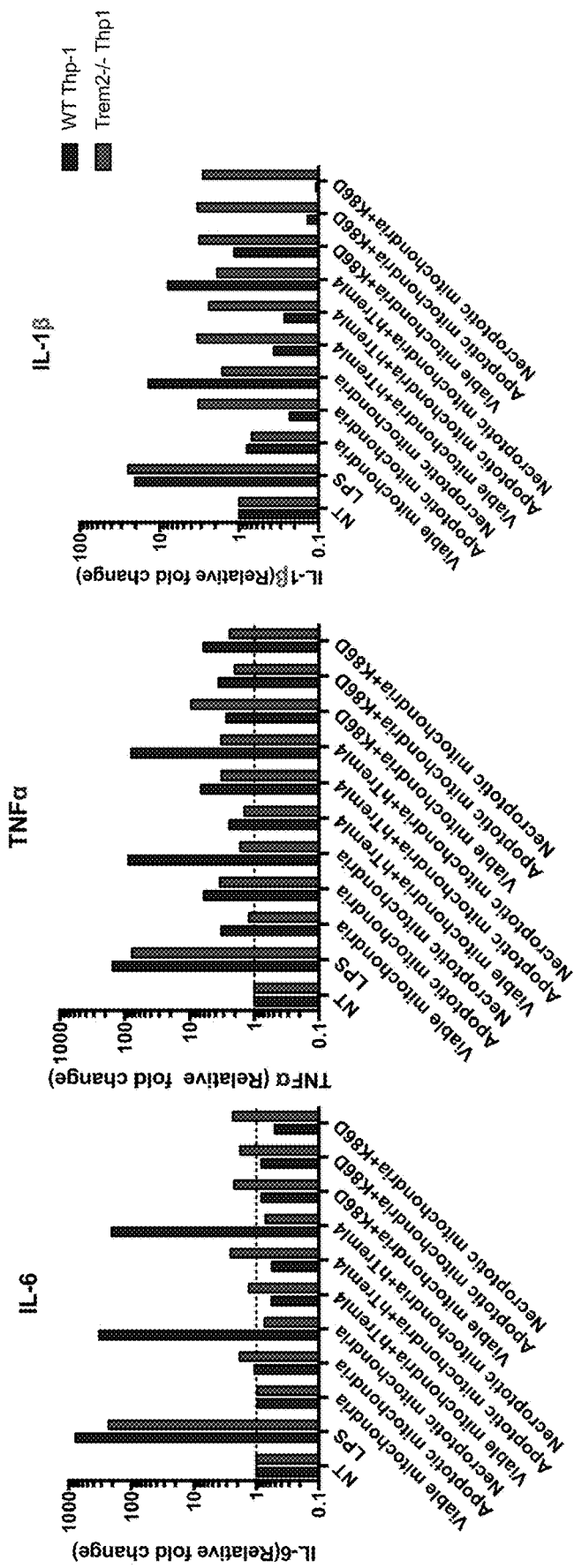
FIG. 20A through FIG. 20C, depicts results of example experiments demonstrating that TREM2 is required for human monocytes to respond to necroptotic mitochondria. TREM2 deficient THP1 cells were prepared by CRISPR/Cas9-mediated deletion and incubated with mitochondria derived from viable, apoptotic, or necroptotic L929 cells. Only WT THP-1 cells produced inflammatory cytokines (IL-6, IL1-beta, and TNF-alpha) in response to the application of necroptotic mitochondria; the effect was lost with knockout of TREM2 or by application of hTREML4-K86D-Fc. WT hTREML4-Fc was ineffective. L929 cells were induced with 50 ng/ml anti-CD95 for 16 h for apoptosis and with 50 ng/nl TNF+10 µM zVAD for 6 h for necroptosis. Mitochondria were isolated from viable, apoptotic and necroptotic L929 cells and incubated with hTREML4 or hTREML4-K86D protein in 10 µg/ml on ice for 30 min and then washed three times with PBS. One million WT Thp1 or TREM2-/- Thp1 cells in each well of 24-well plate were stimulated with 100 ng/ml LPS or apoptotic/necroptotic mitochondria from 1 million cells. Six hours after stimulation, IL-6 (FIG. 20A), TNFα (FIG. 20B) and IL-1β (FIG. 20C) expression was measured by qPCR. WT Thp-1 is the left bar for each group and Trem2-/- Thp1 is the right bar for each group. The Fc variant used was aglycosylated human IgG1 with the N297Q mutation.
Figure 21:
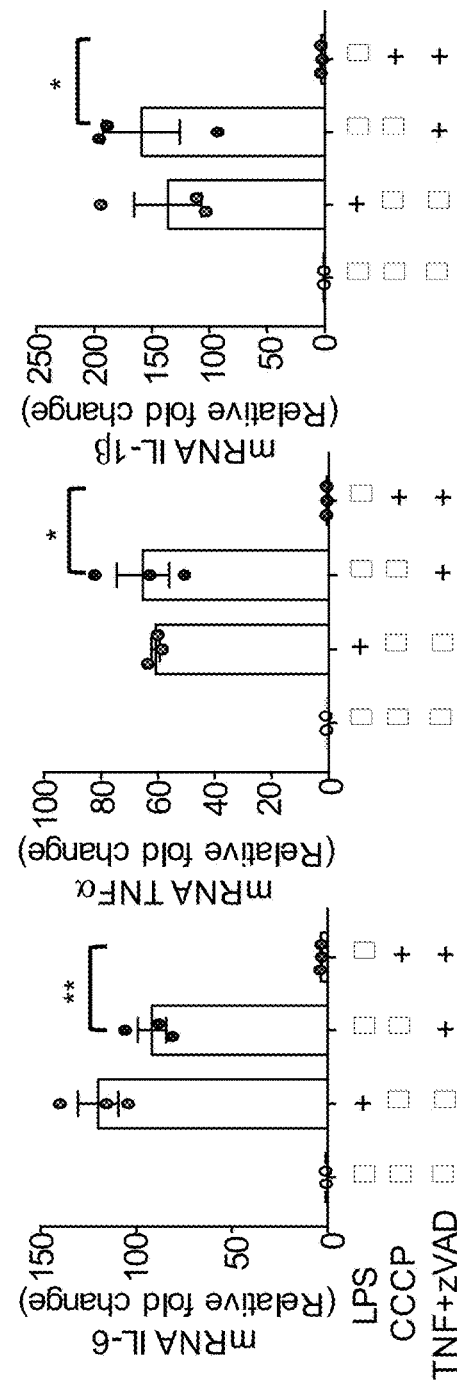
FIG. 21 depicts results of example experiments demonstrating that mitochondria within necroptotic corpses are required for activation of human monocytes. NIH-3T3 cells stably overexpressing Parkin were treated with 12.5 µM CCCP to induce mitophagy. Forty eight hours after CCCP treatment, cells were harvested and stained with mitotracker green to confirm the absence of mitochondria. Untreated and mitochondria-depleted 3T3 cells were subjected to 50 ng/ml TNF+10 µM zVAD for 6 h to induce necroptosis. One million Thp-1 cells in each well of 24-well plate were stimulated with 1 million necroptotic 3T3 cells or mitochondria-deleted 3T3 cells. Six hours after stimulation, expression of IL-6, TNF-alpha, and IL-1beta was measured by qPCR. Necroptotic NIH-3T3 cells that lacked mitochondria (+TNF-alpha+zVAD+CCCP) did not stimulate inflammatory cytokine production in THP-1 cells compared to necroptotic NIH-3T3 cells that contained mitochondria (+TNF-alpha+zVAD–CCCP). Data show mean SEM combined from three independent experiments and analyzed by paired t test. *P<0.05, P<0.01, *P<0.001

To establish which TREM protein mediates the macrophage response to necroptotic cell corpses and their associated mitochondrial DAMPs, studies were performed using BMDMs derived from TREM2 deficient mice and found that TREM2 deficient BMDMs did not respond to necroptotic corpses (FIG. 18) or purified mitochondria from necroptotic cells (FIG. 19), even though the LPS response remained intact. Similar results were observed in human THP-1 monocyte cells; when TREM2 was deleted with the CRISPR/cas9 system, those cells lost their ability to be stimulated by mitochondria from necroptotic cells (FIG. 20). To determine if mitochondria constitute the major DAMP in necroptotic cells, mitochondria-deficient NIH-3T3 cells were prepared by overexpression of parkin and treatment with carbonyl cyanide m-chlorophenyl hydrazone (CCCP). These mitochondria-deficient cells still underwent necroptotis upon treatment with TNF-alpha+zVAD, however their corpses did not stimulate cytokine secretion on BMDMs (FIG. 21).

Figure 22:
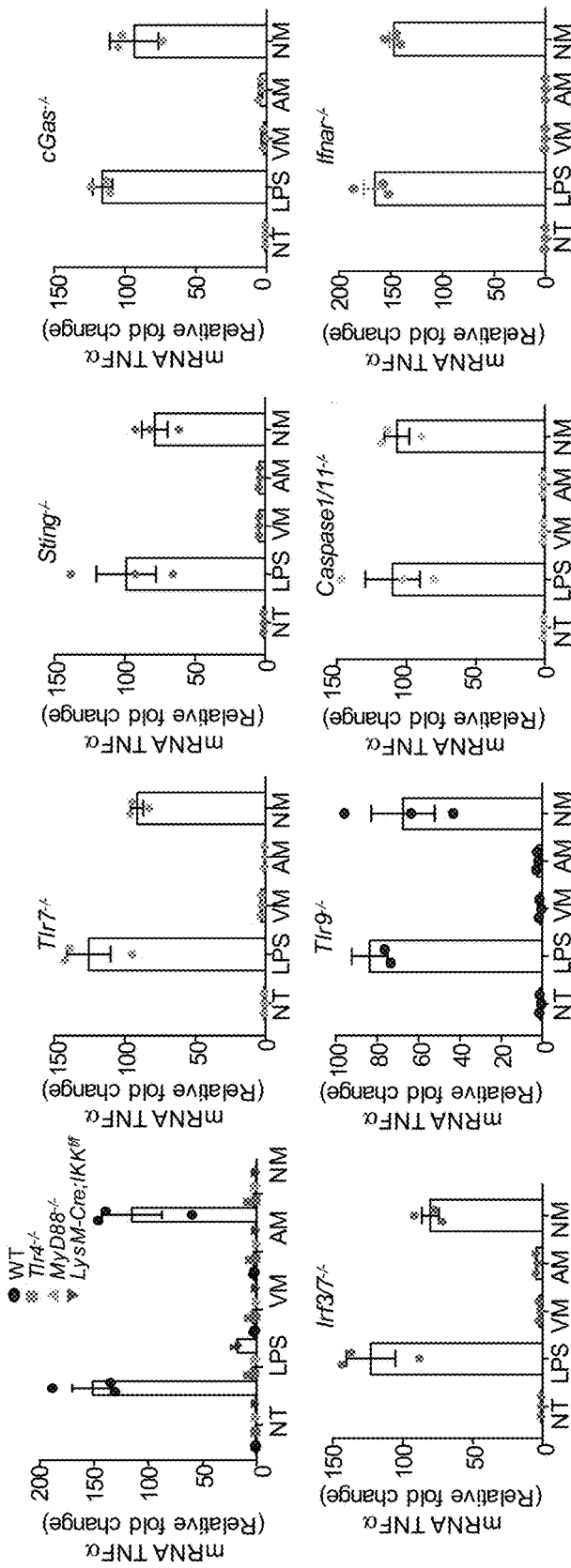
FIG. 22 depicts results of example experiments demonstrating TLR2/4, but not other pathogen-sensing, signaling is required for macrophages to sense necroptotic mitochondria. BMDMs were prepared from mice deficient in TLR4, MyD88, TLR7, TLR9, Sting, cGas, IRF3/7, Caspase 1/11, or IFNAR as well as mice in which NFkB signaling was ablated specifically in myeloid cells (LysM-Cre/Ikkb). BMDMs from all mice were plated in 24-well plate with 1 million cells/well. L929 cells were induced with 50 ng/ml anti-CD95 for 16 h for apoptosis and with 50 ng/nl TNF+10 $\mu$M zVAD for 6 h for necroptosis. Mitochondria were isolated from viable, apoptotic and necroptotic L929 cells and used to stimulate BMDMs of the indicated genotypes. Six hours after stimulation, TNF-alpha expression was measured by qPCR. BMDMs lacking TLR4, MyD88, or NFkB, did not produce inflammatory cytokines (TNF-alpha) in response to application of necroptotic mitochondria.
Figure 23:
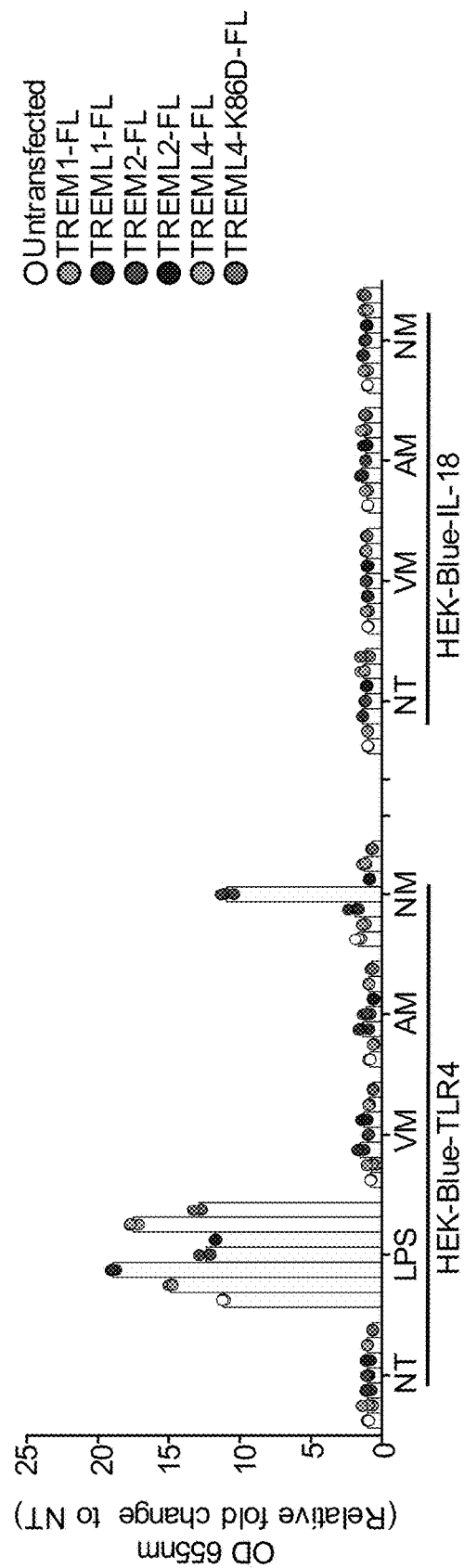
FIG. 23 depicts results of example experiments demonstrating that reconstitution of necroptotic mitochondria sensing requires TREM2 and TLR4 signaling. Hek blue-TLR4 and Hek blue-IL-18 293 cells in 6 well dishes were transfected with 2 $\mu$g of plasmid DNA encoding the indicated full-length TREM proteins using Lipofectamine 3000 according to the manufacturers' instructions. Cells were harvested in 36 h after transfection and plated in 96-well plate in $5\times10^4$ cells in each well. Cells were stimulated with LPS (100 ng/ml) or viable/apoptotic/necroptotic mitochondria from 1 million L929 cells. Six hours after stimulation, cell supernatants were diluted in QUANTI blue medium in 1/50 and incubated in 37° C. incubator for 1 h. SEAP activity was detected by reading the optical density at 655 nm and normalized to untreated groups. Only HEK cells containing TLR4 components and TREM2 produced signaling (measured by a colorimetric assay of the expressed SEAP reporter) in response to necroptotic mitochondria. Data show mean SEM combined from three independent experiments and analyzed by two-way ANOVA with multiple comparisons. *P<0.05, * *P<0.01, ***P<0.001. The bars for each cell type are, from left to right: untransfected, TREM1-FL, TREML I-FL, TREM2-FL, TREML2-FL, TREML4-FL, TREML4-K86D-FL.
Figure 24:
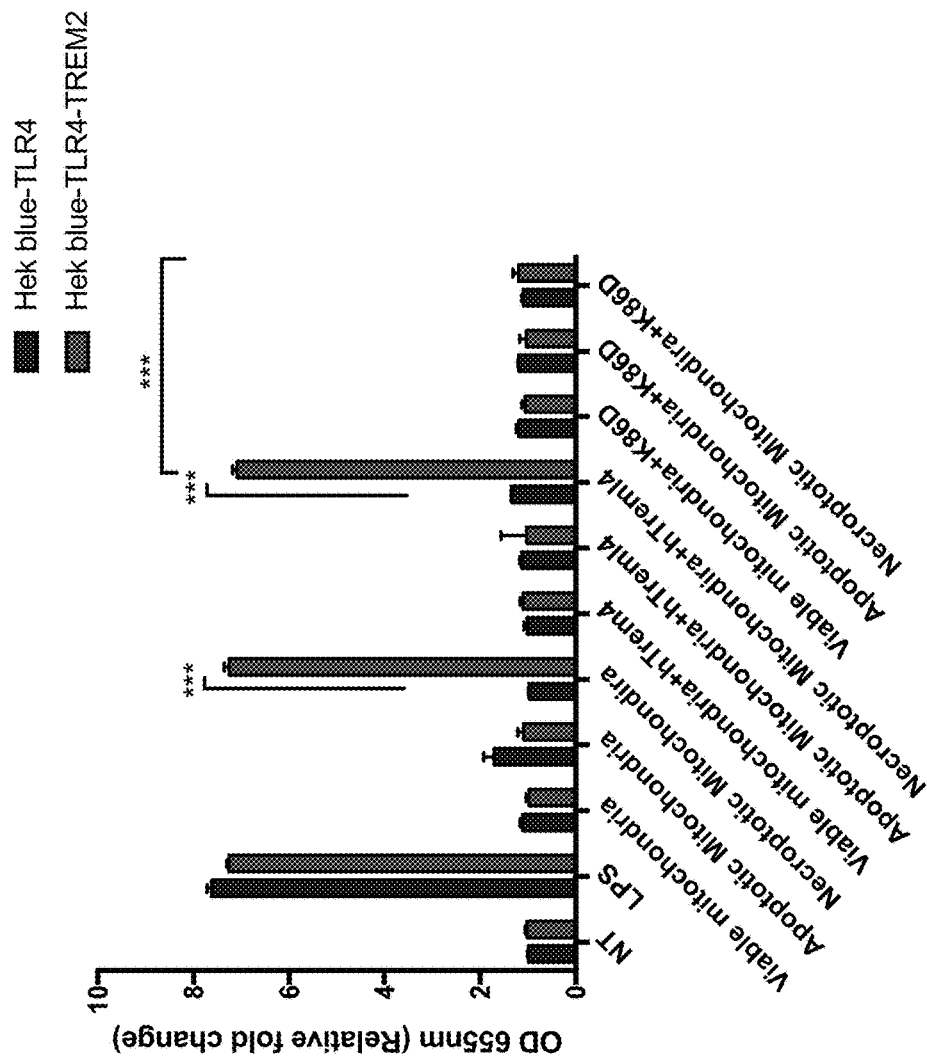
FIG. 24 depicts results of example experiments demonstrating that hTREML4-K86D-Fc inhibits TREM2/TLR4 mediated sensation of necroptotic mitochondria. HEK-Blue-TLR4 293 cells were transfected with full length TREM2 plasmid and then stimulated with 1 million viable, apoptotic and necroptotic mitochondria with or without 10 $\mu$g/ml human TREML4-Fc or TREML4-K86D-Fc. Six hours after stimulation, cell supernatants were diluted in QUANTI blue medium in 1/50 and incubated in 37° C. incubator for 1 h. SEAP activity was detected by reading the optical density at 655 nm and normalized to untreated groups. Only hTREML4-K86D-Fc but not WT hTREML4-Fc was capable of inhibiting the effect of necroptotic mitochondria to promote NFkB signaling. The Fc variant used was aglycosylated human IgG1 with the N297Q mutation. Data show mean SEM combined from three independent experiments and analyzed by two-way ANOVA with multiple comparisons. *P<0.05, P<0.01, *P<0.001. Hek blue-TLR4 is the left bar for each group and Hek blue-TLR4-TREM2 is the right bar for each group.

To establish if TREM2 detection of necroptotic corpses and their mitochondria requires other signaling components, co-culture studies were performed with mitochondria derived from necroptotic cells and BMDMs derived from TLR4, MyD88, myeloid-specific IKK (LysM-Cre:IKK$^{fl}$), TLR7, TLR9, Sting, cGas, Caspase 1/11, Irf3/7, and IFNAR knockout mice. As seen in FIG. 22, mice deficient in TLR4, MyD88, or IKK in myeloid cells were unable to respond to LPS or necroptotic mitochondria. These requirements were specific, since TLR7, TLR9, Sting, cGas, Caspase1/11, and Irf3/7 were dispensable for detection of necroptotic mitochondria. As seen in FIG. 23, however, TLR4 signaling by itself in the HEK-Blue-TLR4 reporter cell line (InVivoGen) which contains TLR4, CD14, and MD2, was not sufficient to respond to necroptotic mitochondria. However, transfection of full-length TREM2, but not TREM1, TREML1, TREML2, TREML4, or even TREML4-K86D enabled the cells to respond to necroptotic mitochondria, as evident from production of the SEAP reporter downstream of NFkB. Transfection of full-length TREM2 did not enable responses to necroptotic mitochondria in a related HEK-Blue-IL18 reporter cell line that contains IL-18Ra and IL-18Rb. As seen in FIG. 24, application of hTREML4-K86D-Fc but not WT hTREML4-Fc inhibited the ability of TREM2 transfected HEK-Blue-TLR4 cells to respond to necroptotic mitochondria. These results demonstrate that TREM2 and the TLR4 pathways cooperate to enable inflammatory responses driven by detection of necroptotic corpses and their mitochondria.

Figure 25:
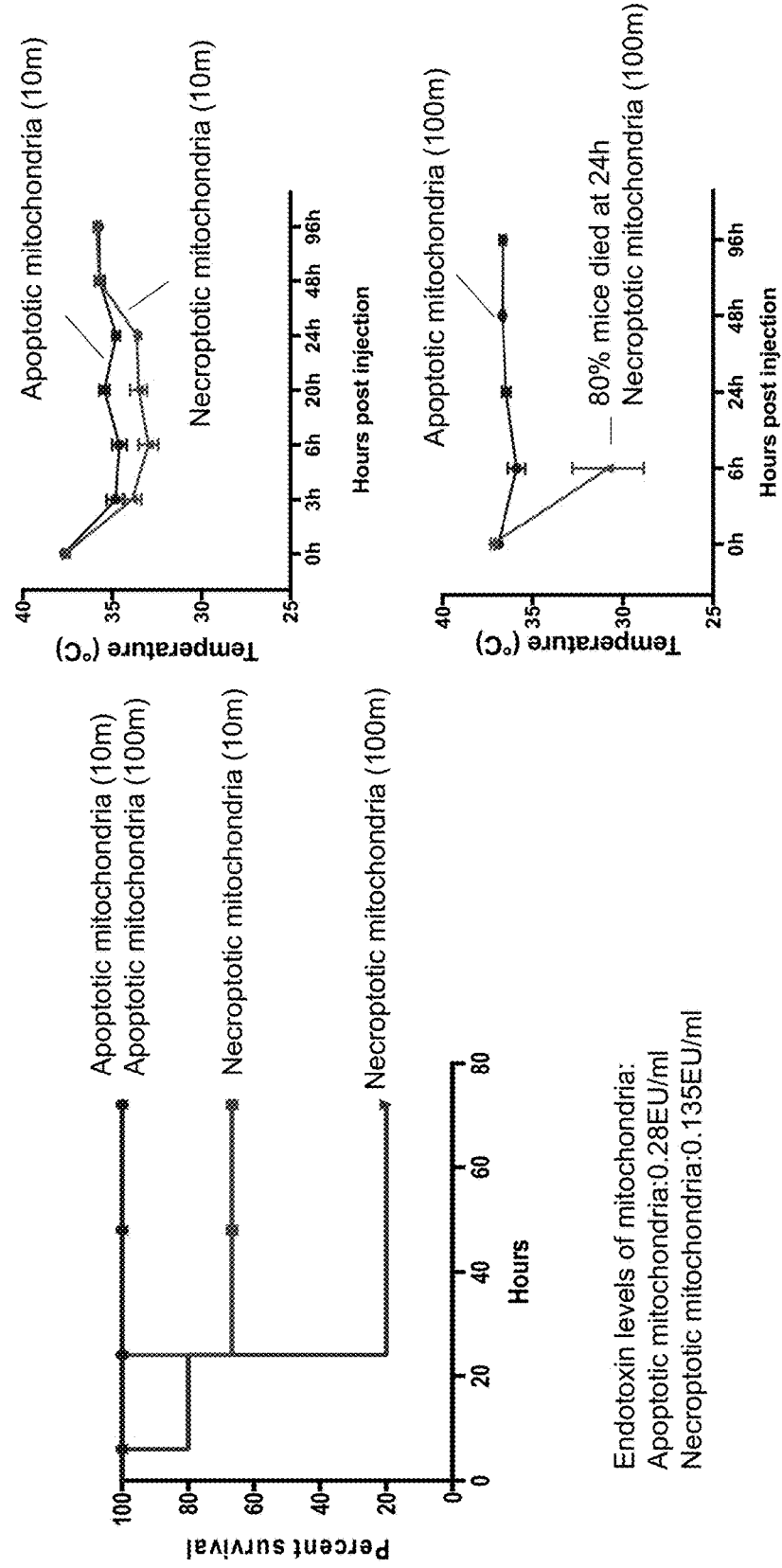
FIG. 25 depicts results of example experiments demonstrating that administration of mitochondria from necroptotic, but not apoptotic cells produces a rapid, fatal sepsis-like phenotype in mice. Mitochondria were then isolated from L929 cells after necroptosis or apoptosis. Mitochondria were washed three times with PBS and finally resuspended in 100 $\mu$l PBS. Endotoxin levels of mitochondria were detected by endotoxin cartridge strips. Each mouse was injected with 10 million or 100 million mitochondria in 100 $\mu$l PBS through retro orbital injection (n=5). Body temperature were measured and recorded. Survival was monitored for 3 days and analyzed with the Mantel-Haenzel Log Rank test. Administration of 10 or 100 million apoptotic mitochondria did not affect mouse survival or body temperature. However, injection of necroptotic mitochondria produced mortality in a dose-dependent fashion, which was accompanied by decreased body temperature.

To investigate the in vivo relevance of the TREM2-necroptotic mitochondria axis, it was sought to determine the effect of administration of different types of mitochondria to mice. As seen in FIG. 25, administration of 10 or 100 million mitochondria derived from apoptotic cells intravenously to mice had no effect on their survival or core body temperature. By contrast, administration of mitochondria derived from necroptotic cells produced dose-dependent toxicity within a rapid timeframe, killing 40-80% of the mice and causing profound drops in core body temperature.

Figure 26:
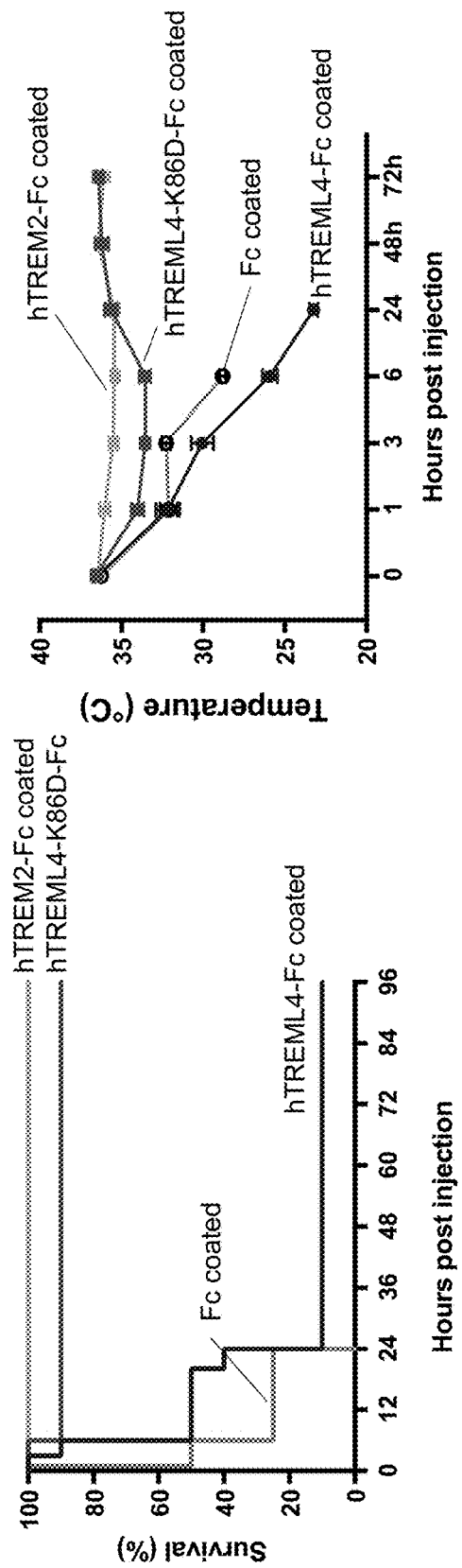
FIG. 26 depicts results of example experiments demonstrating that recombinant hTREM2-Fc and hTREML4-K86D-Fc, but not WT hTREML4-Fc prevent the sepsis-like syndrome produced by injection of necroptotic mitochondria. L929 cells were induced by 50 ng/ml TNFa+10 $\mu$M zVAD for 16 h for necroptosis. Mitochondria were isolated from necroptotic cells and counted in Accuri C6 and finally resuspended in 100 million per 100 $\mu$l PBS. Mitochondria were then coated with indicated TREM proteins or Fc at 1 $\mu$g/1 $\mu$l on ice for 30 mi. Each mouse was injected with 100 million mitochondria in 100 $\mu$l PBS through retro orbital injection (n=5). Body temperature were measured and recorded. Survival was monitored for 4 days and analyzed with the Mantel-Haenzel Log Rank test. Only coating with hTREM2-Fc and hTREML4-K86D-Fc reduced mortality and abrogated decreased body temperature. The Fc variant used was aglycosylated human IgG1 with the N297Q mutation.
Figure 27:
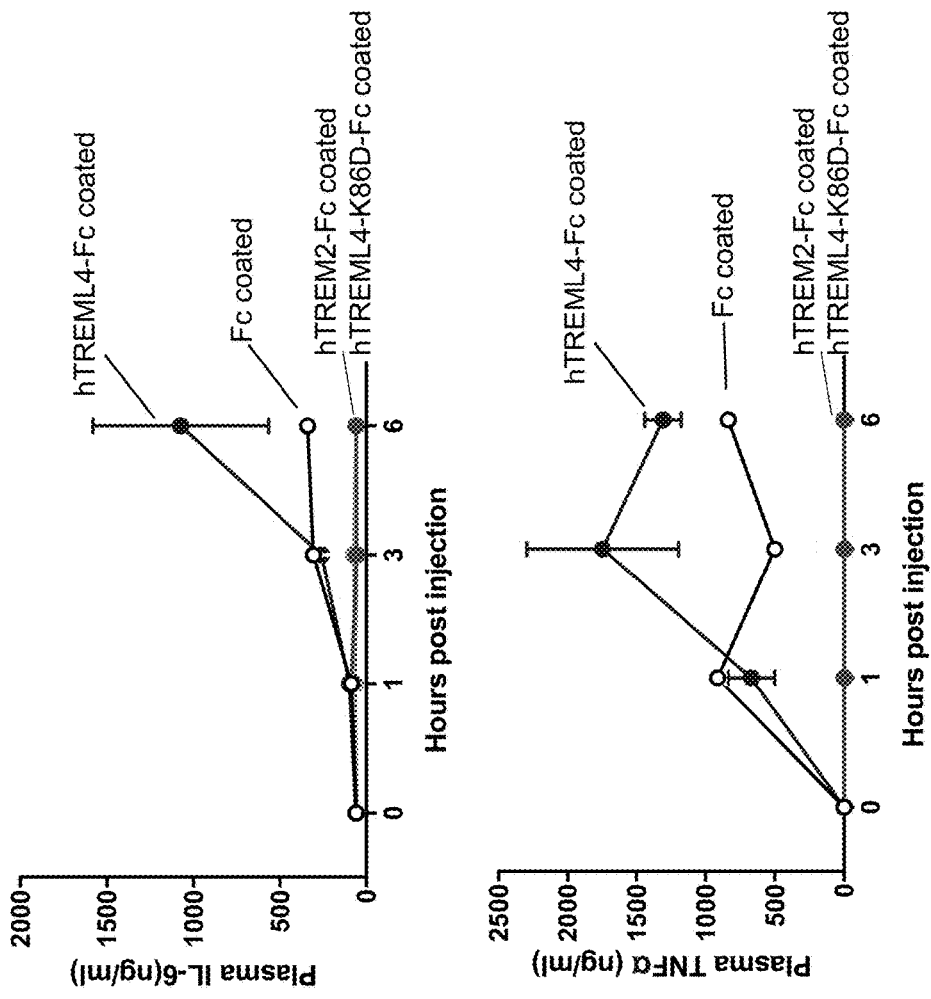
FIG. 27 depicts results of example experiments demonstrating that hTREM2-Fc and hTREML4-K86D-Fc, but not WT hTREML4-Fc inhibit systemic inflammatory cytokine accumulation in response to administration of mitochondria from necroptotic cells. Necroptotic mitochondria were isolated from L929 cells treated with TNF+zVAD for 16 h and then coated with indicated TREM-Fc proteins at 1 $\mu$g/$\mu$l on ice for 30 min. Each mouse was injected with 100 million indicated mitochondria in 100 $\mu$l PBS through retro orbital injection (n=5). Blood were collected before injection and at 1 h, 3 h and 6 h post injection. Plasma IL-6 and TNFa expression were measured by ELISA. Only coating with hTREM2-Fc and hTREML4-K86D-Fc prevented increases in IL-6 and TNF-alpha concentrations. The Fc variant used was aglycosylated human IgG1 with the N297Q mutation.

As seen in FIG. 26, this effect of necroptotic mitochondria could be prevented by pre-coating the mitochondria with hTREM2-Fc or hTREML4-K86D-Fc, but not WT hTREML4-Fc or isotype control hIgG1 Fc (N297Q). As seen in FIG. 27, administration of necroptotic mitochondria caused a rapid increase in systemic concentrations of inflammatory cytokines, including IL-6 and TNF-alpha. Pre-coating the mitochondria with hTREM2-Fc or hTREML4-K86D-Fc abrogated this effect. Taken together, these results from FIG. 17 to FIG. 27 genetically and pharmacologically establish mitochondria from necroptotic cells as the dominant DAMP from necroptotic corpses that is sensed by TREM2. They indicate that agents that inhibit the interaction between TREM2 and necroptotic corpses, particularly the mitochondria of necroptotic cells, is the key interface that must be antagonized for therapeutic utility.

Figure 28:
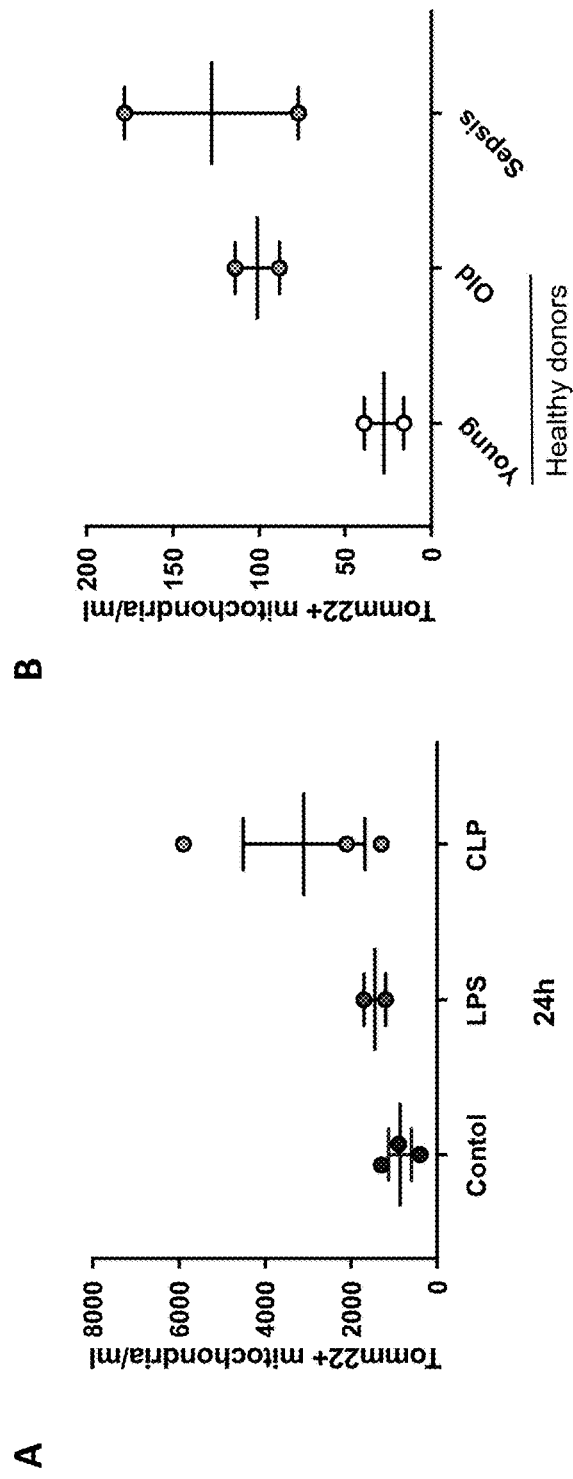
FIG. 28, comprising

Given the clear, dramatic etiological role of necroptotic cell corpses and their mitochondria in amplifying and sustaining inflammation in sepsis, it was examined whether circulating levels of mitochondria could be detected as a potential biomarker for informing the potential therapeutic indication(s) for TREM2 blockade. As seen in FIG. 28, circulating mitochondria could be detected in plasma in mice and human patients using flow cytometry with anti-mitochondria membrane protein antibodies, such as anti-Tomm22, as well as by using mitochondria-specific dyes such as Mitotracker Green. Mitochondria can be isolated by centrifugation of plasma/serum samples at 12,000 RCF for 15 minutes and stained with the indicated antibody or dye reagents. Mitochondria can also be isolated using magnetic separation approaches such as MACS (Miltenyi) or FACS (fluorescence activated cell sorting). Mice that were administered LPS or subjected to CLP had higher levels of circulating mitochondria in their plasma. Similarly, plasma samples from patients with sepsis also had higher levels of circulating mitochondria. These results indicate that measurement of systemic levels of mitochondria in blood has potential utility in predicting indications whereby TREM2 blockade could be therapeutically useful. It is envisaged that additional markers to distinguish between types of mitochondria (e.g., derived from viable, apoptotic, or necroptotic cells) could further enhance such a diagnostic biomarker. For instance, mitochondria could be further characterized by their hTREM2-Fc or hTREML4-K86D-Fc binding.

Figure 29:
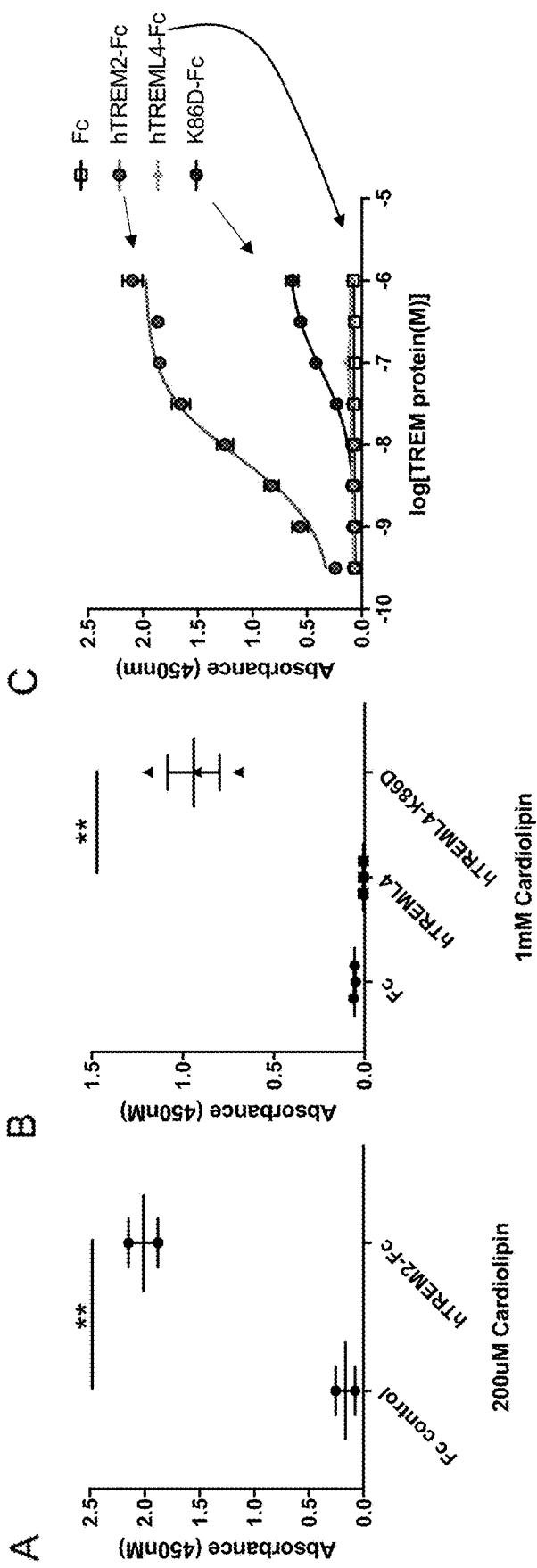
FIG. 29, comprising
Figure 30:
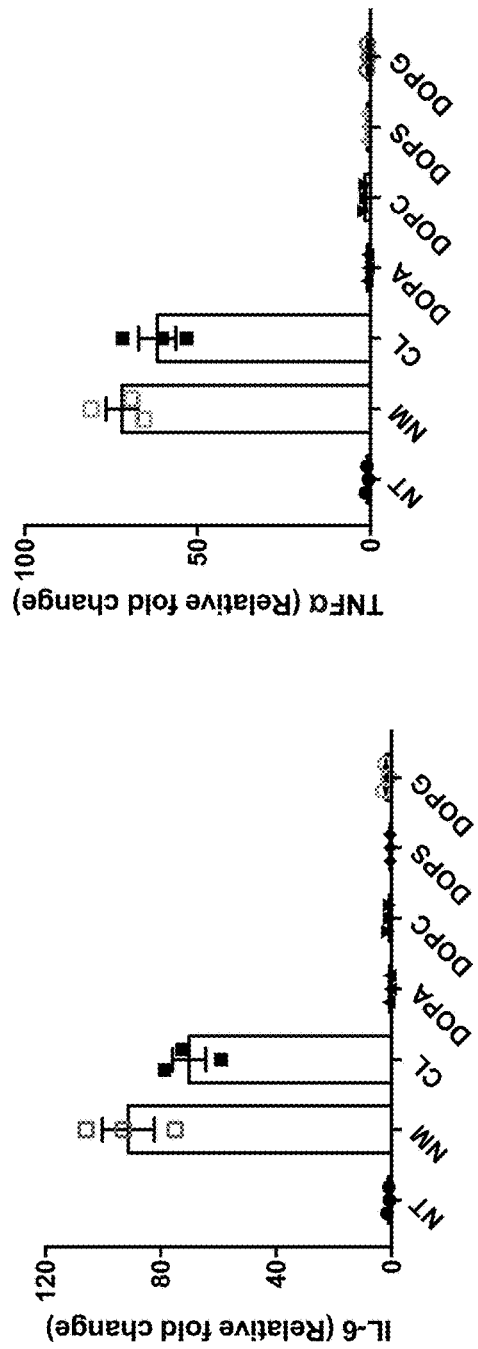
FIG. 30 depicts the results of example experiments showing that cardiolipin, but not other phospholipids, phenocopies the effect of necroptotic mitochondrial to activate of human Thp-1 cells. 100 uM of phosphatidic acid (DOPA), phosphatidylcholine (DOPC), phosphatidylserine (DOPS), phosphatidylglycerol (DOPG) and necroptotic mitochondria were used to stimulate 0.5 million Thp-1. Six hours after stimulation, IL-6 and TNF-alpha were measured by qPCR.
Figure 31:
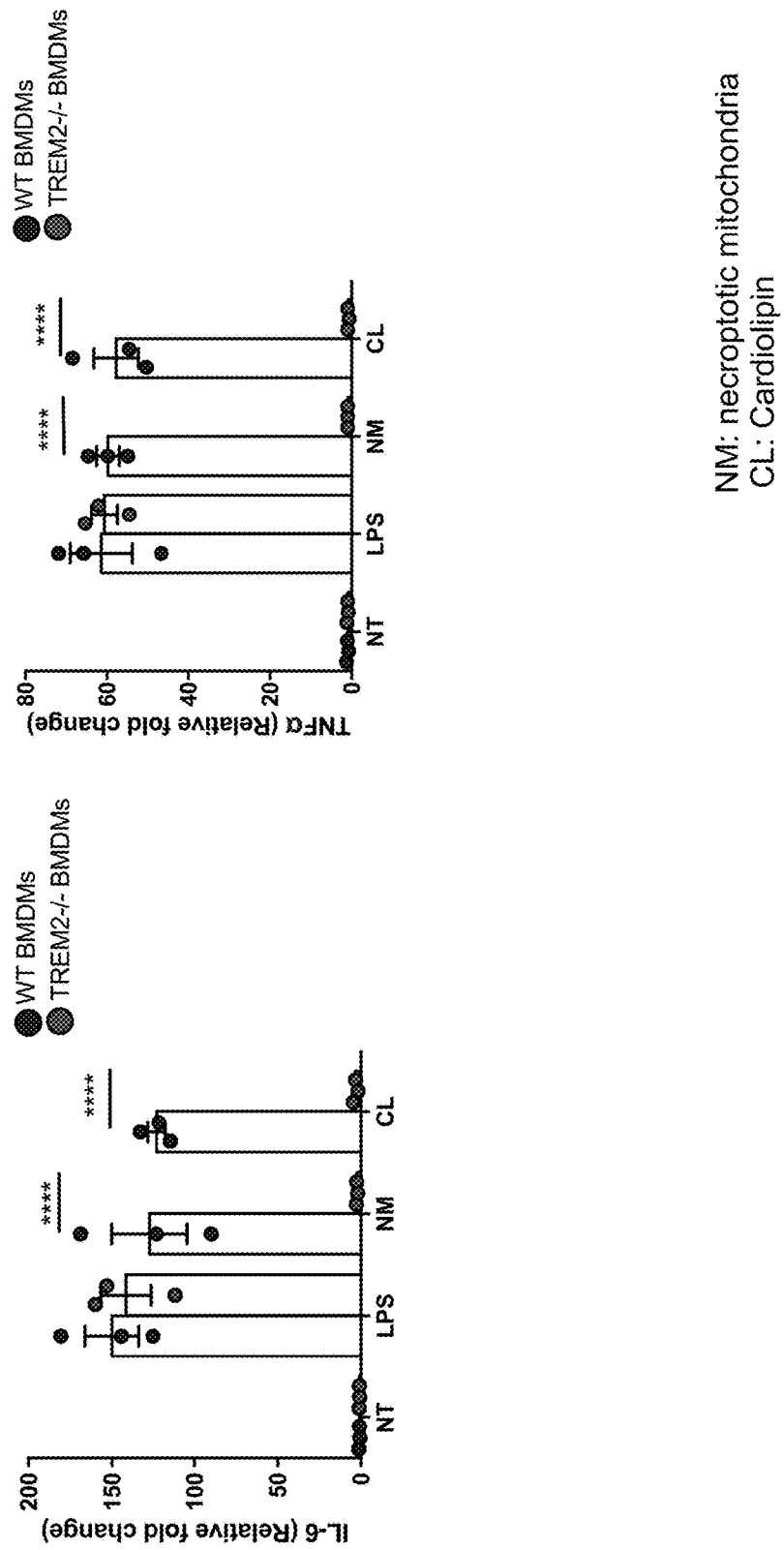
FIG. 31 depicts the results of example experiments demonstrating that CL directly stimulates inflammatory cytokine production in macrophages in a TREM2-dependent fashion. Murine BMDMs were stimulated with LPS, necroptotic mitochondria, or cardiolipin liposomes. Cardiolipin caused BMDMs to produce the inflammatory cytokines IL-6 and TNF-alpha to a degree commensurate with LPS or necroptotic mitochondria. This effect was lost in BMDMs derived from TREM2 deficient mice. *$P<0.05$, $P<0.01$, *$P<0.001$, ****$p<0.0001$. WT BMDMs are the left bar for each group and Trem2−/− BMDMs are the right bar for each group.
Figure 32:
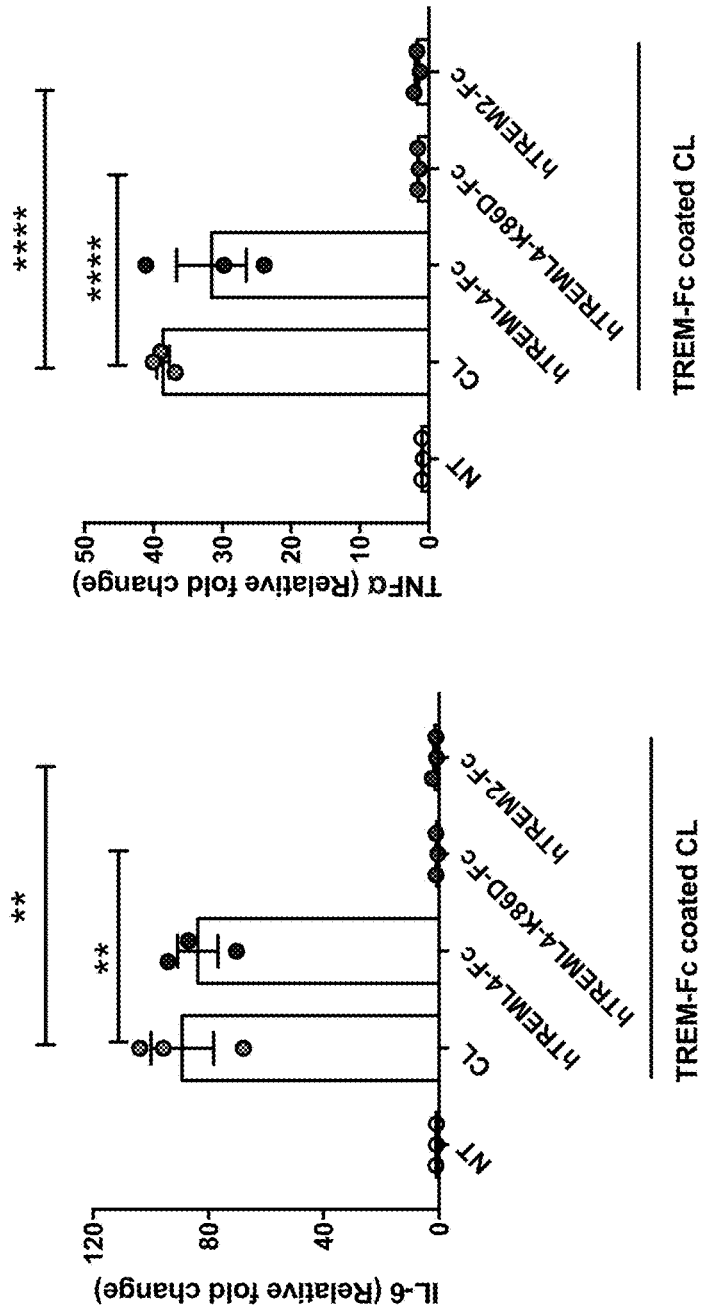
FIG. 32 depicts results from example experiments demonstrating that pre-coating of cardiolipin liposomes with hTREML4-K86D-Fc and hTREM2-Fc, but not wildtype hTREML4-Fc, abolished inflammatory activation of BMDM. Cardiolipin liposomes were incubated with 10 μg/ml hTREML4-Fc, hTREML4-K86D-Fc, or hTREM2-Fc protein on ice for 30 min. One million WT BMDMs in each well of 24-well plate were stimulated with cardiolipin liposomes that were pre-coated with the indicated Fc proteins. Six hours after stimulation, IL-6 and TNF-alpha were measured by qPCR. Data show mean SEM and analyzed by two-way ANOVA with multiple comparisons. *$P<0.05$, $P<0.01$, *$P<0.001$, ****$p<0.0001$. The Fc variant used was aglycosylated human IgG1 with the N297Q mutation.
Figure 33:
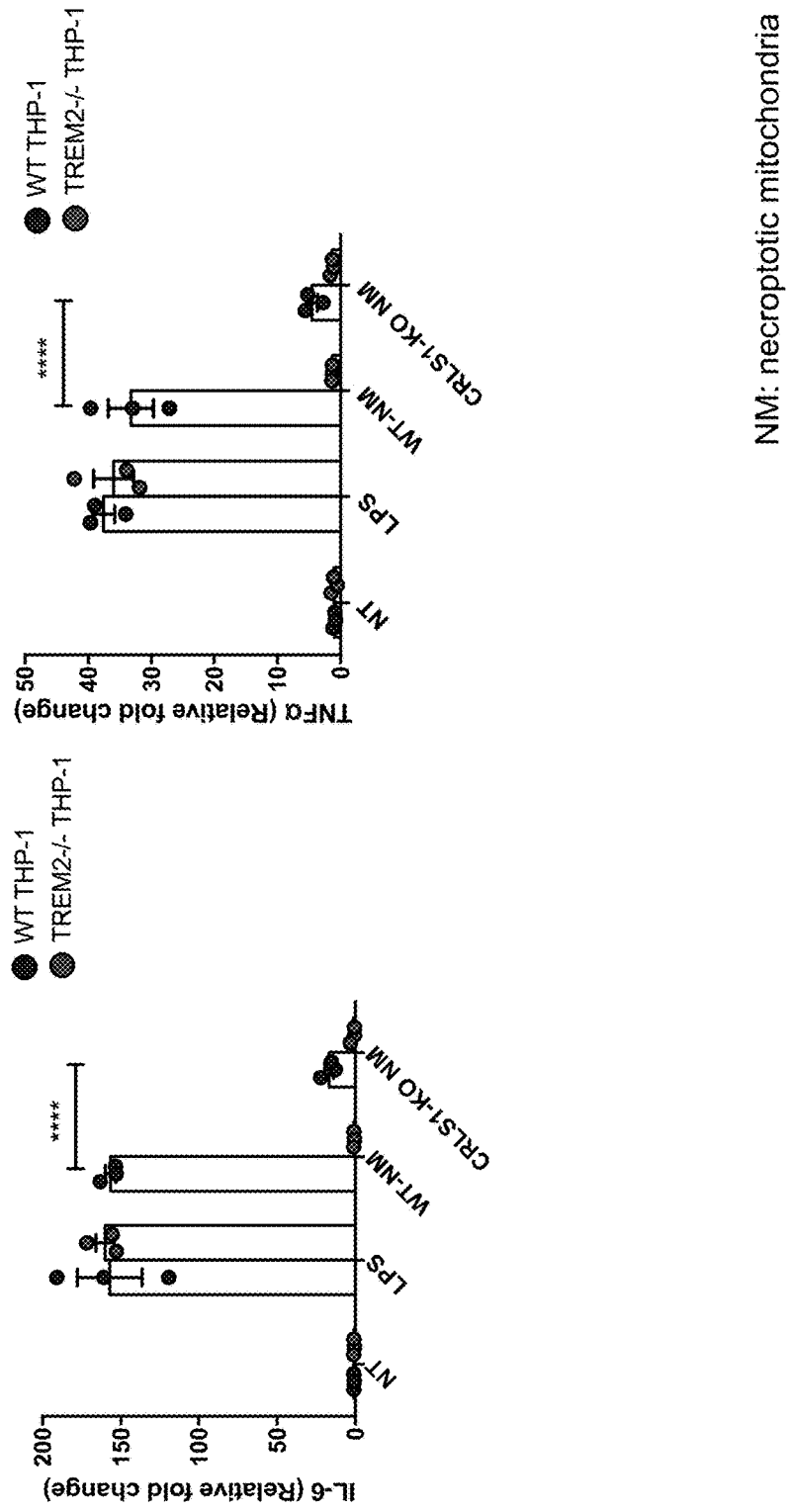
FIG. 33 depicts results from example experiments demonstrating that cardiolipin is required for necroptotic mitochondrial activation of Thp-1 cells in a TREM2-dependent fashion. The rate-limiting enzyme for cardiolipin synthesis (Crls1) was deleted using CRISPR/Cas9 technology in L929 cells and necroptosis was induced with TNF-alpha and zVAD and mitochondria from 1 million cells were used to stimulate TREM2-deficient and WT Thp-1 cells. Six hours after stimulation, IL-6 and TNF-alpha were measured by qPCR. Data show mean SEM and analyzed by two-way ANOVA with multiple comparisons. *$P<0.05$, $P<0.01$, *$P<0.001$, ****$p<0.0001$. WT BMDMs are the left bar for each group and Trem2−/− BMDMs are the right bar for each group.
Figure 34:
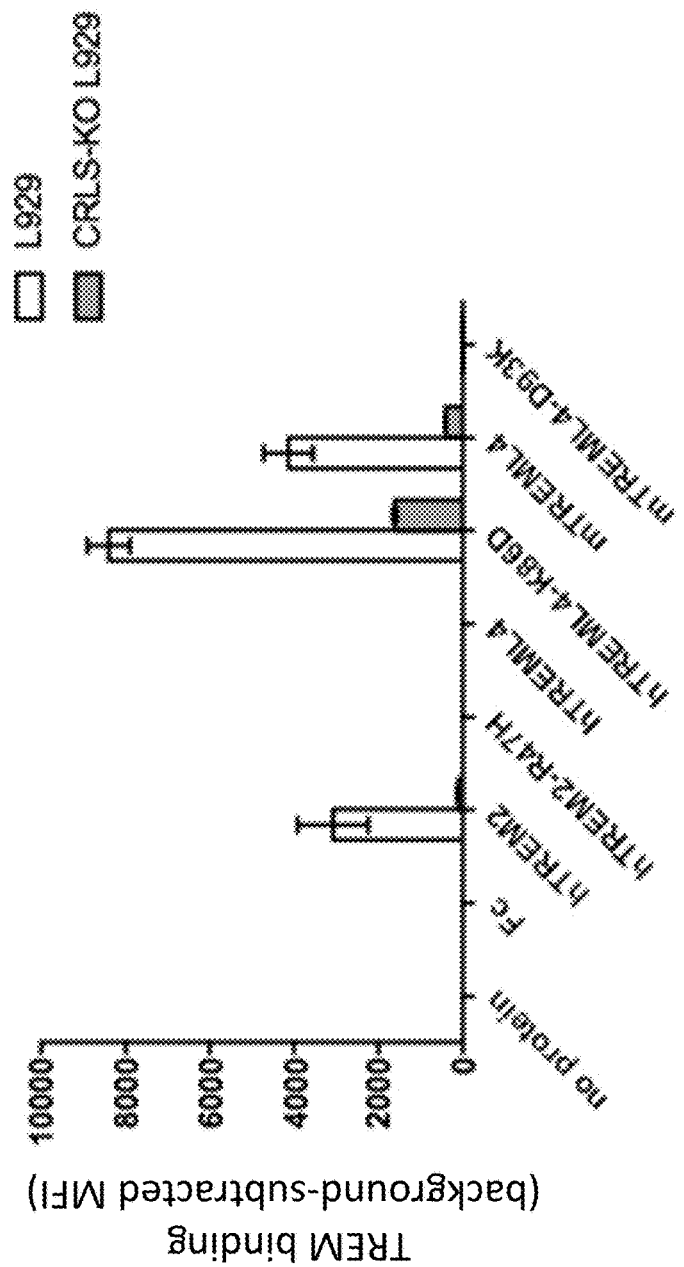
FIG. 34 depicts results from example experiments demonstrating the CL is a required feature of necroptotic mitochondria to bind TREM2. WT or Crls1-deficient L929 cells were induced to undergo necroptosis by application of TNF-alpha and zVAD and the resulting necroptotic mitochondria were isolated. hTREM2-Fc, hTREM2-R47H-Fc (an AD-associated mutation), hTREML4-Fc, hTREML4-K86D-Fc, mTREML4-Fc, or mTREML4-D93K were applied to the mitochondria and binding detected by flow cytometry. Only hTREM2, hTREML4-K86D, and mTREML4 fusion proteins bound the necroptotic mitochondria. Deletion of Crls1 completely abrogated binding of TREM2-Fc, and greatly attenuated binding of hTREML4-K86D-Fc and mTREML4-Fc. MFI mean fluorescence intensity.

Mitochondria from necroptotic cells in theory contain several potential DAMPs that could mediate their inflammatory effects. It was examined whether mitochondria-specific phospholipid cardiolipin (CL) could be a mitochondrial-DAMP ligand for TREM2. CL is normally contained within the mitochondrial inner membrane but can be externalized to the mitochondrial outer membrane during conditions of mitochondrial stress or cell death. CL liposomes were prepared and it was found that hTREM2 could directly bind them in an ELISA assay where the wells were pre-coated with the CL liposomes and then probed with recombinant hTREM2-Fc or Fc control protein (FIG. 29A-FIG. 29C). Having established that TREM2 directly binds CL, a BMDM stimulation assay was then performed and the pro-inflammatory activity of CL liposomes were compared to LPS or purified necroptotic mitochondria. As seen in FIG. 30, application of CL liposomes, but not other types of phospholipid liposomes (e.g., DOPA, DOPC, DOPS, DOPG) stimulated IL-6 and TNF-α production. Furthermore, as seen in FIG. 31, CL liposomes stimulated wild-type mouse BMDMs to produce IL-6 and TNF-alpha to a degree indistinguishable from LPS or necroptotic mitochondria. However, TREM2-deficient BMDMs did not respond to application of CL liposomes. Pharmacologic blockade of CL by application of hTREML4-K86D-Fc or hTREM2-Fc similarly inhibited inflammatory cytokine production in the same assay (FIG. 32). Further, experiments were conducted to test whether CL was required for the inflammatory character of necroptotic mitochondria. As seen in FIG. 33, deletion of the cardiolipin synthase 1 gene (CRLS1) which is required for the production of CL rendered necroptotic mitochondria unable to stimulate THP-1 cells. As seen in FIG. 34, necroptotic mitochondria derived from CRLS1-deficient cells also did not bind TREM2, indicating it is the specific molecular ligand on these mitochondria that engaged with TREM2. These results thus indicate that CL is a mitochondrial-derived damage-associated molecular pattern that mediates its inflammatory effects through TREM2.

It has been shown that TREM2 and TREML4 are attractive therapeutic targets for the treatment of sepsis and other disease conditions related to inflammation. Importantly, the ectodomains of TREML4-Fc and TREM2-Fc are pharmacologically active as therapeutic agents in a mouse model of sepsis. It is also shown that TREML4-Fc and TREM2-Fc can be given therapeutically in mouse models, at time points well past what is thought to be the critical window of intervention, making it a potentially relevant treatment modality in human disease. It is also shown that specific novel mutations must be made in the human TREML4 ectodomain to enable its therapeutic utility as a TREM2/TREML4 antagonist. It is also shown that the recombinant TREM2/TREML4 protein must not have Fc effector functions to be effective, a crucial non-obvious result. Finally, it is shown that the crucial, non-obvious feature of TREM2 that must be targeted for therapeutic efficacy is the interaction between TREM2 and necroptotic mitochondria, specifically the mitochondrial phospholipid cardiolipin.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for reducing inflammation in a subject, wherein the composition comprises a protein comprising an ectodomain of Triggering Receptor Expressed on Myeloid cells (TREM)-like 4 (TREML4),
   a) wherein the ectodomain of TREML4 comprises the amino acid sequence selected from the group consisting of: SEQ ID NO: 14 and an amino acid sequence that is at least 95% homologous to SEQ ID NO: 14, or
   b) wherein the ectodomain of TREML4 comprises one or more mutations that confer binding of the ectodomain to a necrotic cell or necroptotic cell, wherein the one or more mutations are at one or more residues selected from the group consisting of T35, L65, L66, S69, K71, K78, K86, T95, G156, and H160, relative to full-length SEQ ID NO: 44, and wherein the ectodomain of TREML4 comprises the amino acid sequence selected from the group consisting of: SEQ ID NO: 2, an amino acid sequence that is at least 95% homologous to SEQ ID NO: 2, SEQ ID NO: 3, an amino acid sequence that is at least 95% homologous to SEQ ID NO: 3, SEQ ID NO: 4, an amino acid sequence that is at least 95% homologous to SEQ ID NO: 4, SEQ ID NO: 5, an amino acid sequence that is at least 95% homologous to SEQ ID NO: 5, SEQ ID NO: 6, an amino acid sequence that is at least 95% homologous to SEQ ID NO: 6, SEQ ID NO: 7, an amino acid sequence that is at least 95% homologous to SEQ ID NO: 7, SEQ ID NO: 8, an amino acid sequence that is at least 95% homologous to SEQ ID NO: 8, SEQ ID NO: 9, an amino acid sequence that is at least 95% homologous to SEQ ID NO: 9, SEQ ID NO: 10, an amino acid sequence that is at least 95% homologous to SEQ ID NO: 10, SEQ ID NO: 11, an amino acid sequence that is at least 95% homologous to SEQ ID NO: 11, SEQ ID NO: 12, an amino acid sequence that is at least 95% homologous to SEQ ID NO: 12, SEQ ID NO: 13, and an amino acid sequence that is at least 95% homologous to SEQ ID NO: 13.

2. The composition of claim 1, wherein the ectodomain of TREML4 comprises the amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

3. The composition of claim 1, wherein the protein comprises a first domain and a second domain;
wherein the first domain comprises the ectodomain of TREML4; and
wherein the second domain comprises at least one region of an immunoglobulin.

4. The composition of claim 3, wherein the second domain comprises an Fc domain of an immunoglobulin.

5. The composition of claim 3, wherein the second domain comprises the Fc domain of human IgG1.

6. The composition of claim 3, wherein the second domain comprises an Fc domain of an immunoglobulin that comprises one or more mutations to remove Fc effector function through Fc receptors or complement.

7. The composition of claim 6, wherein the second domain comprises an Fc domain of human IgG1 comprising a mutation at residue N297, relative to wildtype human IgG1, rendering the Fc domain aglycosylated.

8. The composition of claim 7, wherein the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22.

9. The composition of claim 1, wherein the protein comprises an amino acid sequence selected from the group consisting of: SEQ ID NO: 26, an amino acid sequence that is at least 90% homologous to SEQ ID NO: 26, SEQ ID NO: 27, an amino acid sequence that is at least 90% homologous to SEQ ID NO: 27, SEQ ID NO: 28, an amino acid sequence that is at least 90% homologous to SEQ ID NO: 28, SEQ ID NO: 29, an amino acid sequence that is at least 90% homologous to SEQ ID NO: 29, SEQ ID NO: 30, an amino acid sequence that is at least 90% homologous to SEQ ID NO: 30, SEQ ID NO: 31, an amino acid sequence that is at least 90% homologous to SEQ ID NO: 31, SEQ ID NO: 32, an amino acid sequence that is at least 90% homologous to SEQ ID NO: 32, SEQ ID NO: 33, an amino acid sequence that is at least 90% homologous to SEQ ID NO: 33, SEQ ID NO: 34, an amino acid sequence that is at least 90% homologous to SEQ ID NO: 34, SEQ ID NO: 35, an amino acid sequence that is at least 90% homologous to SEQ ID NO: 35, SEQ ID NO: 36, an amino acid sequence that is at least 90% homologous to SEQ ID NO: 36, SEQ ID NO: 37, an amino acid sequence that is at least 90% homologous to SEQ ID NO: 37, SEQ ID NO: 38, an amino acid sequence that is at least 90% homologous to SEQ ID NO: 38, SEQ ID NO: 39, and an amino acid sequence that is at least 90% homologous to SEQ ID NO: 39.

10. An isolated nucleic acid molecule comprising a nucleotide sequence encoding the composition of claim 1.

11. A method of reducing inflammation in a subject, comprising administering to the subject the composition of claim 1.

12. The method of claim 11, wherein the protein comprises a first domain and a second domain;
wherein the first domain comprises the ectodomain of TREML4; and
wherein the second domain comprises at least one region of an immunoglobulin.

13. The method of claim 11, wherein the ectodomain of TREML4 comprises the amino acid sequence selected from the group consisting of: SEQ ID NO: 2, an amino acid sequence that is at least 95% homologous to SEQ ID NO: 2, SEQ ID NO: 3, an amino acid sequence that is at least 95% homologous to SEQ ID NO: 3, SEQ ID NO: 4, an amino acid sequence that is at least 95% homologous to SEQ ID NO: 4, SEQ ID NO: 5, an amino acid sequence that is at least 95% homologous to SEQ ID NO: 5, SEQ ID NO: 6, an amino acid sequence that is at least 95% homologous to SEQ ID NO: 6, SEQ ID NO: 7, an amino acid sequence that is at least 95% homologous to SEQ ID NO: 7, SEQ ID NO: 8, an amino acid sequence that is at least 95% homologous to SEQ ID NO: 8, SEQ ID NO: 9, an amino acid sequence that is at least 95% homologous to SEQ ID NO: 9, SEQ ID NO: 10, an amino acid sequence that is at least 95% homologous to SEQ ID NO: 10, SEQ ID NO: 11, an amino acid sequence that is at least 95% homologous to SEQ ID NO: 11, SEQ ID NO: 12, an amino acid sequence that is at least 95% homologous to SEQ ID NO: 12, SEQ ID NO: 13, and an amino acid sequence that is at least 95% homologous to SEQ ID NO: 13.

14. The method of claim 12, wherein the second domain comprises an Fc domain of an immunoglobulin.

15. The method of claim 12, wherein the second domain comprises the Fc domain of human IgG1.

16. The method of claim 12, wherein the second domain comprises an Fc domain of an immunoglobulin that comprises one or more mutations to remove Fc effector function through Fc receptors or complement.

17. The method of claim 16, wherein the second domain comprises an Fc domain of human IgG1 comprising a mutation at residue N297, relative to wildtype human IgG1, rendering the Fc domain aglycosylated.

18. The method of claim 17, wherein the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22.

19. The method of claim 11, wherein the protein comprises an amino acid sequence selected from the group consisting of SEQ ID NO: 26, an amino acid sequence that is at least 90% homologous to SEQ ID NO: 26, SEQ ID NO: 27, an amino acid sequence that is at least 90% homologous to SEQ ID NO: 27, SEQ ID NO: 28, an amino acid sequence that is at least 90% homologous to SEQ ID NO: 28, SEQ ID NO: 29, an amino acid sequence that is at least 90% homologous to SEQ ID NO: 29, SEQ ID NO: 30, an amino acid sequence that is at least 90% homologous to SEQ ID NO: 30, SEQ ID NO: 31, an amino acid sequence that is at least 90% homologous to SEQ ID NO: 31, SEQ ID NO: 32, an amino acid sequence that is at least 90% homologous to SEQ ID NO: 32, SEQ ID NO: 33, an amino acid sequence that is at least 90% homologous to SEQ ID NO: 33, SEQ ID NO: 34, an amino acid sequence that is at least 90% homologous to SEQ ID NO: 34, SEQ ID NO: 35, an amino acid sequence that is at least 90% homologous to SEQ ID NO: 35, SEQ ID NO: 36, an amino acid sequence that is at least 90% homologous to SEQ ID NO: 36, SEQ ID NO: 37, an amino acid sequence that is at least 90% homologous to SEQ ID NO: 37, SEQ ID NO: 38, an amino acid sequence that is at least 90% homologous to SEQ ID NO: 38, SEQ ID NO: 39, and an amino acid sequence that is at least 90% homologous to SEQ ID NO: 39.

20. The method of claim 11, wherein the subject has an inflammatory, autoinflammatory, or autoimmune disease or disorder.

21. The method of claim 11, wherein the subject is at risk for developing an inflammatory, autoinflammatory, or autoimmune disease or disorder.

22. A composition for detecting a necroptotic cell, wherein the composition comprises a protein comprising an ectodomain of TREML4, or a variant thereof, and a detectable label,
   a) wherein the ectodomain of TREML4 comprises the amino acid sequence selected from the group consisting of: SEQ ID NO: 14 and an amino acid sequence that is at least 95% homologous to SEQ ID NO: 14, or
   b) wherein the ectodomain of TREML4 comprises one or more mutations that confer binding of the ectodomain to a necrotic cell or necroptotic cell, wherein the one or more mutations are at one or more residues selected from the group consisting of T35, L65, L66, S69, K71, K78, K86, T95, G156, and H160, relative to full-length SEQ ID NO: 44, and wherein the ectodomain of TREML4 comprises the amino acid sequence selected from the group consisting of: SEQ ID NO: 2, an amino acid sequence that is at least 95% homologous to SEQ ID NO: 2, SEQ ID NO: 3, an amino acid sequence that is at least 95% homologous to SEQ ID NO: 3, SEQ ID NO: 4, an amino acid sequence that is at least 95% homologous to SEQ ID NO: 4, SEQ ID NO: 5, an amino acid sequence that is at least 95% homologous to SEQ ID NO: 5, SEQ ID NO: 6, an amino acid sequence that is at least 95% homologous to SEQ ID NO: 6, SEQ ID NO: 7, an amino acid sequence that is at least 95% homologous to SEQ ID NO: 7, SEQ ID NO: 8, an amino acid sequence that is at least 95% homologous to SEQ ID NO: 8, SEQ ID NO: 9, an amino acid sequence that is at least 95% homologous to SEQ ID NO: 9, SEQ ID NO: 10, an amino acid sequence that is at least 95% homologous to SEQ ID NO: 10, SEQ ID NO: 11, an amino acid sequence that is at least 95% homologous to SEQ ID NO: 11, SEQ ID NO: 12, an amino acid sequence that is at least 95% homologous to SEQ ID NO: 12, SEQ ID NO: 13, and an amino acid sequence that is at least 95% homologous to SEQ ID NO: 13.

23. The composition of claim 22, wherein the ectodomain of TREML4 comprises the amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

24. The composition of claim 22, wherein the protein comprises a first domain and a second domain;
   wherein the first domain comprises the ectodomain of TREML4; and
   wherein the second domain comprises at least one region of an immunoglobulin.

25. The composition of claim 24, wherein the second domain comprises an Fc domain of an immunoglobulin.

26. The composition of claim 24, wherein the second domain comprises the Fc domain of human IgG1.

27. The composition of claim 24, wherein the second domain comprises an Fc domain of an immunoglobulin that comprises one or more mutations to remove Fc effector function through Fc receptors or complement.

28. The composition of claim 27, wherein the second domain comprises an Fc domain of human IgG1 comprising a mutation at residue N297, relative to wildtype human IgG1, rendering the Fc domain aglycosylated.

29. The composition of claim 28, wherein the second domain comprises an amino acid sequence selected from the group consisting of SEQ ID NO: 20, an amino acid sequence that is at least 90% homologous to SEQ ID NO: 20, SEQ ID NO: 21, an amino acid sequence that is at least 90% homologous to SEQ ID NO: 21, SEQ ID NO: 22, and an amino acid sequence that is at least 90% homologous to SEQ ID NO: 22.

30. The composition of claim 22, wherein the protein comprises an amino acid sequence selected from the group consisting of: SEQ ID NO: 26, an amino acid sequence that is at least 90% homologous to SEQ ID NO: 26, SEQ ID NO: 27, an amino acid sequence that is at least 90% homologous to SEQ ID NO: 27, SEQ ID NO: 28, an amino acid sequence that is at least 90% homologous to SEQ ID NO: 28, SEQ ID NO: 29, an amino acid sequence that is at least 90% homologous to SEQ ID NO: 29, SEQ ID NO: 30, an amino acid sequence that is at least 90% homologous to SEQ ID NO: 30, SEQ ID NO: 31, an amino acid sequence that is at least 90% homologous to SEQ ID NO: 31, SEQ ID NO: 32, an amino acid sequence that is at least 90% homologous to SEQ ID NO: 32, SEQ ID NO: 33, an amino acid sequence that is at least 90% homologous to SEQ ID NO: 33, SEQ ID NO: 34, an amino acid sequence that is at least 90% homologous to SEQ ID NO: 34, SEQ ID NO: 35, an amino acid sequence that is at least 90% homologous to SEQ ID NO: 35, SEQ ID NO: 36, an amino acid sequence that is at least 90% homologous to SEQ ID NO: 36, SEQ ID NO: 37, an amino acid sequence that is at least 90% homologous to SEQ ID NO: 37, SEQ ID NO: 38, an amino acid sequence that is at least 90% homologous to SEQ ID NO: 38, SEQ ID NO: 39, and an amino acid sequence that is at least 90% homologous to SEQ ID NO: 39.

31. The composition of claim 22, wherein the detectable label comprises a fluorescent molecule, stable metal isotope, or oligonucleotide.

* * * * *